US009335247B2

(12) United States Patent
Sharpe et al.

(10) Patent No.: US 9,335,247 B2
(45) Date of Patent: May 10, 2016

(54) ASSEMBLIES AND METHODS FOR REDUCING OPTICAL CROSSTALK IN PARTICLE PROCESSING SYSTEMS

(71) Applicant: CYTONOME/ST, LLC, Boston, MA (US)

(72) Inventors: Johnathan Charles Sharpe, Hamilton (NZ); Donald Francis Perrault, Jr., Brighton, MA (US); Emanuel Tito Mendes Machado, Merrimack, NH (US); Blair D. Morad, Ipswich, MA (US)

(73) Assignee: CYTONOME/ST, LLC, Boston, MA (US)

( * ) Notice: Subject to any disclaimer, the term of this patent is extended or adjusted under 35 U.S.C. 154(b) by 0 days.

(21) Appl. No.: 14/210,366

(22) Filed: Mar. 13, 2014

(65) Prior Publication Data
US 2014/0370536 A1 Dec. 18, 2014

Related U.S. Application Data

(60) Provisional application No. 61/784,431, filed on Mar. 14, 2013.

(51) Int. Cl.
G01N 15/14 (2006.01)
G01N 15/10 (2006.01)

(52) U.S. Cl.
CPC ........ G01N 15/1434 (2013.01); G01N 15/1429 (2013.01); G01N 15/10 (2013.01); G01N 15/14 (2013.01)

(58) Field of Classification Search
USPC ................................................ 356/335–344
See application file for complete search history.

(56) References Cited

U.S. PATENT DOCUMENTS 5,453,838 A * 9/1995 Danielian .............. G01D 5/268
250/227.11
5,862,285 A * 1/1999 Danielian ............ G01N 21/474
385/116

(Continued)

FOREIGN PATENT DOCUMENTS

JP 2008/039477 A 2/2008
WO 2013/028947 A1 2/2013

OTHER PUBLICATIONS

International Preliminary Report on Patentability issued in International Application No. PCT/US2014/026877, issued Sep. 15, 2015.

(Continued)

*Primary Examiner* — Kara E Geisel
*Assistant Examiner* — Jarreas C Underwood
(74) *Attorney, Agent, or Firm* — McCarter & English, LLP

(57) ABSTRACT

The present disclosure relates to optical crosstalk reduction in particle processing (e.g., cytometry including flow cytometry using microfluidic based sorters, drop formation based sorters, and/or cell purification) systems and methods in order to improve performance. More particularly, the present disclosure relates to assemblies, systems and methods for minimizing optical crosstalk during the analyzing, sorting, and/or processing (e.g., purifying, measuring, isolating, detecting, monitoring and/or enriching) of particles (e.g., cells, microscopic particles, etc.). The exemplary systems and methods for crosstalk reduction in particle processing systems (e.g., cell purification systems) may be particularly useful in the area of cellular medicine or the like. The systems and methods may be modular and used singly or in combination to optimize cell purification based on the crosstalk environment and specific requirements of the operator and/or system.

20 Claims, 41 Drawing Sheets

(56) References Cited

U.S. PATENT DOCUMENTS

| | | | |
|---|---|---|---|
| 6,248,590 B1 * | 6/2001 | Malachowski | G01N 15/1404 209/127.4 |
| 6,277,668 B1 * | 8/2001 | Goossen | H01S 5/0262 438/69 |
| 7,010,226 B2 * | 3/2006 | Le Sauze | H04Q 11/0005 398/45 |
| 7,582,880 B2 * | 9/2009 | Wallace | G01T 3/06 250/390.11 |
| 8,089,048 B2 * | 1/2012 | Schmitt | G01T 1/201 250/362 |
| 8,471,921 B1 * | 6/2013 | Li | H04N 9/045 348/222.1 |
| 8,547,540 B2 * | 10/2013 | Beckstead | G01J 3/02 356/301 |
| 8,861,970 B2 * | 10/2014 | Paslaski | H04B 10/43 398/115 |
| 9,134,221 B2 * | 9/2015 | Lo | G01N 15/1459 |
| 2006/0209301 A1 * | 9/2006 | Gardner, Jr. | G01J 3/02 356/301 |
| 2007/0127027 A1 * | 6/2007 | Kralik | G01N 21/31 356/432 |
| 2007/0188747 A1 * | 8/2007 | Nelson | G01J 3/02 356/300 |
| 2007/0206185 A1 * | 9/2007 | Tuschel | G01J 3/2823 356/301 |
| 2008/0221814 A1 * | 9/2008 | Trainer | G01B 11/08 702/70 |

OTHER PUBLICATIONS

Invitation to Pay Additional Fees issued in International Application No. PCT/US2014/026877, mailed Jul. 21, 2014.

International Search Report and Written Opinion issued in International Application No. PCT/US2014/026877, mailed Sep. 22, 2014.

* cited by examiner

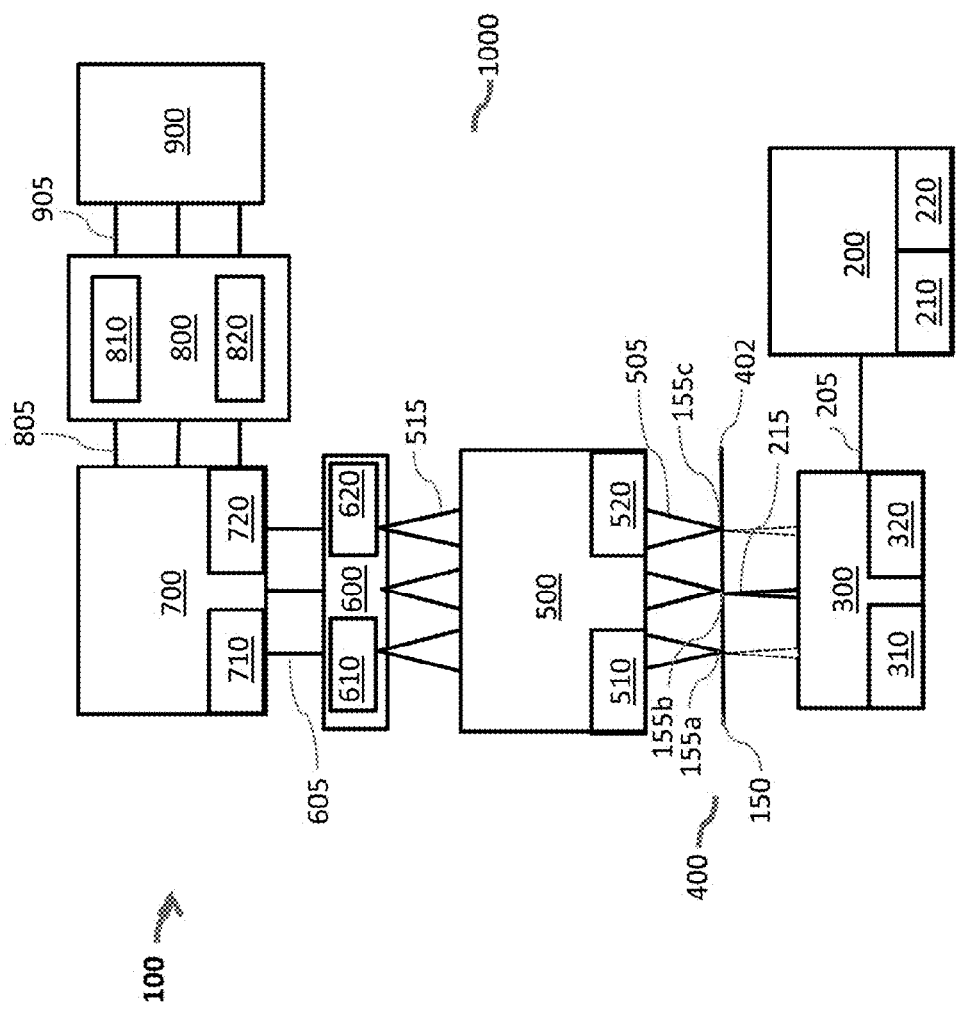

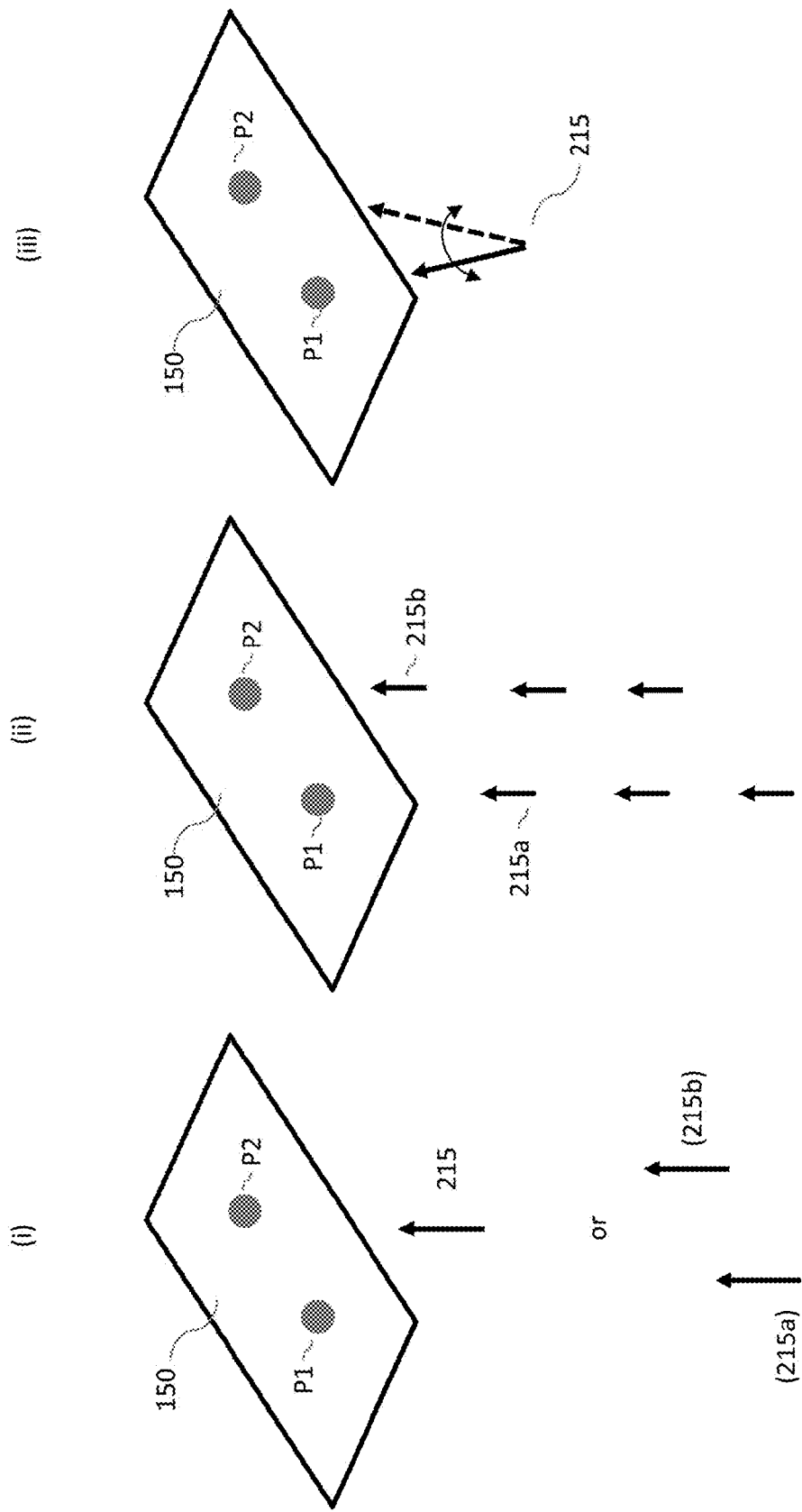

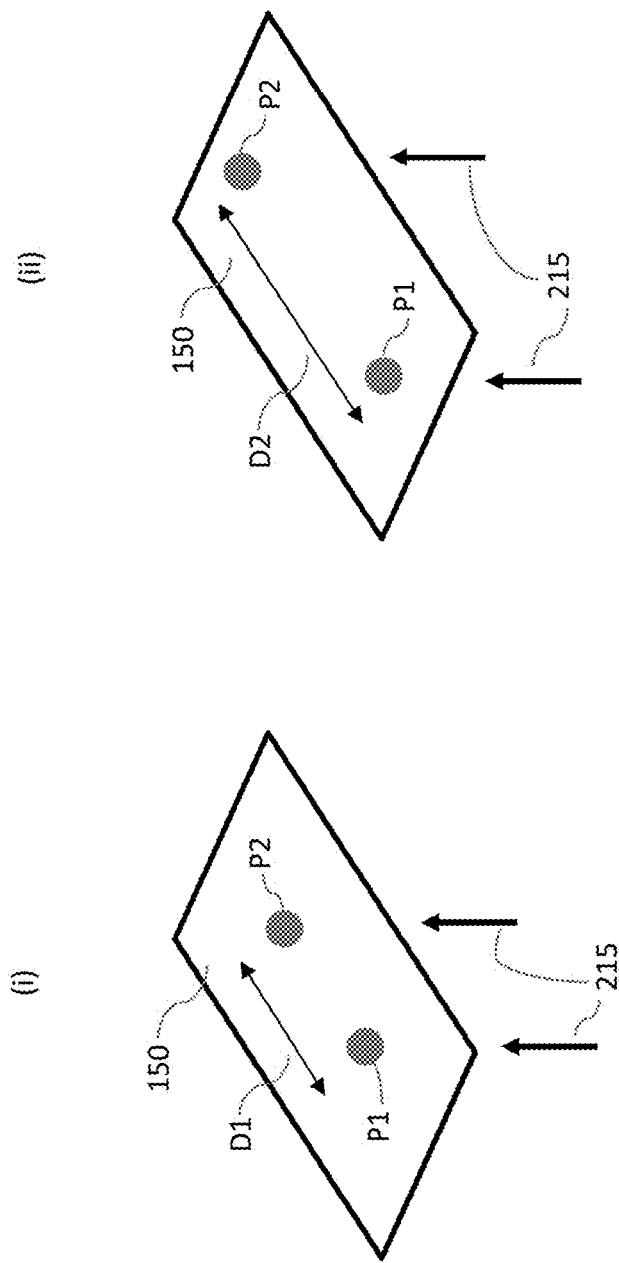

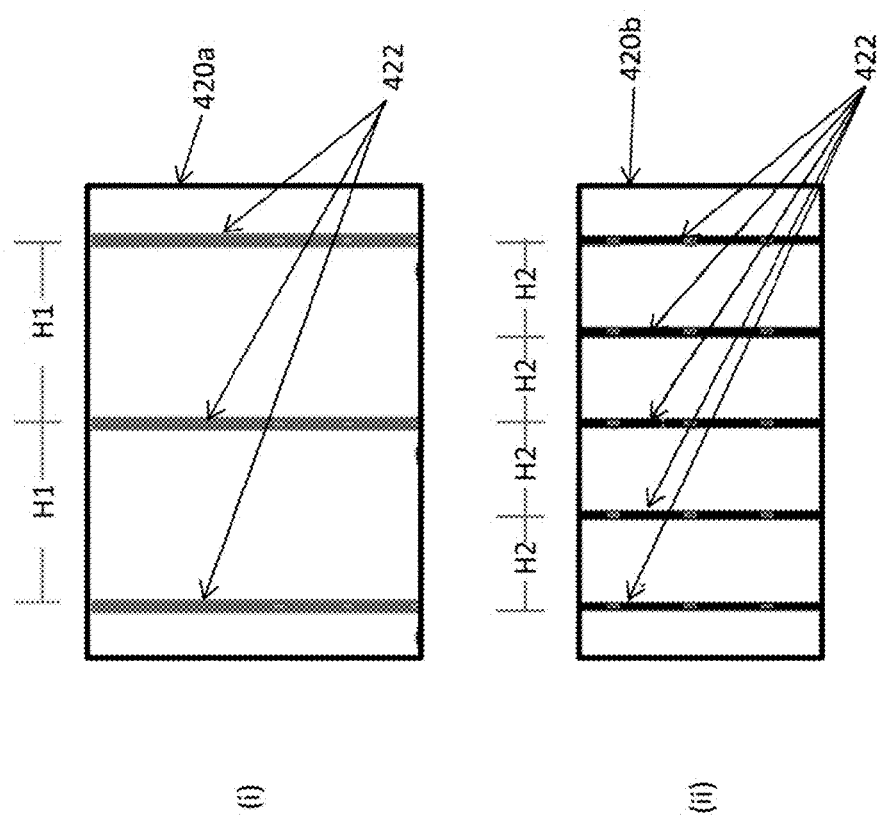

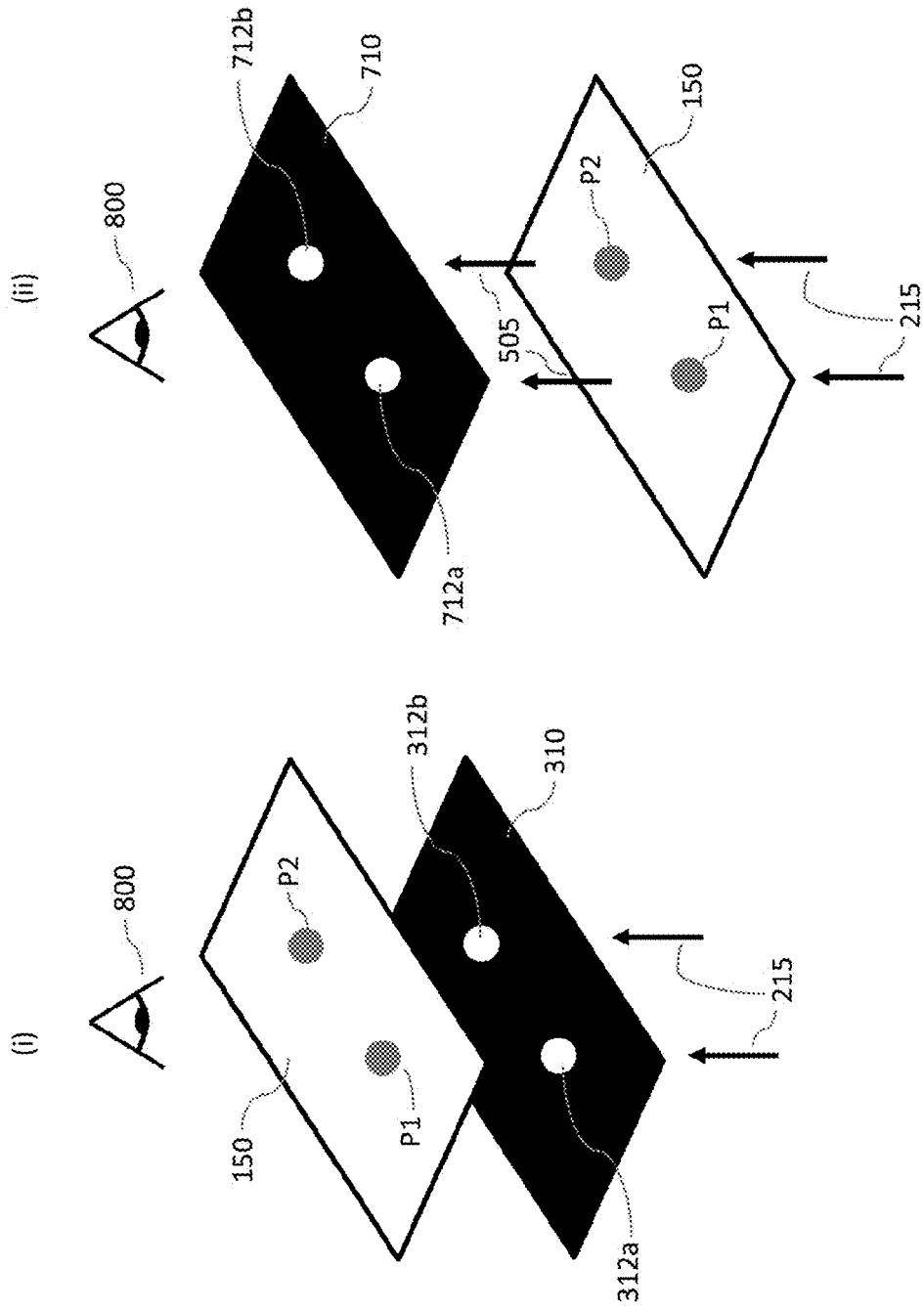

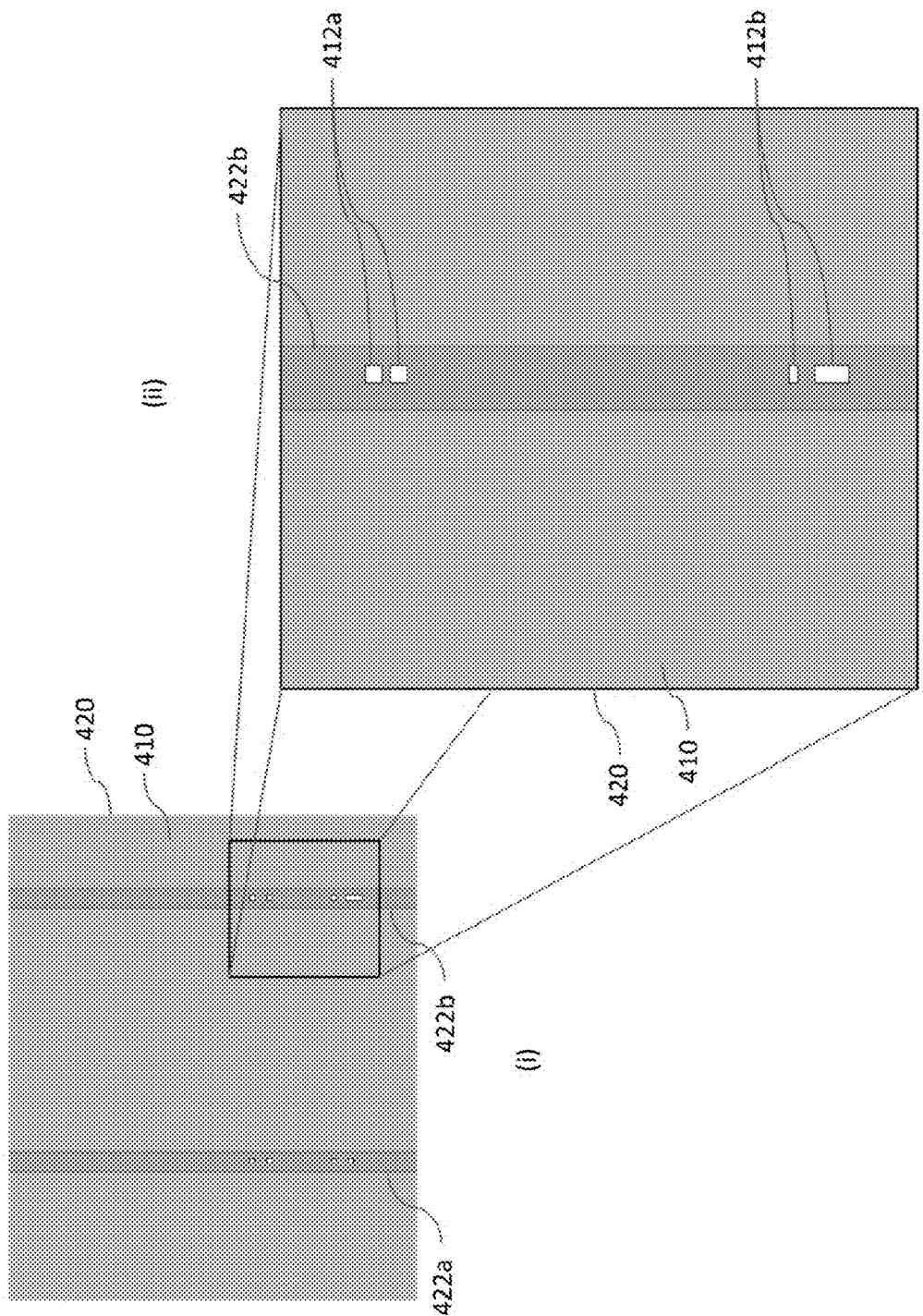

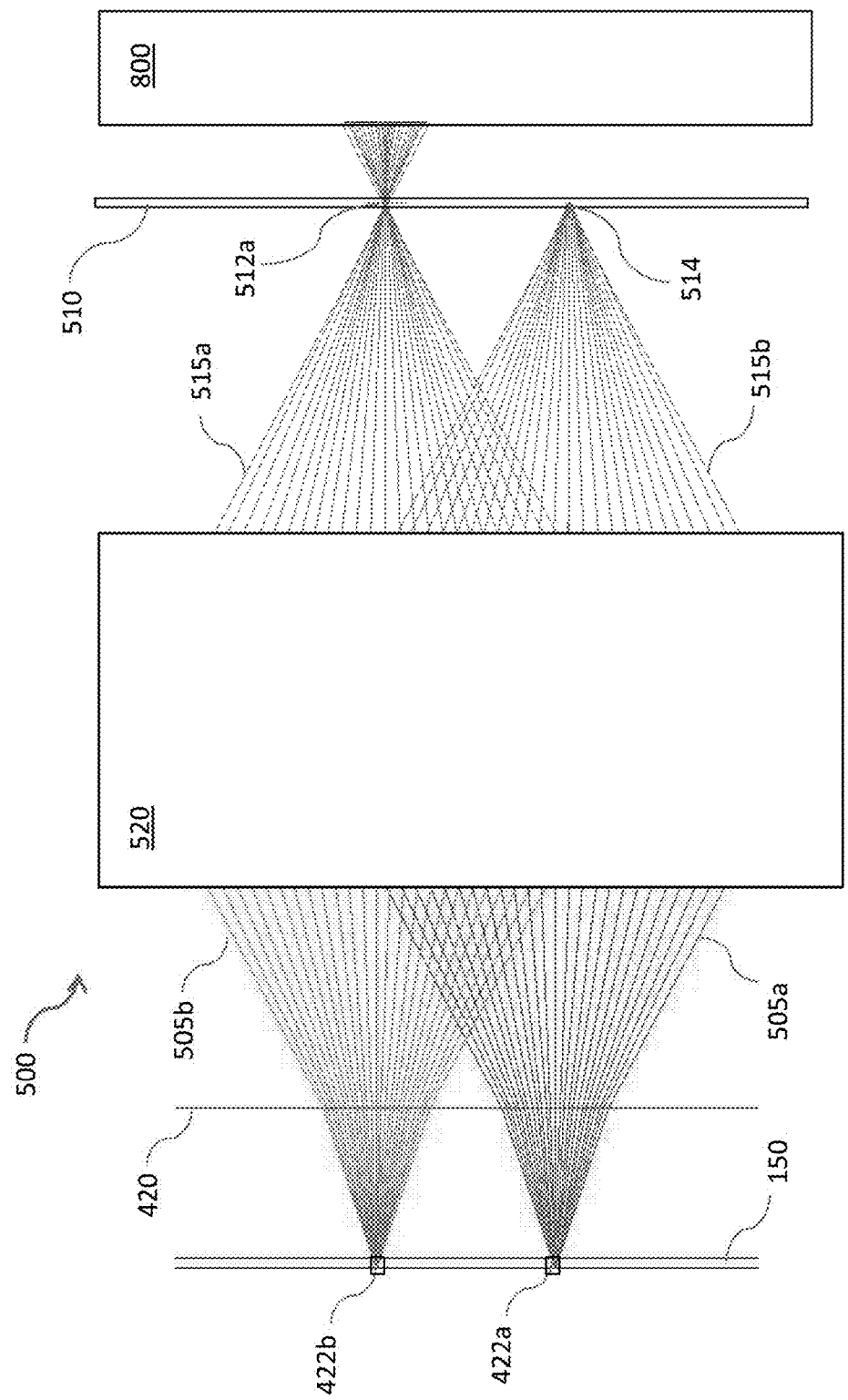

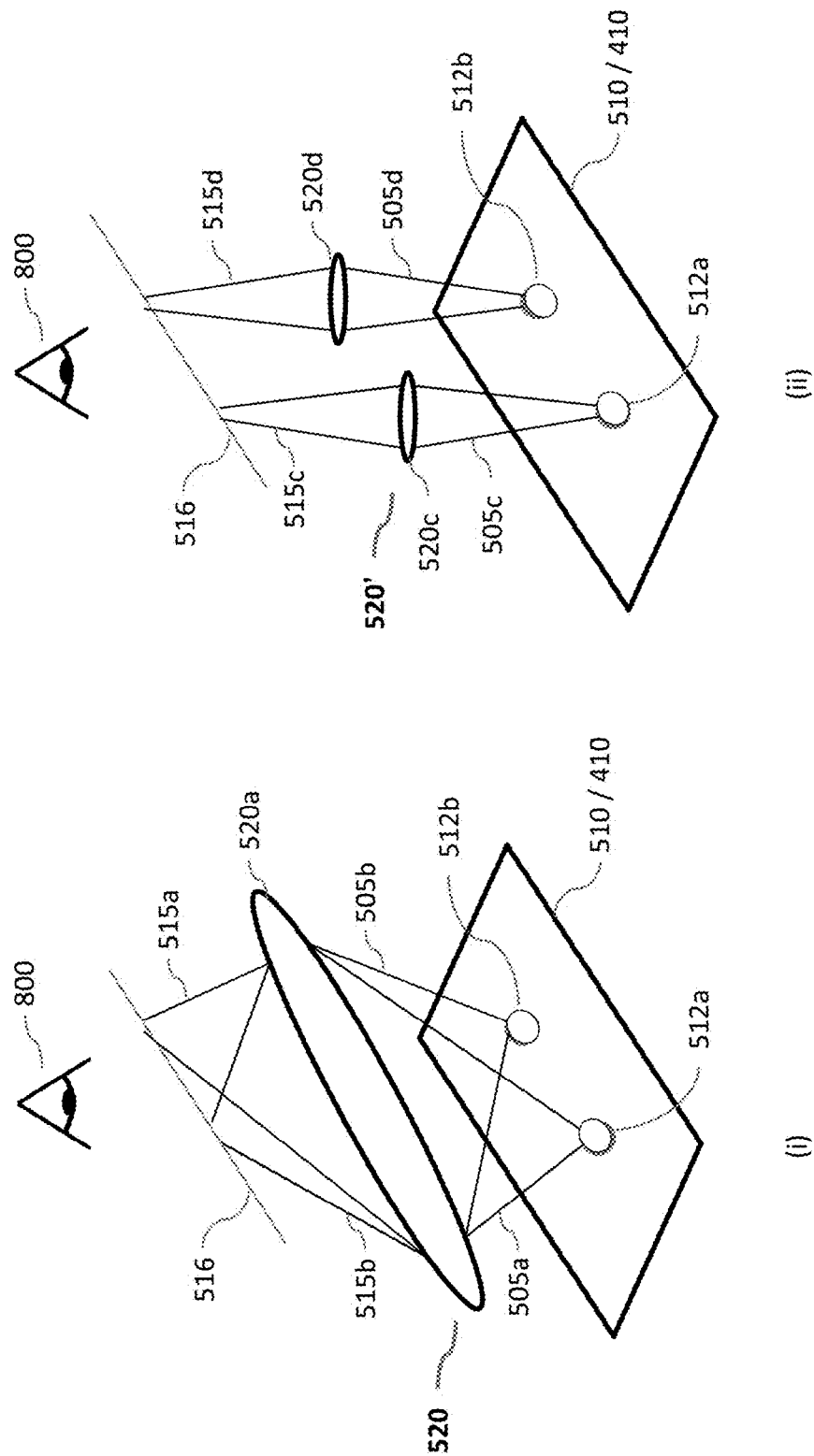

FIG. 1L

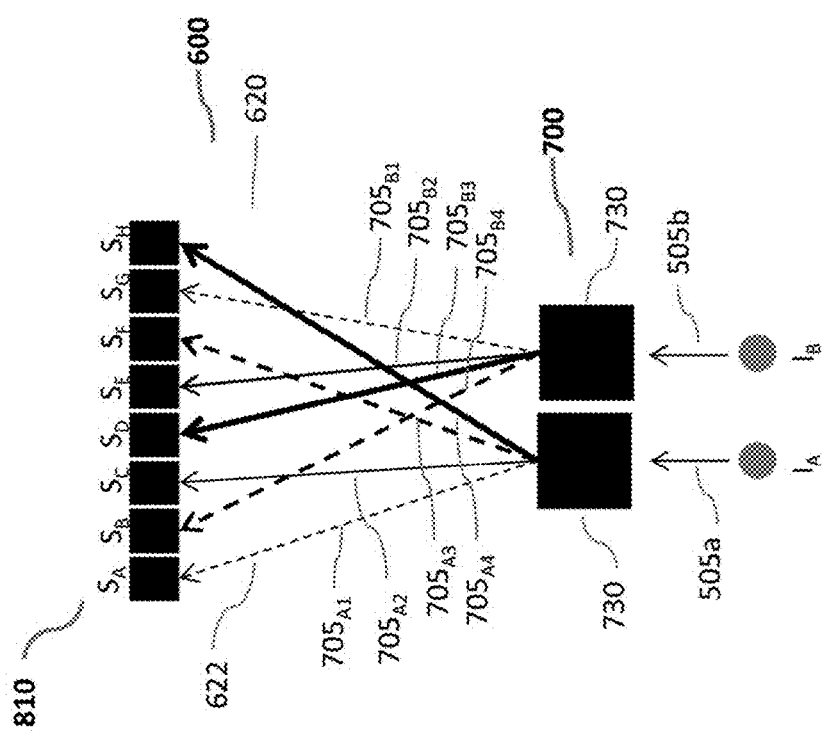

FIG. 1N

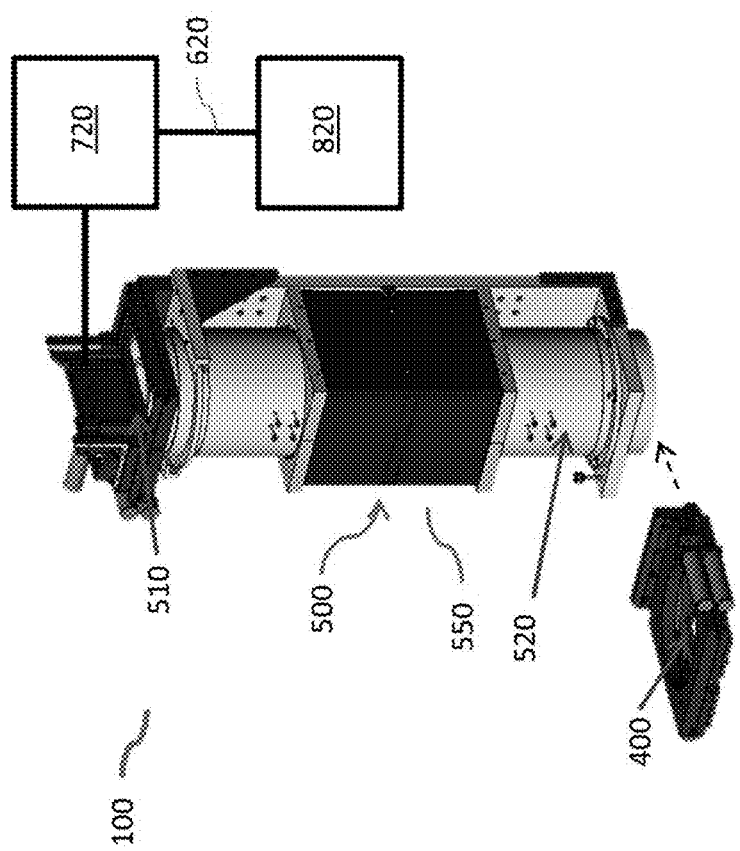

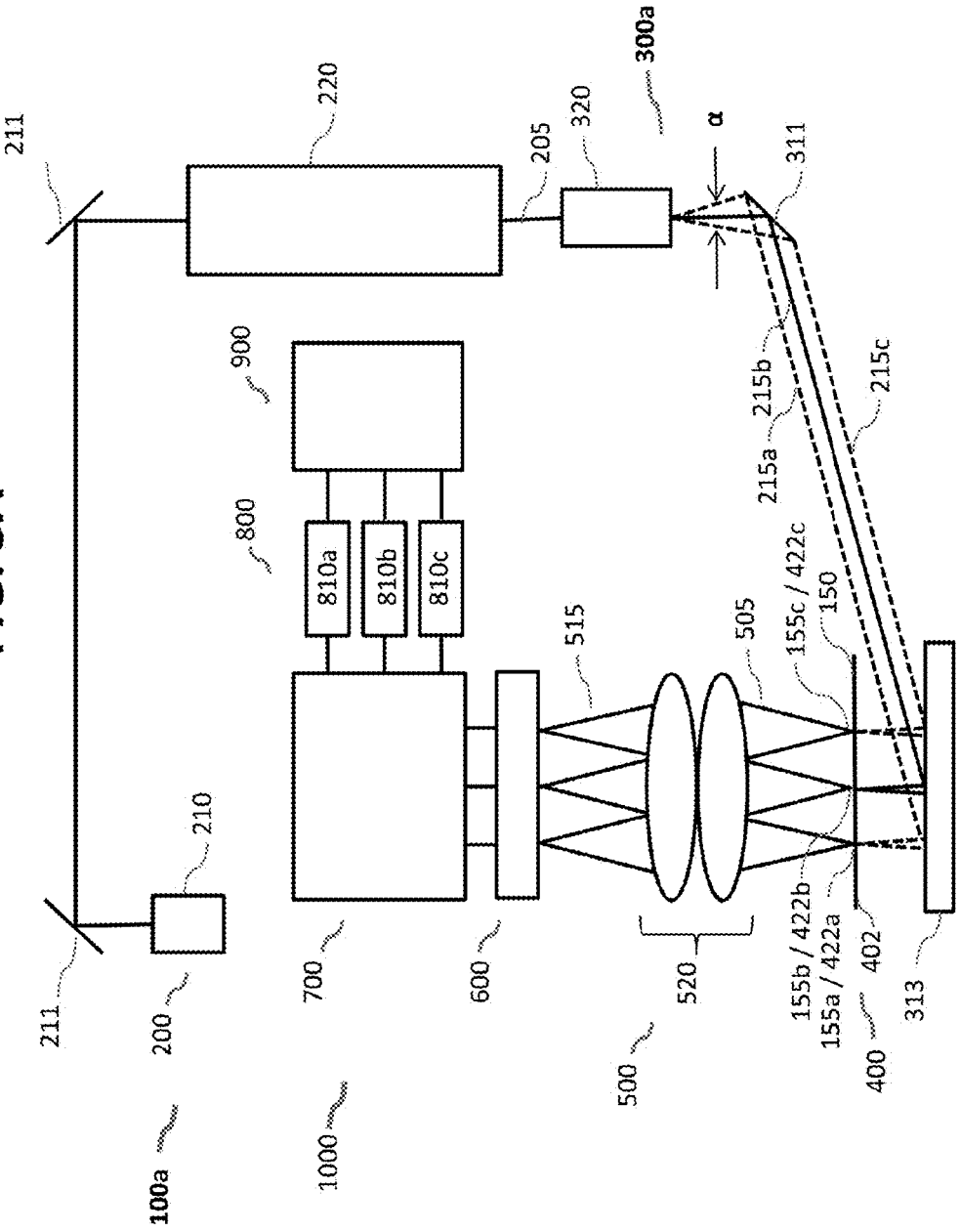

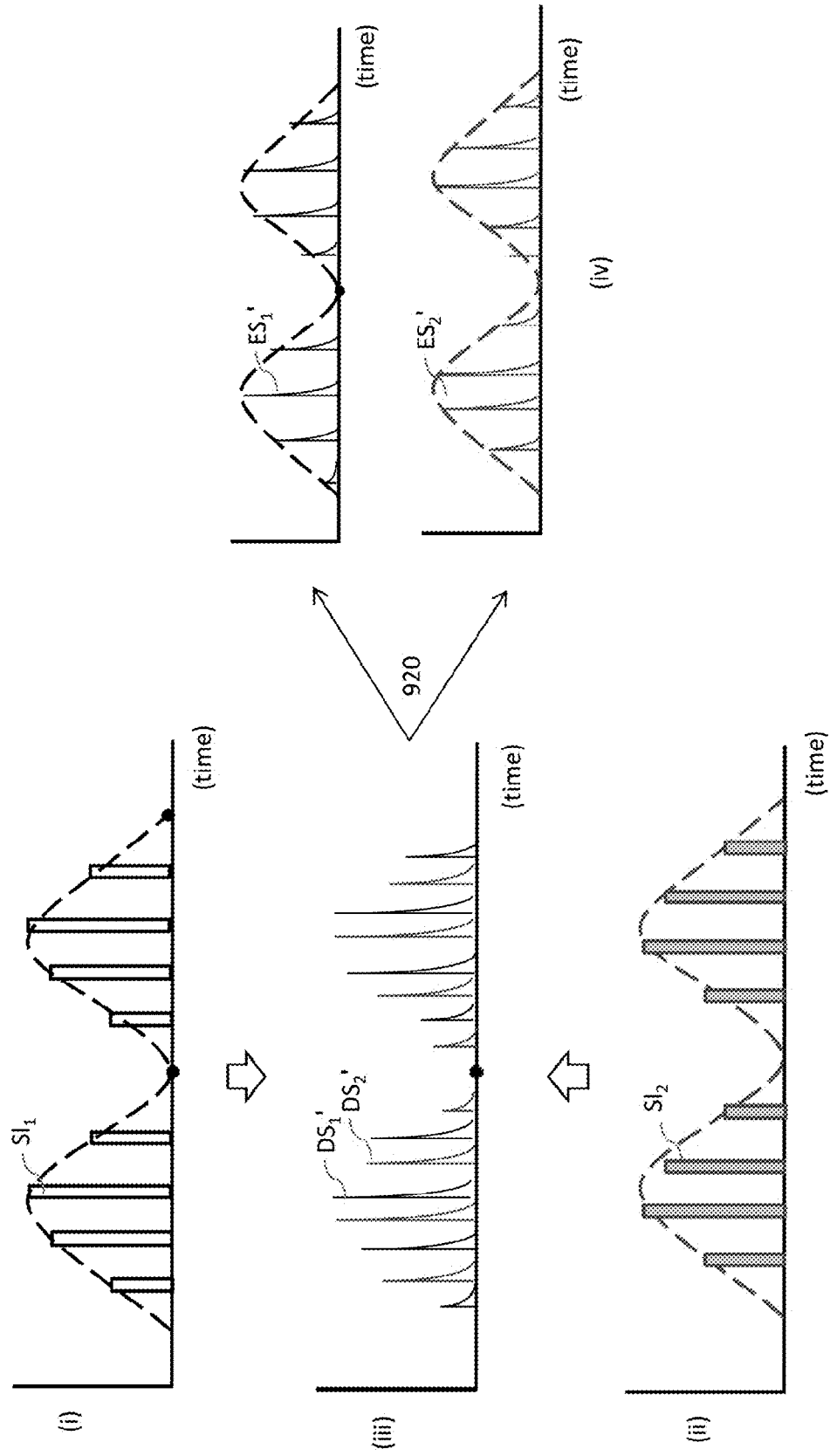

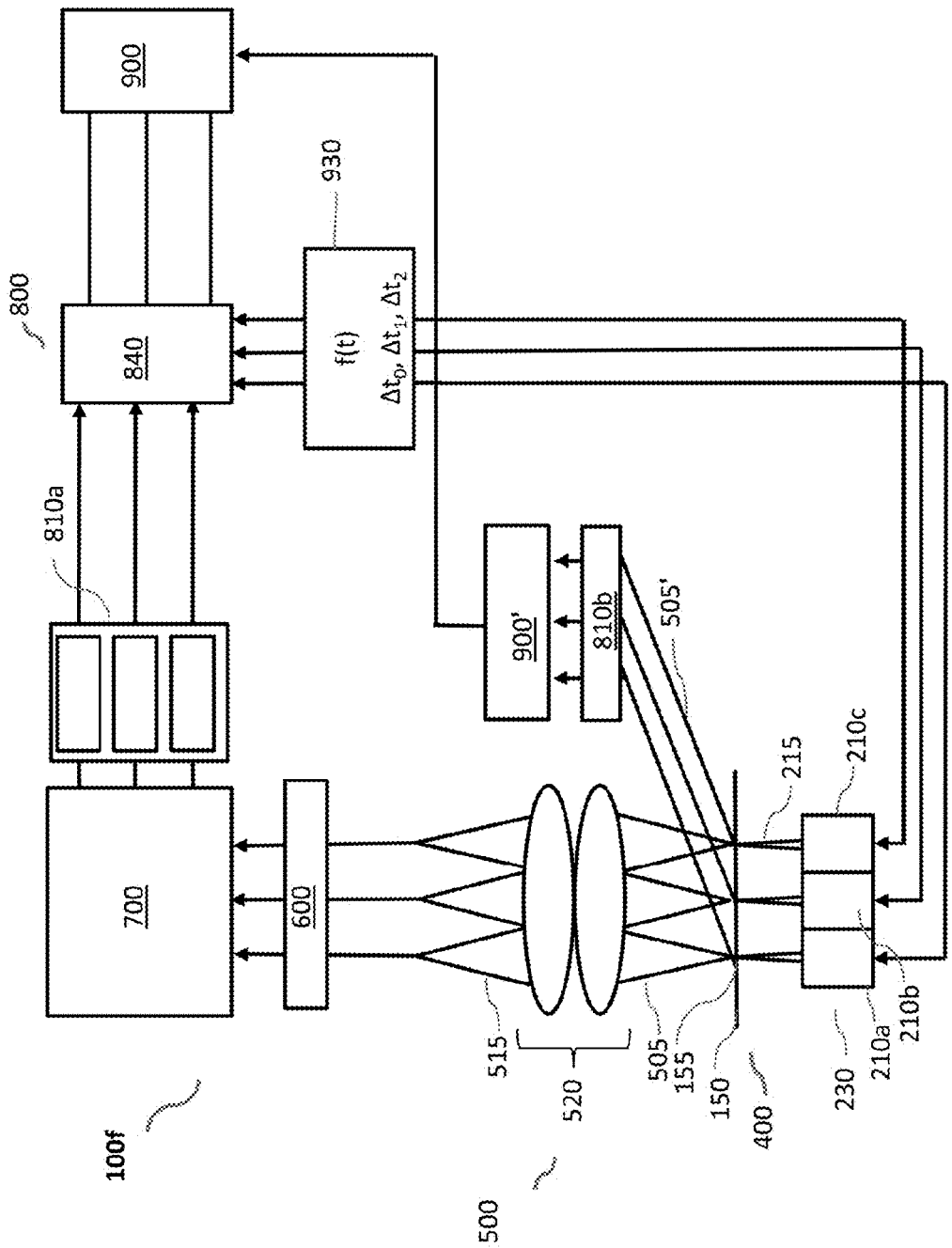

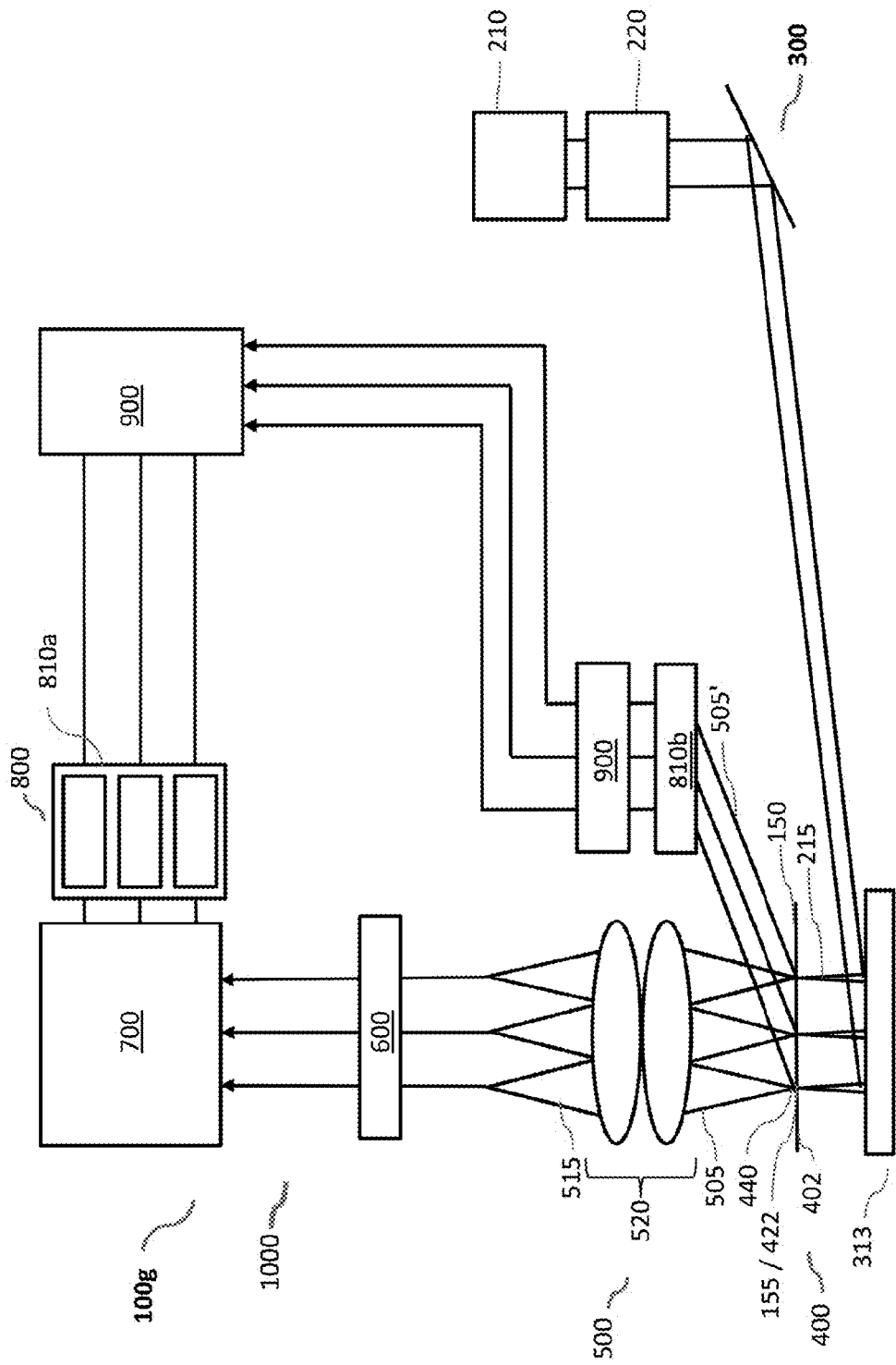

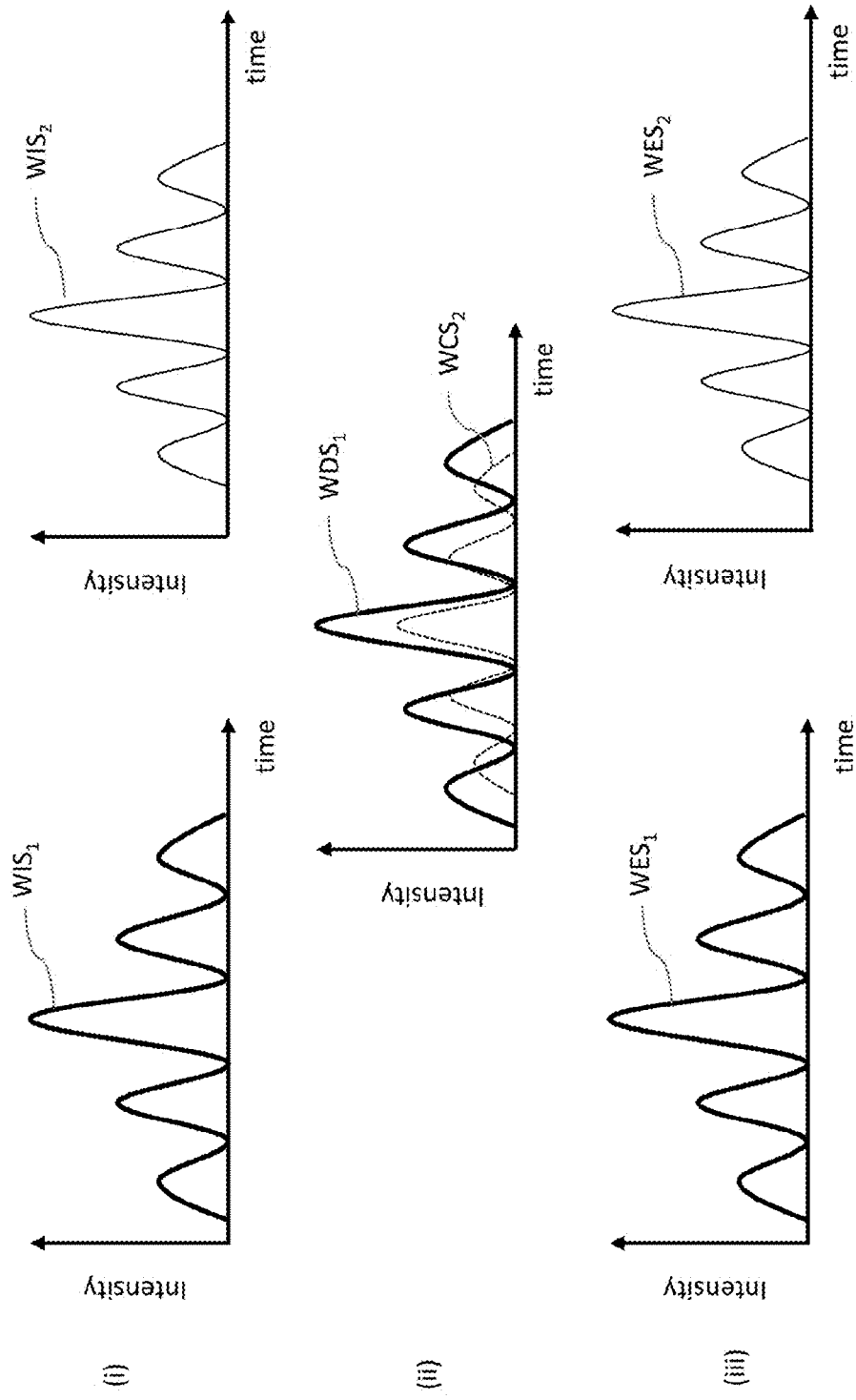

ASSEMBLIES AND METHODS FOR REDUCING OPTICAL CROSSTALK IN PARTICLE PROCESSING SYSTEMS

RELATED APPLICATION

This application claims the benefit of priority to U.S. Provisional Application Ser. No. 61/784,431, titled "Assemblies and Methods for Reducing Optical Crosstalk in Particle Processing Systems," and filed Mar. 14, 2013, the content of which is hereby incorporated by reference in its entirety.

TECHNICAL FIELD

The present disclosure relates to crosstalk reduction, and particularly, to reducing optical crosstalk in particle processing systems.

BACKGROUND

In general, particle processing (e.g., cytometry) systems (e.g., cytometers) and methods are known. For example, some approaches to particle processing or analyzing (e.g., cell purification) systems such as sorting flow cytometers and other particle processing systems have proven to be useful in life science research, industrial, agricultural, diagnostics, and other medical applications.

In general, a cytometer can be described as a system that can measure large numbers of homogeneous and/or heterogeneous particle sets to achieve statistically relevant data sets that can be used to group and/or identify subpopulations that reside within a given particle population (e.g., within one or more samples). These measurements are sometimes performed optically (whether they are intrinsic or responsive to an optical stimulus), or they may be electrical in nature (or some other physical, chemical, or biological characteristic) as a stream of particles passes through a measurement or inspection zone. The particle sets may include biological entities such as cells (e.g., bacteria, viruses, organelles, yeasts, spores, genetic material, spermatozoa, egg cells, multicellular organisms), or other organisms, or other naturally occurring or synthetic/synthetically derived objects.

With the addition of sort functionality, a cytometer can also be used to isolate (e.g., physically separate) one or more particles of interest from a given sample through operator control. See, e.g., U.S. Pat. No. 6,248,590, the entire content of which is hereby incorporated by reference in its entirety. In general, this technique can be used to classify and/or separate (e.g., purify or enrich) one or more populations as defined by the operator.

Cell purification means, such as flow cytometry, can be used to process microscopic particles of biological interest, such as cells or viruses, based on optical properties of the particles. However, when multiple sensors are in use, there exists the possibility that attributive interference or optical crosstalk may occur, which can limit the ability to provide broad accurate dynamic measurement ranges for the sensing locations and/or particles of interest.

For example, it is desired that any light emanating from one particle sensing location should not interfere with the light being measured from another particle sensing location. If there is any such optical crosstalk interference, then some measurements made may be erroneous, and the further data analysis and/or further processing steps (such as producing a diagnostic assessment, or separation based on measured and/or differentiated characteristics) are likely to be affected.

Some measured characteristics of particles positioned at one sensing location may then mask or be masked by characteristics of another particle at another location. An example of this effect may be seen when a very low-response (e.g. dimly fluorescent) particle is to be measured while a particle with bright fluorescence happens to be within an additional sensing location within a similar timeframe. As a non-limiting example, if there is potential for optical crosstalk within a given system, the dim particle may be erroneously measured as being brighter than it actually is, since an amount of light signal emanating from the bright particle may also be captured.

The likelihood of such optical crosstalk may be increased when there is close proximity of sensing locations, or when particles are located on the same substrate or sensing region, or other common optical componentry or light paths. Thus, measurement accuracy may be compromised, which could cause issues in diagnostic applications, e.g., where critical treatment decisions are based on such measurements.

Additionally, in cell purification applications and cell sorting, such erroneous measurements may restrict the ability to provide suitable sub-populations with suitable purity, recovery, and/or yield, since unwanted particles or cells may be inadvertently separated based on inaccurate particle classification. It is therefore desirable to have systems and methods for reducing such optical crosstalk in particle analysis systems and/or cell purification systems.

SUMMARY

The present disclosure provides crosstalk reduction in particle processing (e.g., microfluidic based sorters, drop formation based sorters, and/or cell purification) systems and methods in order to improve performance. More particularly, the present disclosure relates to assemblies, systems and methods for minimizing optical crosstalk during the analyzing, sorting, and/or processing of particles (e.g., cells, microscopic particles, etc.).

The present disclosure provides signal processing systems (e.g., light excitation or illumination systems, on-chip aspects, light collection and detection systems, combined optical and electronic systems (excitation and collection/detection systems)) designed to minimize crosstalk and methods of using such systems. In certain embodiments, the present disclosure relates to the processing and/or measurement of particles within a microfluidic system where multiple sensors are employed. In other embodiments, the present disclosure relates to the processing of particles utilizing drop based sorters or the like.

As such, one embodiment of the present disclosure is directed generally to a signal processing system including a multi-element photodetector assembly or array (e.g., a CCD array, CMOS array, photodiode array photomultiplier tube (PMT) array) which senses signals from multiple particle sensing locations and one or a plurality of wavebands. In certain embodiments, the signal processing system includes a light collection system which senses and processes optical signals. In certain embodiments, the light collection system includes an array, the array further including a dichroic block, a detector, and a scrambled fiber bundle disposed therebetween (e.g., disposed between the dichroic block and the detector). The system may further include image plane confocal apertures, a single lens system and a microfluidic chip array with illumination apertures. The system may further include a plurality of flow channels or paths provided by capillaries, cuvettes, and/or nozzles that may form one or more fluid streams, jets and/or droplets.

The present disclosure is further directed to a method of using a signal processing system including a light collection system which minimizes optical crosstalk. The method may comprise the following steps combined or in the alternative: separating the flow channels; using large span optical systems for excitation and collection; using spatial filters which employ pinholes on-chip and off chip near object, image, or near Fourier planes; using isolated optical pick-up systems, where light from a plurality of particle (sensing) locations is collected by an optical system; and/or using scrambled light mapping, which may be spatial or spectral in nature.

Another embodiment of the present disclosure is a signal processing system characterized by its ability to perform spatial and/or temporal modulation at the level of illumination source, or the detector, or the use of heterodyne detection by providing an electronic oscillator generator and a local oscillator array in the event of stationary interference; or when confocal properties are desired, by providing an electronic oscillator generator and a pulse generator.

Another embodiment of the present disclosure is a method for signal modulation.

The present disclosure also provides for a modular system that can be packaged as a kit of components for particular applications in cellular medicine or the like.

The present disclosure provides for a particle processing system including a particle processing region; a signal processing system in communication with the particle processing region; wherein the signal processing system is configured and adapted to reduce crosstalk between a plurality of signal paths to improve performance of the particle processing system. The signal processing system may be an optical signal processing system adapted to reduce optical crosstalk between a plurality of optical paths.

The present disclosure also provides for a signal processing system to minimize crosstalk of a particle processing system including: a signal processing system that maps signals emanating from a plurality of particle sensing locations to a plurality of detector or sensor locations; wherein the mapping alters the order of the signal paths so that signals from adjacent particle sensing locations are reorganized so that they are no longer adjacent at the sensing locations.

The present disclosure also provides for a signal processing system to minimize optical crosstalk of a particle processing system including: an optical system that maps optical signals emanating from a plurality of particle sensing locations to a plurality of photodetector or photosensor locations; wherein the mapping alters the order of optical paths so that light from adjacent particle sensing locations is altered so that they are no longer adjacent at photosensing locations. The present disclosure also provides for a light processing system to minimize optical crosstalk of a particle processing system, wherein the optical system mapping uses optical fibers or a fiber bundle. The present disclosure also provides for a light processing system to minimize optical crosstalk of a particle processing system, wherein the optical system mapping uses mirrors or steering elements.

The present disclosure also provides for a method of using a particle processing system comprising the following steps combined or in the alternative: separating flow channels; using large span optical systems for excitation and collection; using spatial filters which employ pinholes on-chip and off chip near object, image, or Fourier planes; using isolated optical pick-up systems, where light from a plurality of particle locations is collected by the optical system; and using scrambled light mapping, which may be spatial or spectral in nature.

The present disclosure also provides for a optical processing system to reduce optical crosstalk in a particle processing system, the optical processing system including: a multi-element photo-multiplier tube array; wherein the multi-element photo-multiplier tube array is configured and adapted to reduce optical crosstalk to improve performance of the particle processing system. The present disclosure also provides for a optical processing system to reduce optical crosstalk in a particle processing system further including: a dichroic block, a detector, and a scrambled fiber bundle disposed between the dichroic block and the detector; image plane confocal apertures; a single lens system; and a microfluidic chip array with illumination apertures. The present disclosure also provides for an optical processing system to reduce optical crosstalk in a particle processing system, wherein the scrambled fiber bundle is a strategically mapped fiber bundle to photodetector sensor scheme that minimizes optical crosstalk.

In exemplary embodiments, the present disclosure provides for a system having at least some of the following elements/features:

1) illumination or excitation (e.g., where this can be parallel or simultaneous, scanned, switched or pulsed, involve apertures, etc.,);

2) plurality of particle illumination or sensing locations (spacing or proximity to each other, blocking features between each, metal layers or apertures, etc.);

3) optical collection of light (including apertures, imaging systems, lenses, reflective elements, diffractive elements, etc.);

4) spectral selection elements (e.g., including optical filters such as dichroic, neutral density, longpass, bandpass, shortpass or combinations thereof);

5) optical delivery or steering methods (such as scrambling that could be carried out using fibers or other optical elements); and/or 6) photodetection (single or plurality depending on scheme), which may also include electronic techniques such as those used to time excitation or detection of particles relative to a particular sensing location at a particular time.

Any combination or permutation of embodiments is envisioned. Additional advantageous features, functions and applications of the disclosed systems, assemblies and methods of the present disclosure will be apparent from the description which follows particularly when read in conjunction with the appended figures.

BRIEF DESCRIPTION OF THE DRAWINGS

Exemplary embodiments of the present disclosure are further described with reference to the appended figures. It is to be noted that the various features and combination of features described below and illustrated in the figures can be arranged and/organized differently to result in embodiments which are still within the spirit and scope of the present disclosure. To assist those of ordinary skill in the art in making and using the disclosed systems, assemblies and methods, reference is made to the appended figures, wherein:

FIG. 2 depicts an exemplary particle processing system according to the present disclosure;

FIGS. 3A-3E depict other exemplary particle processing systems, methods and data according to the present disclosure;

FIGS. 7A-7B depict other exemplary particle processing systems, methods and data according to the present disclosure;

FIGS. 8A-8D depict other exemplary particle processing systems, methods and data according to the present disclosure;

FIGS. 9A-9D depict other exemplary particle processing systems, methods and data according to the present disclosure;

DETAILED DESCRIPTION

Figure 1I:
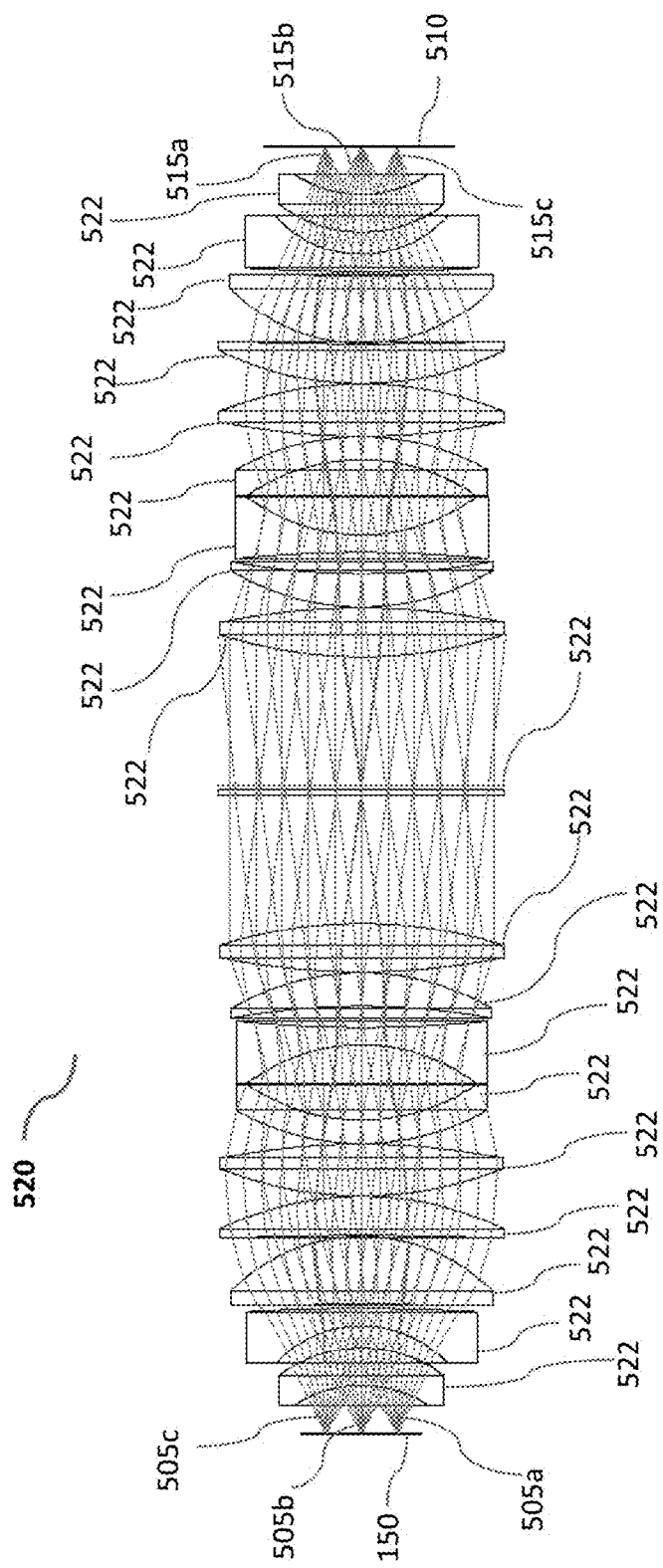
FIGS. 1A-1O depict exemplary features of particle processing systems according to the present disclosure.

In the description which follows, like parts are marked throughout the specification and drawings with the same reference numerals, respectively. Drawing figures are not necessarily to scale and in certain views, parts may have been exaggerated for purposes of clarity.

DEFINITIONS

Crosstalk: can mean, but is in no way limited to, unwanted signal artifacts that enter an signal path and lead to errors in particle or cell measurement, characterization, and/or purification.

Scrambled: can mean, but is in no way limited to, interlaced or interweaved, and/or random or purposefully arranged, and/or out of sequential order.

The present disclosure provides improved optical crosstalk reduction in particle processing (e.g., microfluidic based sorters, drop formation based sorters, and/or cell purification) systems and methods. In general, the present disclosure provides for assemblies, systems and methods for minimizing optical crosstalk during the analyzing, sorting, processing, and/or purifying of particles (e.g., cells, microscopic particles, etc.), thereby providing a significant commercial and/or operational advantage as a result. In certain embodiments, the present disclosure provides a light mapping apparatus and method for high sensitivity (optical) measurement of a plurality of microfluidic channels. In certain embodiments, the present disclosure provides a light mapping apparatus and method for high sensitivity (optical) measurement of a plurality particle flow paths produced by capillaries, nozzles, or jets.

The exemplary systems and methods for crosstalk reduction in particle processing systems (e.g., cell purification systems) may be particularly useful in the area of cellular medicine or the like, and/or cell or particle sorting applications (e.g., industrial cell or particle sorting applications, such as, for example, yeast, veterinary (e.g., sperm), life sciences research and/or applications, etc.). The systems and methods may be modular and used singly or in combination to optimize cell purification based on the crosstalk environment and specific requirements of the operator and system.

In exemplary embodiments, the present disclosure provides assemblies, systems and methods to ensure accurate measurement of optical signals produced by particles from multiple locations on a microfluidic cell purification system by reducing optical crosstalk. The term "crosstalk" is to be understood to encompass unwanted signal artifacts that enter a signal path and lead to errors in particle or cell measurement, characterization, and/or purification. These particles may be contained within or through one or more flow channels, where it is necessary to measure such objects at two or more spatially separated locations, and/or where measurement errors due to crosstalk must be minimized. It is noted that accuracy in purification is of paramount importance, particularly in the area of cellular medicine (e.g., applications requiring optical sensitivity) and related applications, and/or cell or particle sorting applications (e.g., industrial cell or particle sorting applications, such as, for example, yeast, veterinary (e.g., sperm), life sciences research and/or applications, etc.).

The source of such errors can be related to: (i) optical sources that interact with the microfluidic chip and/or particles of interest; (ii) the optical properties of the surrounding material (such as chip scatter or auto-fluorescence as non-limiting examples); (iii) the presence or absence of other particles or debris in close proximity to the particle of interest (e.g., whether in the same or different flow channels, whether stationary or moving); (iv) properties of optical systems that are used to collect and/or transport light emanating from or interacting with light sourced from light sources used (e.g., lenses, mirrors, optical fibers, filters); and/or (v) other considerations such as the sensing method (e.g., sensor type, geometry, spatial separation, optical properties). Additionally, the system may also be applied to non-flow applications but where there is the potential for erroneous measurements due to crosstalk and the like (e.g., optical crosstalk arising from optical imaging systems). For example, the exemplary systems may enable high resolution imaging of cells, other particles and/or microscopic objects to be performed.

If one or more particles are to measured simultaneously or near simultaneously, there is a chance that unwanted light that is destined for one sensor as related to one particle, ends up contaminating (e.g., adding to) the light that is destined for another sensor. Even in the absence of a second particle while a first particle is sensed, there may be unwanted light from other locations that ends up being directed to a first sensor that is related (e.g., matched) to the first particle. This unwanted signal may be (scattered) excitation (e.g. laser, LED, monochromatic, polychromatic, etc.), fluorescence, or other light.

In exemplary embodiments, systems and methods are described herein that reduce the potential for erroneous and/or artificial measurement of particles by employing techniques that minimize unwanted signals from interacting with wanted signals. In general, the systems may utilize a number of approaches in order to reduce unwanted crosstalk. The present disclosure successfully addresses the problem of measuring and differentiating particles, especially dimly fluorescent particles, as sensed from more than one location, whether mobile or stationary. In particle analysis systems that have a large number of sensing locations, or multiple inspection points, it is desired to reduce the complexity, size, and cost of components, in general, and the optical and sensing components, in particular.

When many sensors are required, there is a significant chance that crosstalk may occur, thus limiting the ability to provide a broad dynamic measurement range for all sensing locations and particle located at the various sensing locations.

However, discrete photodetectors that provide sufficient performance (e.g., speed, gain, sensitivity, noise, etc.) can be bulky, expensive, etc. To overcome these issues, a multi-element photodetection system (e.g., a multi-element photo-multiplier tube) has been advantageously developed in order to sense optical signals from not one, but multiple sensor locations (e.g., micro-cytometers or sorters) and multiple wavebands of light for each microcytometer. For example, in one embodiment, electronic mapping of the sensor pixels has been arranged in a certain manner for electronic design purposes.

In exemplary embodiments, it has been determined that electronic mapping of the sensor pixels be arranged in a certain manner for electronic design purposes. After further consideration of the design, calculations, and measurements, it was discovered that a surprising advantage of such an arrangement was that potential issues of crosstalk can be mitigated to a great extent by employing a scattered or scrambled sensor location e.g., utilizing a light collection and transmission path and carefully mapping these transmission paths to a plurality of sensor pixel positions. One illustrative example is using fibers that can easily be moved relative to one another and using them for scrambled light mapping (e.g., mapping these transmission paths to a plurality of sensor pixel positions). This enables a reliable and robust artifact-free measurement and differentiation of particles.

In general, some systems provide for the measurement of particles within a microfluidic system where multiple sensors are employed. The present disclosure provides assemblies and methods to provide accurate measurement of optical signals produced by particles (or other specimens) from multiple locations on a microfluidic system or device. Particles may be defined as nano, micro, or macro-scopic objects (e.g., including atoms, viruses, proteins, organisms, organic or inorganic objects, cells, organelles, microarray spots, metals). In exemplary embodiments, the present disclosure relates to the reliable and robust measurement of particles that flow through optical measurement assemblies and devices.

The particles may be contained within or through one or more flow channels, where there is a desire to measure such objects at two or more spatially separated locations, and where there is a desire to minimize erroneous or artificial measurements due to optical interference, scatter, fluorescence, phosphorescence, crosstalk, etc. (e.g., light capture from something other than the particle of interest that can or not be differentiated from the light that is directly related to that particle).

In exemplary embodiments, the systems and methods of the present disclosure enable or facilitate the reliable and/or robust substantially artifact free and/or minimized measurement and differentiation of particles or other specimens or samples (whether flowing or not). In general, the particles are likely to be located at different points. For the case of a flow-through system, there may be two or more flow paths or channels through which particles travel and are sensed (e.g., often as they interact with an excitation source).

As noted, some exemplary techniques for minimizing the potential for light interference when measuring particles from more than one location include: (i) excitation (e.g., scan and/or modulate excitation source, separate excitation source by spreading particle sensing locations); (ii) spatial filters (e.g., in front of excitation source to restrict light from reaching unwanted areas, near objects and at or near object, Fourier and image planes to reduce field of view of light collection system thereby further minimizing unwanted light from reaching sensors); (iii) isolated optical collection (e.g., multiple optical collection systems and/or paths where the number of paths is less than the number of prescribed particle locations, two particle locations might have two optical collection systems or four particle locations may have two or four optical collection systems); and/or (iv) scrambled (e.g., interlaced/interweaved, random or purposefully arranged) light mapping (using optical fibers or other optical elements such as reflective, refractive, or diffractive elements).

In exemplary embodiments, by scanning and only having one sensing region illuminated (and/or the detection on or enabled), then there should be little or no interference with, or detectable signal from, other sensing regions.

For example, spatial filters (e.g., on the illumination side) limit unwanted light from reaching sensing location (and objects or structure around sensing location) to minimize stray illumination or scatter effects. On the sensing side, spatial filters can provide the necessary keyhole ability to only allow light from a particular region of interest (e.g., the sensing area of interest) to reach sensors or detectors, therefore minimizing stray light from non-target sensing areas from reaching the detectors intended for measurement from target sensing locations.

Moreover, isolated optical collection minimizes any chance of optical crosstalk on the light collection and detection side of the optical system, also lessening the chance of internal scatter, autofluorescence, etc. from one optical channel (e.g., for one sensing location) from interfering with another (e.g., optical channel and related sensing location).

Furthermore, scrambled fibers (i.e., out of sequential order) (when light can be mapped from a plurality of sensing locations to a plurality of optical fibers), the light can be isolated, and purposefully transmitted to pre-defined locations for detection that minimize any further optical crosstalk related to detector geometry or size. Further, the particular spectral content of light, for the case of multiple fluorescent wavebands of interest, can be further interlaced to project and isolate the light particular sensing locations and wavelengths from interfering with light from other sensing locations or wavelengths.

In certain embodiments, the present disclosure provides techniques that maximize particle measurement accuracy in a multi-sensor particle measurement and sorting apparatus. In particular, it is desired that for multi-flow path systems that optical cross talk is minimized. The exemplary systems/methods may also be applied to multiple sensing locations for a single flow path (or static sample measurement system), or multiple sensing locations (e.g., more than one per) for multiple flow channel systems.

As such, exemplary embodiments of the present disclosure provide for the analyzing, monitoring, and/or processing (e.g. sorting, ablating, modifying) of particles. Some potential advantageous uses of the exemplary systems/methods include those instances where some particle characteristics may be weak (e.g. small or low-interaction/transparent particles), or uses that cover a broad dynamic range of response where sensitivity of measurement and therefore insensitivity to optical crosstalk becomes important.

An example of this importance can be when it is desired that a very low-response (e.g. dim fluorescence) particle is to be measured while a particle with bright fluorescence happens to be within an additional sensing location within a similar time-frame. If there is any substantial crosstalk in the system, the dim particle may be erroneously measured as being brighter than it actually is. Thus, measurement accuracy is compromised (which could cause issues in diagnostic applications), and for sorting or other processing steps may result in the particle being acted upon in some manner (e.g. sorted or not sorted) that does not accurately represent what should have occurred if the measurement error due to crosstalk were not encountered.

Some alternative embodiments of the present disclosure include various optical isolation techniques that involve either temporally or spatially isolating illumination paths or geometries, sensing locations, light collection paths or geometries, and/or detector layouts to isolate light (and light wavelength) from a plurality of sensing locations (e.g., scanning approaches, oscillating illumination or detection techniques, spectral un-mixing, separate sensor to sensor displacement).

It is also noted that one may use the scrambled or randomized approach into tapered fiber bundles (rather than the non-scrambled approach) to produce randomized light signals for security reasons as an example, or to take a light profile (Gaussian, laser as an example) and then produce a uniform illumination area from the output of a 2D array of fibers (rather than a Gaussian output).

The present disclosure will be further described with respect to the following non-limiting examples. These examples illustrate the systems and methods of the present disclosure of improved optical crosstalk reduction in particle processing systems and methods.

In exemplary embodiments, the particle processing system may be a microfluidic flow sorter particle processing system configured, dimensioned and adapted for analyzing, sorting, and/or processing (e.g., purifying, measuring, isolating, detecting, monitoring and/or enriching) particles (e.g., cells, microscopic particles, etc.) or the like. However, it is noted that the systems and methods described may be applied to other particle processing systems.

In certain embodiments, the particle processing system may be a cytometer and/or a cell purification system or the like, although the present disclosure is not limited thereto. In exemplary embodiments, the system may be a microfluidic flow sorter particle processing system (e.g., microfluidic chip based system or drop formation particle processing system) or the like. Exemplary microfluidic flow sorter particle processing systems and components or the like are disclosed, for example, in U.S. Pat. Nos. 8,277,764; 8,123,044; 7,569,788; 7,492,522 and 6,808,075; and U.S. Patent Publication Nos. 2012/0009025; 2012/0277902; 2011/0196637 and 2009/0116005; and U.S. Patent Application Ser. Nos. 61/647,821 and 61/702,114, the foregoing being incorporated herein by reference in their entireties.

In further exemplary embodiments, the particle processing system may be a multi-channel or multi-jet flow sorter particle processing system (e.g., multiple capillaries or multiple fluid jet based systems) or the like. Exemplary multi-channel or multi-jet flow sorter particle processing systems and components or the like are disclosed, for example, in U.S. Patent Publication No. 2005/0112541, the entire contents of which is hereby incorporated by reference in its entirety.

In exemplary embodiments, the present disclosure provides for a system and method having at least some of the following elements, features, and/or steps for light mapping: (i) excitation (e.g., scan laser/modulate laser (spatial and/or temporal); (ii) separate flow channels (and use large span optical systems for excitation and collection); (iii) spatial filters (pinholes on-ship and off chip near object, image or Fourier planes); (iv) isolated optical pick-up systems; (v) scrambled light mapping techniques (e.g., using fibers); and/or (vi) modulation (interlaced or high frequency switching and/or lock-in detection or sensing).

In certain embodiments, the present disclosure provides for a light collection system and method having at least some of the following elements, features, and/or steps: (i) simultaneous excitation (excitation source on more than one particle), including separate flow cells and spatial filters (object plane and/or image plane); (ii) isolated optical collection (e.g., light from a plurality of particle locations collected by optical system); and/or (iii) scrambled light mapping (spatial and/or spectral).

In certain embodiments, the present disclosure provides for a modulation system and method having at least some of the following elements, features, and/or steps:
 (i) scan source, including:
  1) angular scan source across chip,
  2) angular scan across a mirror element (e.g., segmented mirror) that reflects part or all of the source being scanned across chip
  3) scan slit/blocker across source,
  4) pulse laser (delay),
  5) pulse individual illumination channels (e.g., all on but timing used to scan),
  6) pulse laser (delay),
  7) use speed of light to differentiate between channels (with high speed detector), but take fluorescence lifetime into account,
  8) use lock-in detection,
  9) spatial pattern/wavelet discrimination, and/or
  10) scan detection pinholes;
 (ii) scan detection, including:
  1) scan pinholes,
  2) optically addressable detection filter (scanning detection blocker),
  3) switch detector, including (a) power (single detector per fluidic channel and/or single detector all fluidic channels), (b) gain (single detector per fluidic channel and/or single detector all fluidic channels), (c) electronics (single detector per fluidic channel and/or single detector all fluidic channels);
 (iii) homodyne, including:
  1) optical homodyne (coherent light),
  2) balanced optical homodyne (coherent light),
  3) electronic homodyne (incoherent light); and
 (iv) heterodyne, including:
  1) optical heterodyne (coherent light),
  2) balanced optical heterodyne (coherent light),
  3) electronic heterodyne (incoherent light).

In exemplary embodiments, scanning across a mirror element (e.g., segmented mirror that reflects part or all of the source being scanned across chip) can minimize the dwell (e.g., dead or non-useful scan) time between channels and/or time not on the channels, therefore maximizing the illumination/excitation time on channels/particle flow paths.

FIG. 1A illustrates the various subsystems and/or components that may generally be included in a particle processing system 100 according to embodiments presented herein. FIG. 1A schematically shows that particle processing system 100 may include a radiation source system 200, a radiation beam control system 300, a particle processing region 400, an emission signal collection system 500, a signal relay system 600, a signal conditioning system 700, a signal detection system 800 and an electronics system 900.

Radiation source system 200 (or illumination source system) provides one or more beams 205 of electromagnetic radiation. Radiation source system 200 may include a single radiation source 210 or multiple radiation sources. Radiation source system 200 may also include beam shaping optics 220 as are known in the art. One or more radiation beams 205 exits the radiation source system 200 and enter the radiation beam control system 300. A radiation source may also be referred to as an excitation and/or illumination source and radiation beams may also be referred to as excitation and/or illumination beams. Radiation refers to electromagnetic radiation of any wavelength; similarly, light refers to electromagnetic radiation of any wavelength. Radiation sources may include lasers, LEDs, arc lamps, incandescent sources, radioactive sources, etc. Beam shaping optics may include refractive, reflective, diffractive, birefringent elements, etc. and any beam shaping, beam combining and/or beam splitting elements.

Radiation beam control system 300 controls how one or more interrogation beams 215 exiting the radiation beam control system impinge on or illuminate interrogation sites 155 provided by an interrogation element 150. The radiation beam control system 300 may control the interrogation beam(s) 215 spatially, temporally, and/or spectrally. Further, the radiation beam control system 300 may direct or manipulate the radiation beam(s) dynamically and/or passively. As one non-limiting example, radiation beam control system 300 may include a spatial filter 310. As other non-limiting examples, radiation beam control system 300 may include an optical scanner 320, other scanners, electro-optical modulators, acousto-optical modulators, galvanic or micro-electromechanical systems (MEMS)-based scanning optical elements, amplitude modulators, phase modulators, frequency modulators, etc.

The one or more interrogation beams 215 may be directed by radiation beam control system 300 to illuminate a particle processing region 400. The particle processing region 400 may include a plurality of interrogation sites 155a, 155b, 155c, etc. within an interrogation element 150. The interrogation element 150 may be provided as part of a microfluidic chip system 402.

Particle processing region 400 may be provided at the input side of the signal collection system 500. As described in more detail below, the particle processing region 400 may be a microfluidic chip system 402 including a plurality of microfluidic flow channels 422. Particles of interest may travel through these microfluidic flow channels. These microfluidic flow channels may define the interrogation element 150 that is exposed to one or more interrogation beams 215 for interrogating the particles. Microfluidic chip system 402 may be provided with specific illumination apertures or masking patterns. Microfluidic chip system 402 may include with a holder for ease of handling and for interfacing with other components of the particle processing system 100. Particle processing region 400 may alternatively be provided with one or more capillaries, cuvettes, nozzles, cassettes, wells, reservoirs, etc.

Emission signals 505 are signals that are emitted from the interrogation element 150. These emission signals 505 may be due to excitation, transmission, scatter, fluorescence, extinction, reflection, refraction, diffraction, etc. and are not limited as to any specific source (e.g., particles, cells, edges, opaque regions, etc.). Emission signals 505, which include the signals of interest, are collected by emission signal collection system 500 and transmitted to signal detection system 800 via a signal relay system 600 and/or a signal conditioning system 700.

An emission signal collection system 500 may include a lens system 520 to shape, focus and/or direct the emission signals 505. The lens system 520 may be provided as a single lens system and/or as an array of lens systems. According to some embodiments, the lens systems 520 may include a set of free optics to collect and/or reimage light or other signals emitted from the interrogation element 150. For example, fluorescence signals emitted from particles excited by an interrogation beam 215 may be focused onto a fluorescence image plane. An example lens system (e.g., 520) may have a numerical aperture of 0.5. The same and/or other lens systems may be used collect other emission signals 505 emanating from the interrogation element 150, for example, extinction and/or scatter signals associated with particles. Further, emission signal collection system 500 may include filters, whether spatial, spectral, long pass, short pass, band pass, etc. Emission signal collection system 500 transmits collection signals 515 to signal relay system 600.

Signal relay system 600 may include a fiber bundle 620 (e.g., a plurality of optical fibers) for transmitting signals 605. This fiber bundle 620 may be provided between, and optically coupled to, emission signal collection system 500 and signal conditioning system 700. Alternatively and/or additionally (as for example shown in FIG. 2) a fiber bundle 620 may be provided between, and optically coupled to, signal conditioning system 700 and signal detection system 800. As will be described in more detail below, according to certain embodiments, the fiber bundle 620 may be provided as a spatially scrambled fiber bundle, as a spectrally scrambled fiber bundle, or as a spatially and spectrally scrambled fiber bundle.

Signal conditioning system 700 may include spatial filters (such as masks 710 having apertures), spectral filters, dichroic arrays 720, etc. As non-limiting examples, signal conditioning system 700 may include long pass filters, short pass filters, band pass filters, notch filters, absorptive elements, interference elements, polarization elements, spectral dispersion elements, etc.

Signal detection system 800 receives detector input signals 805 and converts these into electrical signals 905 for transmission to electronics 900. The signal detection system 800 may include a single detector 810 or a plurality of detectors, for example photomultiplier tubes (PMT), charge collection devices (CCD), avalanche photodiodes (APD), photodiodes, thermopiles, bolometers, etc. The detectors may be arranged as an array of detectors 820. Further, each detector 810 may be provided as one or more sensors.

Electronics system 900 may be configured to acquire, process, characterize, and/or analyze the electrical signals emitted from the signal detection system 800 and/or to control the particle processing system 100. The electrical signals 905 may be analog or digital.

The above-defined systems of the particle processing system 100 may further define a signal processing system 1000. Signal processing system 1000 may be in communication with one or more of the radiation source system 200, the radiation beam control system 300, the particle processing region 400, the emission signal collection system 500, the signal relay system 600, the signal conditioning system 700, the signal detection system 800, the electronics system 900, and/or portions thereof. The signal processing system 1000 may create, acquire, manipulate, process, transmit, eliminate, augment, etc. signals (including electromagnetic, electrical, acoustic, optical, etc.) that are involved in processing the particles in the particle processing system 100.

Further, in accord with some embodiments, certain of the above-described systems may be merged with another system, split between one or more other systems, positioned elsewhere in the optical path, duplicated and/or eliminated. Thus, for example, radiation beam control system 300 may be eliminated or subsumed into radiation source system 200, in which case radiation beam(s) 205 and interrogation beam(s) 215 may be one and the same. As another example, signal conditioning system 700 may be eliminated or subsumed into emission signal collection system 500 or alternatively into signal detection system 800, in which case signals 605 exiting from signal relay system 600 and detector input signals 805 may be one and the same.

FIG. 1B illustrates various modes that may be used to excite or interrogate the particles P flowing through (or positioned within) interrogation sites 155 of the interrogation element 150. The interrogation element 150 may be located within a particle processing region 400 which may include one or more microfluidic flow channels, wells, chambers, etc. (not shown). Thus, according to certain embodiments, the plurality of particles P1, P2 being illuminated and/or excited may be flowing within a single microfluidic channel or positioned within a single portion (such as a well or chamber) of the particle processing region 400. Alternatively and/or additionally, the excited particles P1, P2 may be flowing within two or more of the microfluidic flow channels, wells, chambers, etc. As schematically illustrated in FIG. 1B(i), a plurality of particles P1, P2 may be simultaneously excited by a single interrogation beam 215 (or by a plurality of interrogation beams 215a, 215b). The single interrogation beam 215 may be generated by a single radiation source 200 or may be generated by a plurality of radiation sources 210a, 210b having their radiation beams 205a, 205b combined into a single interrogation beam 215. Optionally, a plurality of interrogation beams 215a, 215b may be generated by a single radiation source 200 having its radiation beam 205 split into the plurality of interrogation beams 215a, 215b or may be generated by a plurality of radiation sources 210a, 210b.

As shown schematically in FIGS. 1B(ii) and 1B(iii), a particle P or a plurality of particles P1, P2 in the interrogation element 150 may be non-simultaneously excited (for example, sequentially) by one or more interrogation beams 215a, 215b. FIG. 1B(ii) shows that one or more interrogation beams 215a, 215b may sequentially or alternatively interrogate the particle(s) P. For example, first and second interrogation beams 215a, 215b may be alternatively pulsed so as to sequentially excite first and second particles P1, P2 (or to sequentially excite a single particle P). Optionally (not shown), there may be only a single interrogation beam 215 and a means for selectively blocking the interrogation beam from interrogating both particles P1, P2 at the same time may be provided. FIG. 1B(iii) shows that a plurality of particles P1, P2 may be sequentially or non-simultaneously excited or illuminated by an interrogation beam 215 that selectively scans or moves over the interrogation element 150. Relative to the excitation mode of FIG. 1B(i), the excitation modes of FIGS. 1B(ii) and 1B(iii) generally lessen potential crosstalk problems.

FIG. 1C schematically illustrates that, at a very basic level, optical crosstalk may be eliminated or lessened by increasing the distance D between the particles P being interrogated. Thus, increased distance D2 between particles P1, P2 (and/or between flow paths within which the particles travel) as shown in FIG. 1C(ii) as compared to a lesser distance D1 (i.e., closer proximity) between particles P1, P2 (and/or between flow paths within which the particles travel) as shown in FIG. 1C(i), may result in less crosstalk. For example, the amount of overlap between interrogation beams 215a, 215b, the amount of optical interaction between particles and/or adjacent material, and the amount of optical interaction of signals being collected for detection may all be reduced by increasing the spacing or distance D between the particles P. Unfortunately, competing design considerations generally preclude spacing the particles far enough apart to completely eliminate crosstalk.

FIG. 1D(i) shows a portion of a first microfluidic chip's substrate 420a provided with three microfluidic flow channels 422 arranged in a relatively low density channel spacing H1; FIG. 1D(ii) shows a portion of a second microfluidic chip's substrate 420b provided with five microfluidic flow channels 422 arranged over the same width, but with a relatively high density channel spacing H2.

FIG. 1E schematically illustrates that optical crosstalk may be mitigated by spatially filtering the interrogation beam(s) 215 interrogating the particles P1, P2 (FIG. 1E(i)) and/or by spatially filtering the emission signals 505 exiting the interrogation element 150 (FIG. 1E(ii)). Spatial filters include angular filters. In FIG. 1E(i), a spatial filter or mask 310 is shown located between the interrogation beam 215 and the interrogation element 150. Mask 310 is provided with one or more apertures 312a, 312b that only allow energy from the interrogation beam(s) 215 to reach interrogation element 150 at specific locations. In FIG. 1E(ii), a spatial filter or mask 710 is shown located between the interrogation element 150 and the signal detection system 800. Mask 710 is provided with one or more apertures 712a, 712b that only allow energy emitted from the particles P1, P2 or other interrogated components to reach signal detection system 800 from specific locations of the interrogation element 150. For certain embodiments, these locations on or in the interrogation element 150 may coincide with the flow channels 420 of the particle processing region 400 and more specifically, may coincide with the particles P flowing through the channels. According to other embodiments, spatial filters or masks may be positioned at or near the interrogation element 150, at or near a Fourier plane of any optical collection system, and/or at or near an image plane.

In an example embodiment, FIGS. 1F(i) and 1F(ii) show a portion of a microfluidic chip's substrate 420 with microfluidic flow channels 422a, 422b and a spatial filter 410 located at or near the detection plate 150. Filter 410 is shown as mask formed as a metal layer provided on the substrate 420 and extending over the flow channels 422a, 422b. Thus, in this particular embodiment, spatial filter 410 is associated with the particle processing region 400. If mask 410 is provided on the excitation side of the interrogation element 150, then the apertures 412a, 412b (shown as pairs of apertures in this particular embodiment) allow restricted portions of the interrogation beams to illuminate within the flow channels 422. If mask 410 is provided on the emission side of the interrogation element 150, then the apertures 412a, 412b allow restricted portions of the emission signals to radiate from within the flow channels 422.

FIG. 1G schematically illustrates a spatial filter 510 associated with an embodiment of an emission signal collection system 500. Microfluidic channels 422a, 422b are positioned at interrogation element 150 within a microfluidic chip's substrate 420. Emission beams 505a, 505b emanate from within microfluidic channels 422a, 422b, respectively, and are collected by lens system 520 of the emission signal collection system 500. Collection signals 515a and 515b, respectively associated with emission beams 505b, 505a and channels 422b, 422a, are spatially filtered by mask 510. Mask 510 has a confocal aperture at 512a that allows collection signal 515a to pass through to the signal detection system 800 (e.g., an optical detection element). Mask 510 blocks collection signal 515b at 514. Thus, in the embodiment of FIG. 1G, spatial filter 510 is associated with the emission signal collection system 500 and further, the spatial filter 510 is used to mask detected light downstream of the lens system 520.

FIG. 1H schematically illustrates two alternative lens systems 520. FIG. 1H(i) illustrates a single lens systems 520a that collects emission signals 505a, 505b from a plurality of particle locations. Lens system 520a may have a plurality of optical elements (not shown) which shape, focus, direct, etc. emission signals 505a, 505b into collection signals 515b, 515a. Collection signals 515a, 515b may be focused at focal plane 516. A spatial filter 510 allows emission from the particles (or specific locations associated with the interrogation element 150) to reach lens system 520a through apertures 512a, 512b and blocks all other emissions. Similarly in FIG. 1H(ii), a spatial filter 510 allows emission from the particles (or specific locations associated with the interrogation element 150) to reach lens system 520 through apertures 512a, 512b and blocks all other emissions. However, in the embodiment of FIG. 1H(ii) the lens system 520 includes a first lens system 520c and a second lens system 520d. Each lens system 520c, 520d may have a plurality of optical elements (not shown) which shape, focus, direct, etc. emission signals 505c, 505d into collection signals 515c, 515c. The collection signals 515c, 515d may be focused at focal plane 516. A spatial filter (not shown) may be provided at focal plane 516. In FIG. 1H(ii) the plurality of lens systems 520c, 520d form an arrayed lens system 520' which provides isolated or independent optical paths for the emission beams 505c, 505d. In general, an arrayed lens system 520' may have any number of individual lens systems 520. Further, the individual lens systems 520 in an arrayed lens system 520' may be identical or may differ.

An example of a single lens system 520 is shown in FIG. 1I. As shown in this particular example, the single lens system includes a plurality of various optical elements 522 in a paired lens configuration. In general, the single lens system 520 may be provided with one or more of any of various optical elements 522 in any of various optical path configurations. Emission signals 505a, 505b, 505c, etc. emanate from interrogation element 150 (which may be provided, for example, within a particle processing region 400). The single lens system 520 receives a plurality of emission signals 505 and as these emission signals travel through the single lens system 520 they may overlap or at least partially overlap. At the downstream end of the optical path, collection signals 515a, 515b, 515c, etc. pass through a spatial filter 510 which may be positioned in a light collection or detection plane.

Figure 1J:
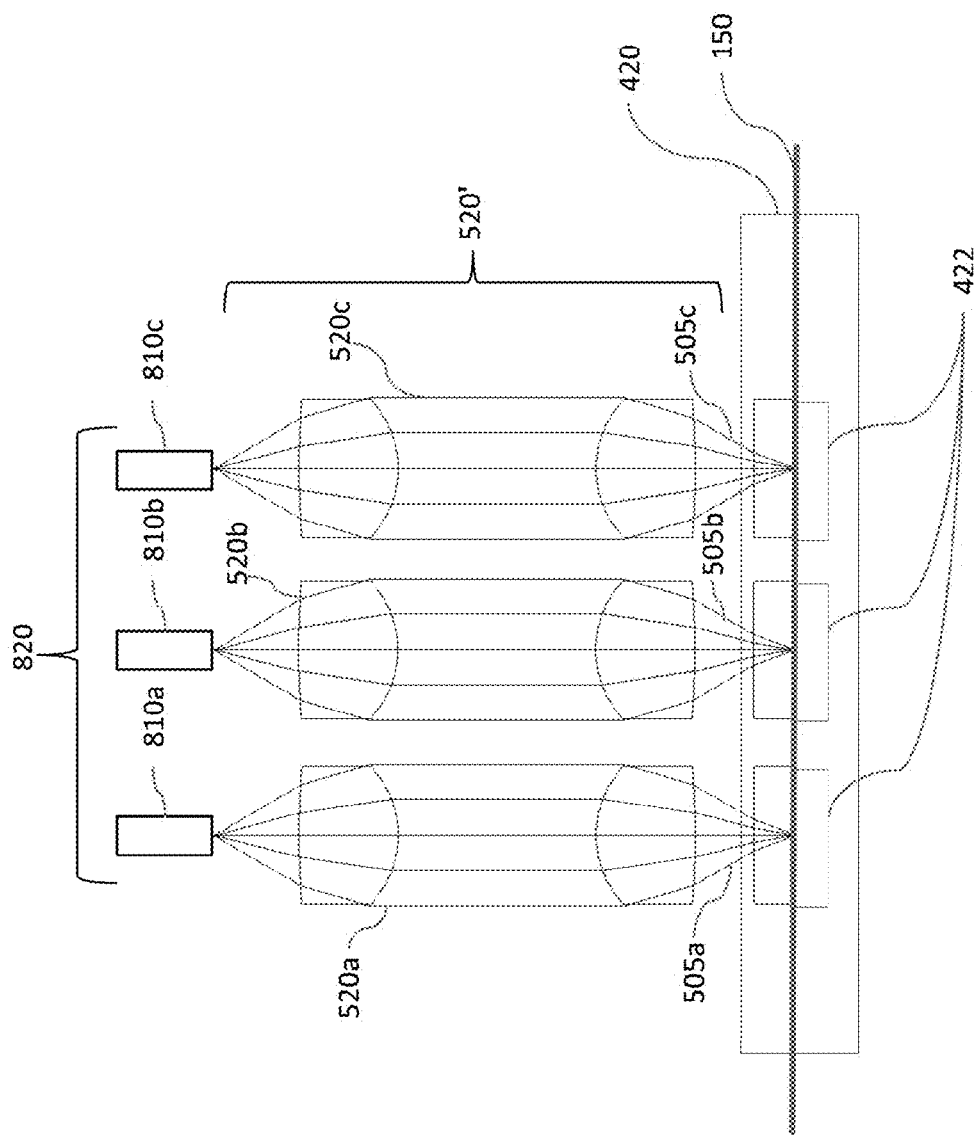

An example of an arrayed lens system 520' is schematically illustrated in FIG. 1J. In this embodiment, the three individual lens systems 520a, 520b, 520c are illustrated as being identical and arranged in parallel. Further, there is shown a one-to-one association between emission signals 505a, 505b, 505c and lens systems 520a, 520b, 520c. In other embodiments, the individual lens systems need not be identical, need not be arranged in parallel, and need not have one-to-one correspondence between the emission signals and the lens systems. Further, in this embodiment, the signal detection system 800 is illustrated as an array of detectors 820. This particular array of detectors 820 is shown as including three individual detectors 810a, 810b, 810c which are arranged in parallel and which have a one-to-one association between emission signals 505a, 505b, 505c, lens systems 520a, 520b, 520c and detector 810a, 810b, 810c. In general, the individual detectors need not be identical, need not be arranged in parallel, and need not have one-to-one correspondence between the emission signals and/or the lens systems with the detectors. As compared to a single lens system, an arrayed lens system eliminates or reduces the amount of overlap of the optical paths of the emission signals from the interrogation element to the detection plane. Other elements, such as filters, for example, a spatial angular filter (not shown), may be provided.

Figure 1K:
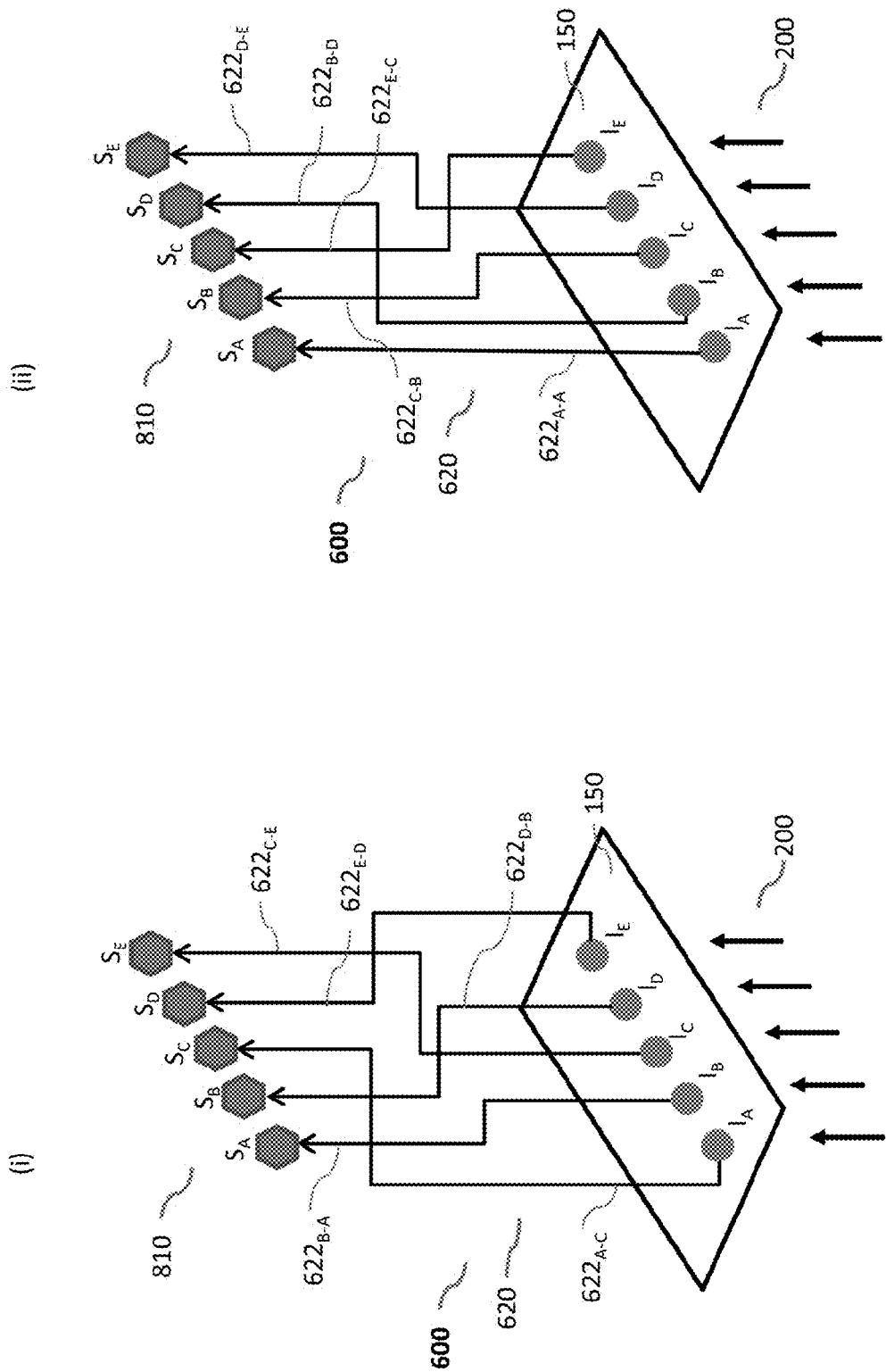

FIG. 1K schematically illustrates a system for mitigating optical crosstalk by spatially mapping signals 505 (or 515, 605, 805) onto a signal detection system 800. Specifically, an array of sensor elements $S_A$, $S_B$, $S_C$, etc. may be associated with an array of interrogation sites $I_A$, $I_B$, $I_C$, etc. in interrogation element 150 such that the spatial mapping of the array of sensor elements $S_A$, $S_B$, $S_C$, etc. is scrambled with respect to the array of interrogation sites $I_A$, $I_B$, $I_C$, etc. In other words, although a one-to-one mapping may exist between any individual particle interrogation site I and a sensor element S, the mapping is scrambled such that signals from any two neighboring interrogation sites I are more randomly dispersed among the sensor elements and are not necessarily detected by any two adjacent sensor elements. FIG. 1K provides two example scrambled spatial mapping schemes for a linear array of interrogation sites I and a linear array of sensor elements S. Referring to FIG. 1K(i), interrogation site $I_A$ is mapped to sensor element $S_C$; interrogation site $I_B$ is mapped to sensor element $S_A$; interrogation site $I_C$ is mapped to sensor element $S_E$; etc. Although linear arrays are shown in these two examples, two-dimensional or three-dimensional arrays may be employed. Further, temporal mapping (i.e., a time dimension) may be employed to further isolate neighboring emission signals from neighboring sensors. Even further, spatial mapping may employ non-scrambled or scrambled mapping with unused sensors (i.e., unmapped sensors) surrounding and/or spatially separating the active, mapped sensors.

As shown in FIG. 1K, according to certain embodiments, spatially scrambled light mapping may be achieved by using an optical fiber bundle 620 in a signal relay system 600 as part of the optical path between the interrogation sites $I_A$, $I_B$, $I_C$, etc. and the array of sensor elements $S_A$, $S_B$, $S_C$, etc. For example, in FIG. 1K(ii), optical fiber $622_{A-A}$ maps interrogation site $I_A$ to sensor element $S_A$; optical fiber $622_{B-D}$ maps interrogation site $I_B$ to sensor element $S_D$; optical fiber $622_{C-B}$ maps interrogation site $I_C$ to sensor element $S_B$; etc. Light mapping may be achieved using optical fibers or other optical elements (including reflective, refractive, diffractive, etc.).

Figure 1L:
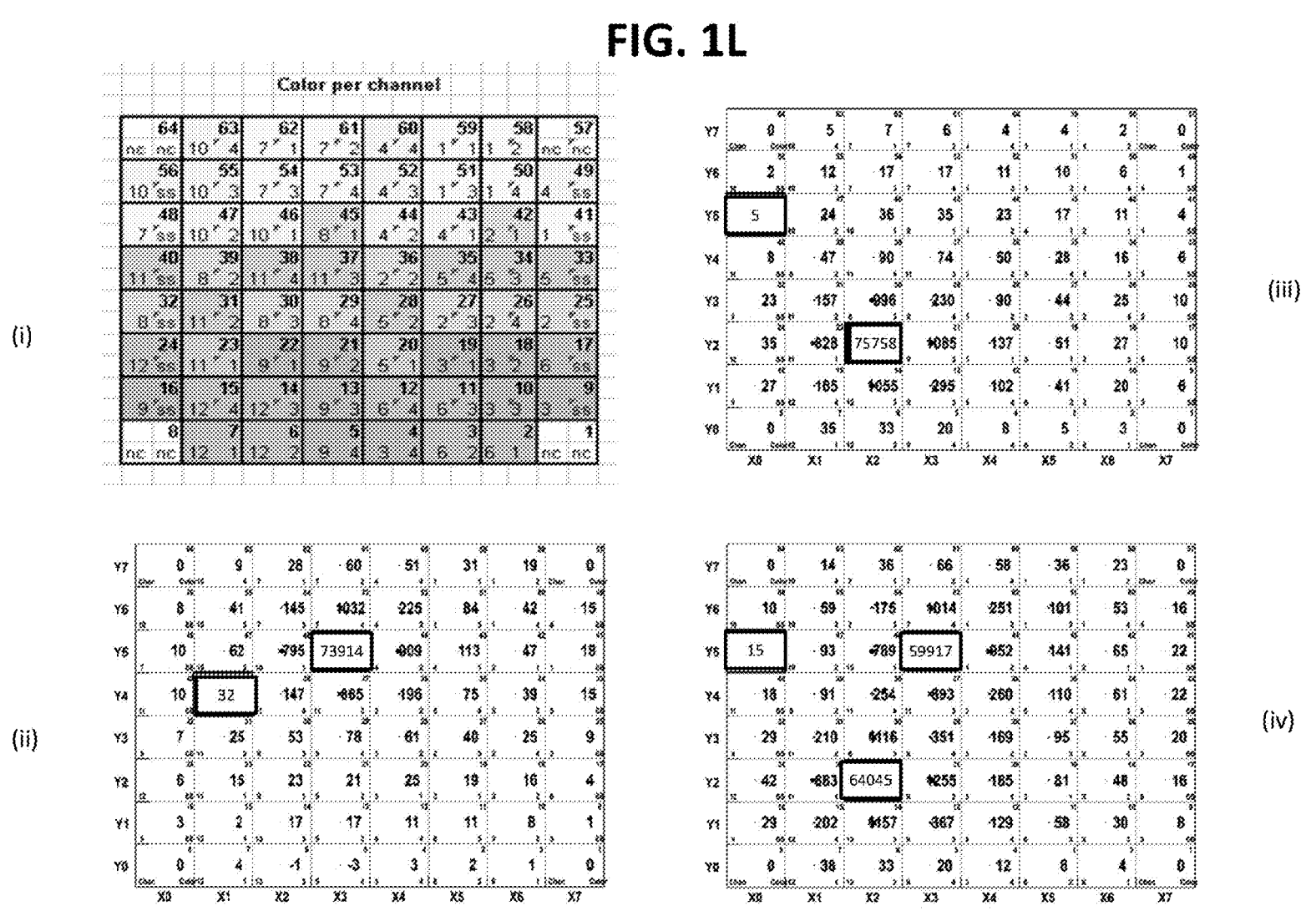

In FIG. 1L, schematic illustrations of an eight-by-eight optical sensor array are shown. FIG. 1L(i) shows the spatial mapping scheme. Sixty-four sensors form a two-dimensional array and are numbered across the rows, starting at the bottom right with sensor number 1 and ending at the top left with sensor number 64. The sensor number is shown in the top right corner of each sensor grid. Twelve interrogation sites (in this embodiment, twelve microfluidic flow channels) have been spatially mapped onto theses 64 sensors. Fluidic channels one through twelve are each associated with five different spectral signals (for example, four different fluorescent signals and a side scatter signal). Each channel and each spectral signal has been mapped to a sensor for a total of sixty mapped sensors (12 channels times 5 signals per channel equals sixty). In this embodiment, the four corner sensors (grids 1, 8, 57 and 64) in the sensor array are unmapped. Each grid is correspondingly numbered with the associated channel identifier (in the lower left corner of the grid) and the associated signal identifier (in the lower right corner of the grid). Thus, for example, sensor number 2 is located in the lower row, second from the right and this sensor is mapped to channel 6 and fluorescent signal 1. Sensor 40 is located in the far left column, fifth row from the bottom. This sensor is mapped to channel 11 and to a side scatter (ss) signal. In FIG. 1L(i), each channel is assigned a color code so that the spatial mapping of each channel is visually apparent. For example, channel 1 has been mapped to grids 41, 50, 51, 58 and 59 in the upper right region of the sensor array and channel 12 has been mapped to grids 6, 7, 14, 15 and 24 in the lower left region of the sensor array.

FIGS. 1L(ii), (iii) and (iv) show the signal levels detected for each of the sensors for three different events. In FIG. 1L(ii), a fluorescent signal 1 for a particle in microfluidic channel 8 has been detected. Sensor 45, shown highlighted, has been mapped to channel 8 and fluorescent signal 1. As shown in FIG. 1L(ii), this sensor detects an intensity of 73914. Neighboring sensors have non-zero detector values ranging from 145 to 1032. These non-zero detector values indicate spatial cross-talk occurring across neighboring sensors. However, sensor elements for the neighboring fluidic channels (7 and 9) for the same spectral signal (1) (i.e., sensor grids 62 and 22, respectively) register relatively low detector values (28 and 23, respectively). In FIG. 1L(iii), a fluorescent signal 1 for a particle in microfluidic channel 9 has been detected. Sensor 22, shown highlighted, has been mapped to channel 9 and fluorescent signal 1. As shown in FIG. 1L(iii), this sensor detects an intensity of 75958. Neighboring sensors have non-zero detector values ranging from 165 to 1085. These non-zero detector values indicate spatial cross-talk occurring across neighboring sensors. However, sensor elements for the neighboring fluidic channels (8 and 10) for the same spectral signal (1) (i.e., sensor grids 45 and 46, respectively) register relatively low detector values (35 and 36, respectively). In FIG. 1L(iv), a fluorescent signal 1 for a particle in microfluidic channel 8 has been detected and a fluorescent signal 1 for a particle in microfluidic channel 9 has been simultaneously detected. Sensor 45 (channel 8, signal 1), shown highlighted, detects an intensity of 59917; sensor 22 (channel 9, signal 1), shown highlighted, detects an intensity of 64045. These detected intensity values are significantly greater than values that would have been expected due to crosstalk alone (as determined from (ii) and (iii)), and thus, it can be reliably determined that simultaneous events occurred in these neighboring channels. Further, the measured intensities are substantially free of crosstalk noise and the actual detected values may be relied upon.

According to another aspect, FIG. 1M schematically illustrates that optical crosstalk may be mitigated by spectrally mapping signals 505 (or 515, 605, 805) onto the signal detection system 800. The signal paths may be scrambled or interwoven to minimize the amount of spectral content from adjacent interrogation sites $I_A$, $I_B$, etc. reaching adjacent (or near adjacent) sensor elements $S_A$, $S_B$, $S_C$, etc. and/or to minimize any overlap in spectral signals from any given event at an interrogation site I reaching adjacent (or near adjacent) sensors elements $S_A$, $S_B$, $S_C$, etc. According to certain embodiments, scrambling may be achieved using optical filters or other spectral selection elements 730 to isolate the spectral signals 705. Optical fibers 622 (or other optical elements) may be used to steer or direct the spectral signals 705 to specific sensors elements $S_A$, $S_B$, $S_C$, etc. Focusing elements (not shown) may be provided between the spectrally mapped signals and the sensor elements.

For example, referring to FIG. 1M, a particle may be interrogated at site $I_A$ thereby emitting signal 505a. This signal may be collected and filtered according to its spectral content, e.g. according to its fluorescent characteristics, into an array of spectral signals $705_{A1}$, $705_{A2}$, $705_{A3}$, $705_{A4}$, etc. According to some embodiments, other signals such as a side scatter signal, a forward scatter signal, an extinction signal, etc., associated with the same particle or interrogation event and may also be included in the array of "spectral" signals 705. Thus, in a general sense, an array of "spectral" signals may include any signal associated with a specific interrogation event. The array of sensor elements $S_A$, $S_B$, $S_C$, etc. may be associated with the array of spectral signals $705_{A1}$, $705_{A2}$, $705_{A3}$, etc. on a one-to-one basis such that the spectral mapping of the array of sensor elements $S_A$, $S_B$, $S_C$, etc. is scrambled with respect to the array of spectral signals $705_{A1}$, $705_{A2}$, $705_{A3}$, etc. In other words, although a one-to-one correspondence may exist between any individual particle interrogation site I and a sensor element S, the mapping is scrambled such that signals from any given event may be more randomly dispersed among the sensor elements. Further, the spectral mapping of the array of sensor elements $S_A$, $S_B$, $S_C$, etc. may be scrambled with respect to the array of spectral signals $705_{A1}$, $705_{A2}$, $705_{A3}$, etc. and also with respect to the array of interrogation sites $I_A$, $I_B$, $I_C$, etc.

FIG. 1M provides an example scrambled spectral mapping scheme for a linear array of interrogation sites I, linear arrays of spectral signals 705 and a linear array of sensor elements S. Thus, for example, a spectral signal $705_{A1}$ associated with an event at interrogation site $I_A$ is mapped to sensor element $S_A$; a spectral signal $705_{A2}$ associated with the same event at interrogation site $I_A$ is mapped to sensor element $S_C$; spectral signal $705_{A3}$ is mapped to sensor element $S_E$; etc. A spectral signal $705_{B1}$ associated with an event at interrogation site $I_B$ is mapped to sensor element $S_G$; a spectral signal $705_{B2}$ associated with the same event at interrogation site $I_B$ is mapped to sensor element $S_E$; spectral signal $705_{B3}$ is mapped to sensor element $S_D$; etc. As with the spatial mapping described above, although linear arrays are shown in these examples, two-dimensional or three-dimensional arrays may be employed. An optical fiber bundle 620 in a signal relay system 600 may provide at least part of the optical path between the interrogation sites $I_A$, $I_B$, etc. and the array of sensor elements $S_A$, $S_B$, $S_C$, etc. Optionally, mapping may be achieved using other optical elements (including reflective, refractive, diffractive, etc.).

Figure 1N:
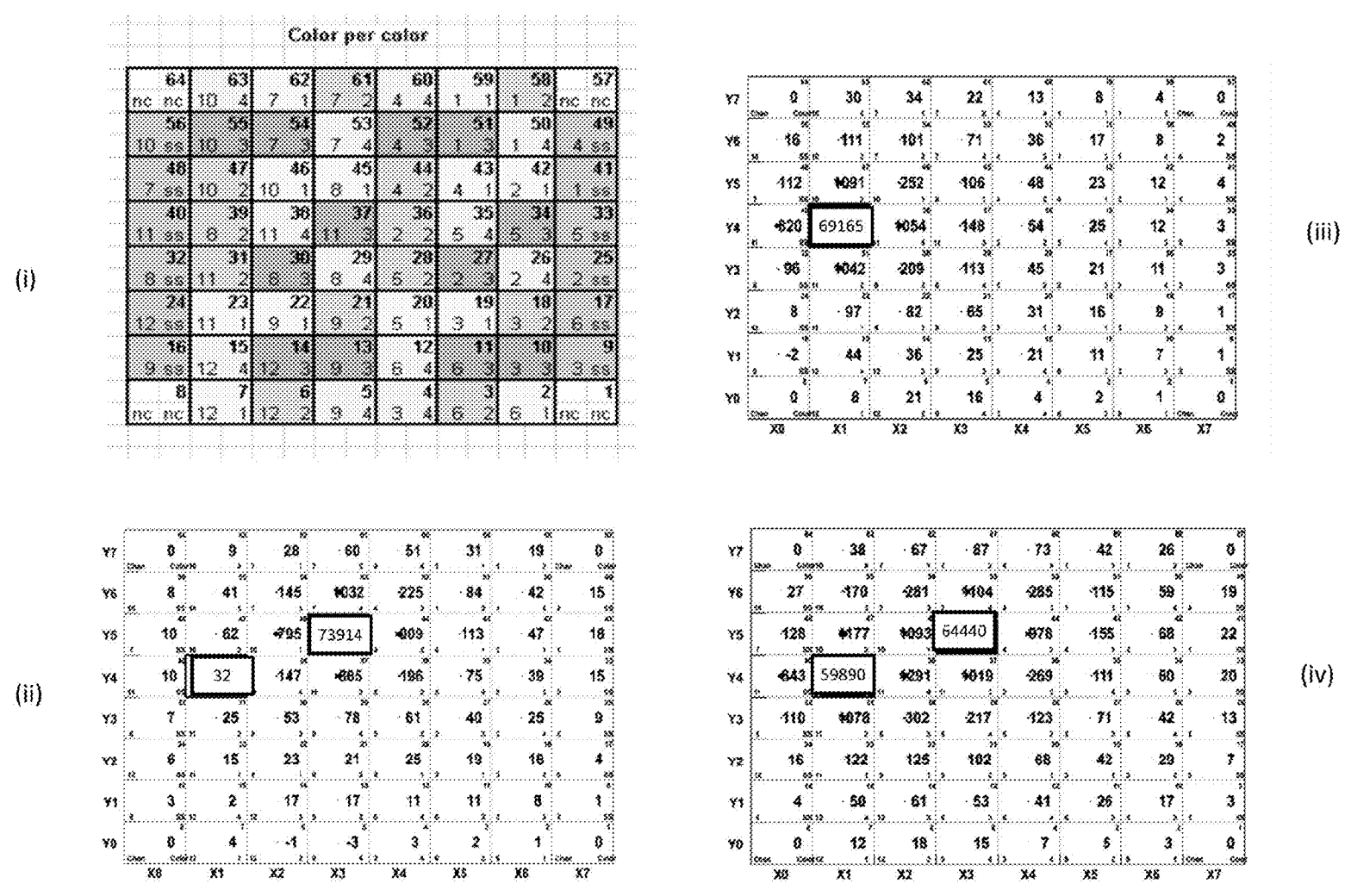

In FIG. 1N, schematic illustrations of an eight-by-eight optical sensor array are shown similar to the illustrations of FIG. 1L. FIG. 1N(i) shows the spatial mapping scheme of twelve interrogation sites and five spectral signals per site being mapped to sixty-four sensors provided in a two-dimensional array. For ease of explanation, in this embodiment the specific mapping scheme is the same as that shown in FIG. 1L. In FIG. 1N(i), each spectral signal is assigned a color code so that the spectral mapping is visually apparent. For example, spectral signals 1 have been mapped to grids 2, 7, 19, 20, 22, 23, 42, 43, 45, 46, 59 and 62 of the sensor array. Each of these mapped spectral signals corresponds to a different interrogation site (e.g., a different microfluidic channel). Spectral signals 3 have been mapped to grids 10, 11, 13, 14, 27, 30, 34, 37, 51, 52, 54 and 55 of the sensor array.

FIGS. 1N(ii), (iii) and (iv) show the signal levels detected for each of the sensors for three different events. In FIG. 1N (ii), a fluorescent signal 1 for a particle event in microfluidic channel 8 has been detected by sensor 45, shown highlighted, as having an intensity of 73914. Neighboring sensors have non-zero detector values ranging from 145 to 1032. These non-zero detector values indicate cross-talk occurring across neighboring sensors. However, sensor elements for the spectral signals (2, 3, 4, and ss) associated with the same interrogation site (channel 8) (i.e., sensor grids 39, 30, 29 and 32, respectively) register relatively low detector values (32, 53, 78 and 7, respectively). In FIG. 1N(iii), a fluorescent signal 2 for a particle event in microfluidic channel 8 has been detected at sensor 39, shown highlighted, as having an intensity of 69165. Neighboring sensors have non-zero detector values ranging from 96 to 1091. These non-zero detector values indicate cross-talk occurring across neighboring sensors. Sensor elements for the spectral signals (1, 3, 4, and ss) associated with the same interrogation site (channel 8) (i.e., sensor grids 45, 30, 29 and 32, respectively) register relatively low detector values (106, 209, 113 and 96, respectively). In FIG. 1N(iv), fluorescent signals 1 and 2 have been simultaneously detected for a particle event in microfluidic channel 8. Sensor 45 (channel 8, signal 1), shown highlighted, detects an intensity of 64440; sensor 39 (channel 8, signal 2), shown highlighted, detects an intensity of 59890. These detected intensity values are significantly greater than values that would have been expected due to crosstalk alone (as determined from (ii) and (iii)), and thus, it can be reliably determined that the measured intensities are substantially free of crosstalk noise and the actual detected values may be relied upon.

FIG. 1O schematically illustrates a system for mitigating optical crosstalk by spatially and spectrally mapping signals 515 onto a detector array within a signal detection system 800. Specifically, an array of sensor elements $S_A$, $S_B$, $S_C$, etc. may be associated with an array of interrogation sites $I_A$, $I_B$, $I_C$, etc. in interrogation element 150 such that the spatial mapping of the array of sensor elements $S_A$, $S_B$, $S_C$, etc. is scrambled with respect to the array of interrogation sites $I_A$, $I_B$, $I_C$, etc. Further, the array of sensor elements $S_A$, $S_B$, $S_C$, etc. may be associated with the array of spectral signals $705_{A1}$, $705_{A2}$, $705_{A3}$, etc. on a one-to-one basis such that the spectral mapping of the array of sensor elements $S_A$, $S_B$, $S_C$, etc. is scrambled with respect to the array of spectral signals $705_{A1}$, $705_{A2}$, $705_{A3}$, etc. Referring to FIG. 1O, a radiation source 200 may be spatially filter via mask 410 having apertures 412a-412f. Each aperture 412 is associated with an interrogation site IA-IE (e.g., a microfluidic channel) in the detection plane 150. The apertures may be of the same or different sizes. Further, in some embodiments a plurality of apertures may be associated with an interrogation site. This plurality of apertures may form a pattern that may assist in the evaluation of the emitted signals and/or that may contain information about the interrogation site itself.

A single lens systems 520 collects emission signals 505 from the plurality of interrogation sites. Collection signals 515 may be focused at focal plane 516. A spatial filter 710 having apertures 712a-712e coincident with focal plane 516 allows signals 515 to be transmitted to fiber bundle 620. Fiber bundle 620 may spatially and/or spectrally scramble and map signals A, B, C, etc. to sensors $S_A$, $S_B$, $S_C$, etc.

Specific embodiments of the features described above will now be described in conjunction with various particle processing systems 100 in accordance with aspects presented herein.

FIG. 2 illustrates a specific embodiment of a portion of a particle processing system 100 that may be provided to minimize crosstalk. In this embodiment, the emission signal collection system 500 includes a single lens system 520 provided as an optical column 550 with a spatial filter 510 and/or a spectral filter. For this particular embodiment, the spatial filter 510 may be an image plane confocal aperture system. Signal conditioning system 700 includes a spectral filter, for example, a dichroic block array 720. Signal detection system 800 is provided as a detector array 820. Signal relay system 600 is provided as a spatially and/or spectrally scrambled bundle of fiber optics 620. As noted above and referring also to FIG. 1A, the signal relay system 600 may be provided before or after the signal conditioning system 700.

FIG. 3A schematically illustrates a particle processing system 100a according to another aspect. Similar to particle processing system 100 illustrated in FIG. 1A, particle processing system 100a may include a radiation source system 200, a radiation beam control system 300a, a particle processing region 400, an emission radiation signal collection system 500, a signal relay system 600, a signal conditioning system 700 (which may include a dichroic array), a signal detection system 800, and an electronics system 900. In this particular embodiment, radiation source system 200 includes one or more radiation sources 210 that emit a beam of electromagnetic radiation 205. Beam 205 is transmitted to a set of beam shaping optics 220 via a plurality of mirrors 211. The shaped beam 205 is then transmitted to a radiation beam control system 300a. As with the embodiment described in FIG. 1A interrogation beam 215 is used to illuminate portions of the detection plane 150, which may be provided within particle processing region 400. Emission signals 505 are emitted from the interrogation element 150 (e.g., due to particles being interrogated by the interrogation beam 215), collected by emission signal collection system 500 and transmitted to signal detection system 800 via a signal relay system 600 and/or a signal conditioning system 700.

Signal detection system 800 receives detector input signals 805 and converts these into electrical signals 905 for transmission to electronics 900. The signal detection system 800 may include a single sensor (or detector) 810 or a plurality of sensors (or detectors). For example, a single detector may be provided one-to-one for each spectral signal for each interrogation site (e.g., for each microfluidic channel, well, etc.); a single detector may be provided one-to-one for each interrogation site; a single detector may be provided for a plurality of interrogation sites; a single detector may be provided for each spectral domain (i.e., color) across a plurality of interrogation site, etc.

In this particular embodiment, the radiation beam control system 300a may include an optical scanner 320, a mirror 311, and a segmented mirror 313. Optical scanner 320 is provided with an angular scanning capability for scanning over an angular range α. An optical scanner may be provided by, for example, a galvanic mirror, an electro-optical scanner, an acousto-optical scanner, etc. A segmented mirror 313 suitable for use in this embodiment has been described in U.S. Pat. No. 7,298,478 issued Aug. 18, 2009 to Gilbert et al., the contents of which are incorporated by reference herein in their entirety. In other embodiments, other or different optical elements may be included in the radiation beam control system's optical path (e.g. free space optics such as refractive, reflective, diffractive, etc. elements and/or fiber optics and/or waveguides).

During the course of a single scan, optical scanner 320 directs interrogation beam 215 along interrogation beam path 215a, then along interrogation beam path 215b, then along interrogation beam path 215c, etc. Each interrogation beam path 215a, 215b, 215c, etc. is associated with a segment of segmented mirror 313, which in turn is associated with an interrogation site in the detection plane 150. Thus, for example, when optical scanner 320 directs interrogation beam 215 along interrogation beam path 215a, particles within microfluidic channel 422a may be illuminated.

Figure 3B:
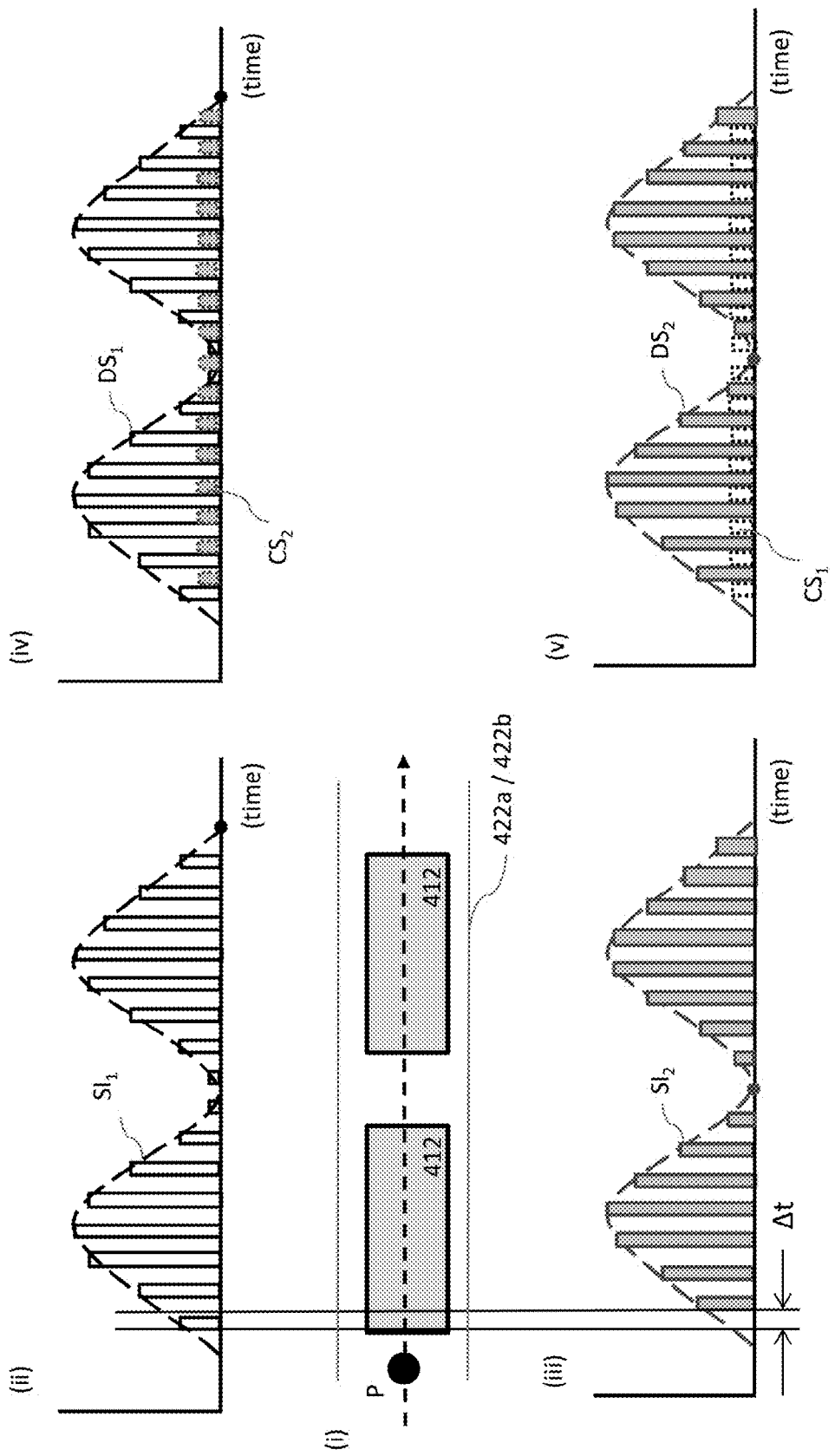

FIG. 3B illustrates how scan illumination may be used to reduce and/or account for optical crosstalk in the signal received by the signal detection system 800 when a single detector is provided per interrogation site per spectral domain (i.e., color). FIG. 3B illustrates idealized timing diagrams for scanning and detection of particles flowing within first and second microfluidic channels, wherein the optical scanner 320 scans between the first and second channels. (Although shown for explanation purposes with respect to only two channels in FIG. 3B, the particle processing system 100a may generally include any number of interrogation sites.) FIG. 3B(i) schematically illustrates a particle P flowing along a flow axis within either the first or the second microfluidic channel. In this embodiment, regions of the flow are configured to be illuminated via apertures 412. FIG. 3B(ii) illustrates a typical scan illumination pattern $SI_1$ (intensity versus time) as may be applied to a first microfluidic channel; FIG. 3B(iii) illustrates a typical scan illumination pattern $SI_2$ as may be applied to a second microfluidic channel. As the particle P flows within the aperture region 412 it is illuminated multiple times as the optical scanner 320 directs the interrogation beam across the plurality of channels. Typically, the footprint (not shown) of the interrogation beam 215 extends over the entire aperture region. The pulse delay between the interrogation beam 215 scanning the first channel (see (ii)) and then scanning the second channel (see (iii)) is shown as Δt.

FIG. 3B(iv) illustrates a typical detected signal $DS_1$ pattern as may be detected by a first detector associated with a particle traveling along the first microfluidic channel (or residing within a first interrogation site); FIG. 3B(v) illustrates a typical detected signal $DS_2$ pattern as may be detected by a second detector associated with a particle traveling along the second microfluidic channel (or residing within a second interrogation site). Specifically, FIG. 3B(iv) illustrates that the detector senses the detected signal $DS_1$ due to the particle traveling within the first channel and also may sense a crosstalk signal $CS_2$ due stray signals emanating from the second channel. However, due to the pulse delay Δt experienced as the interrogation beam 215 scans the first channel and then scans the second channel, any crosstalk signals $CS_2$ detected by the first detector that are associated with scanning of the second microfluidic channel (see (iii)) will be out-of-phase with the signal emanating from the first microfluidic channel (see (ii)). Similarly, referring to FIG. 3B(v) any crosstalk signals $CS_1$ detected by the second detector that are associated with scanning of the first microfluidic channel (see (ii)) will be out-of-phase with the detected signal $DS_2$ emanating from second microfluidic channel (see (iii)). Thus, in-phase signals due to the detection of a particle within the scanned channel may be isolated from the out-of-phase crosstalk signals due to adjacent channels being scanned.

Figure 3C:
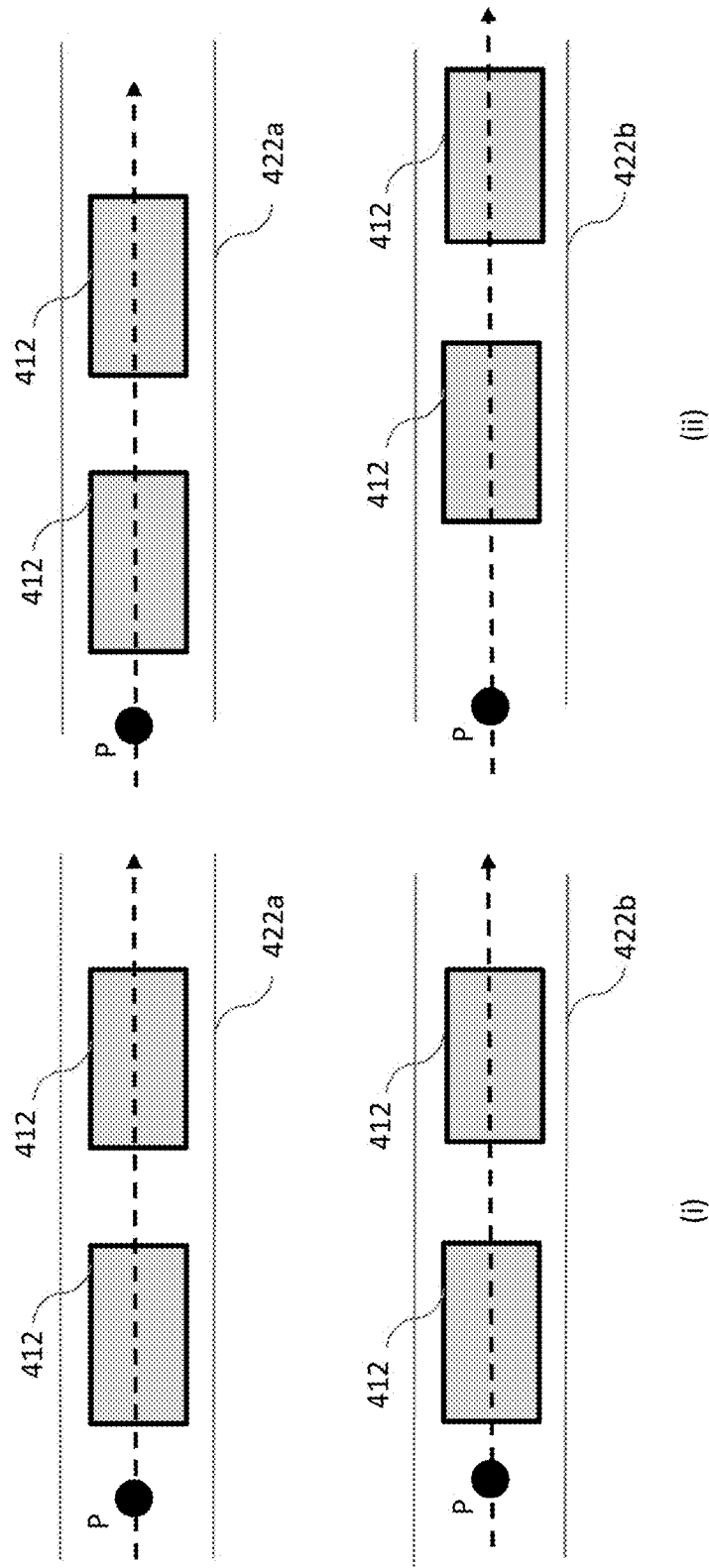

In the above embodiment, the illumination or excitation apertures or pinholes 412 of the plurality of channels were assumed to be aligned with one another along the longitudinal lengths of the channels. In other words, as shown in FIG. 3C(i), the apertures 412 of a first channel 422a are positioned side-by-side with the apertures 412 of the second channel 422b. In another embodiment, referring to FIG. 3C(ii), the illumination or excitation apertures 412 need not be aligned, but may be relatively staggered along the longitudinal lengths of the channels 422a, 422b. A staggered aperture pattern may further reduce optical crosstalk at the illumination stage.

Figure 3D:
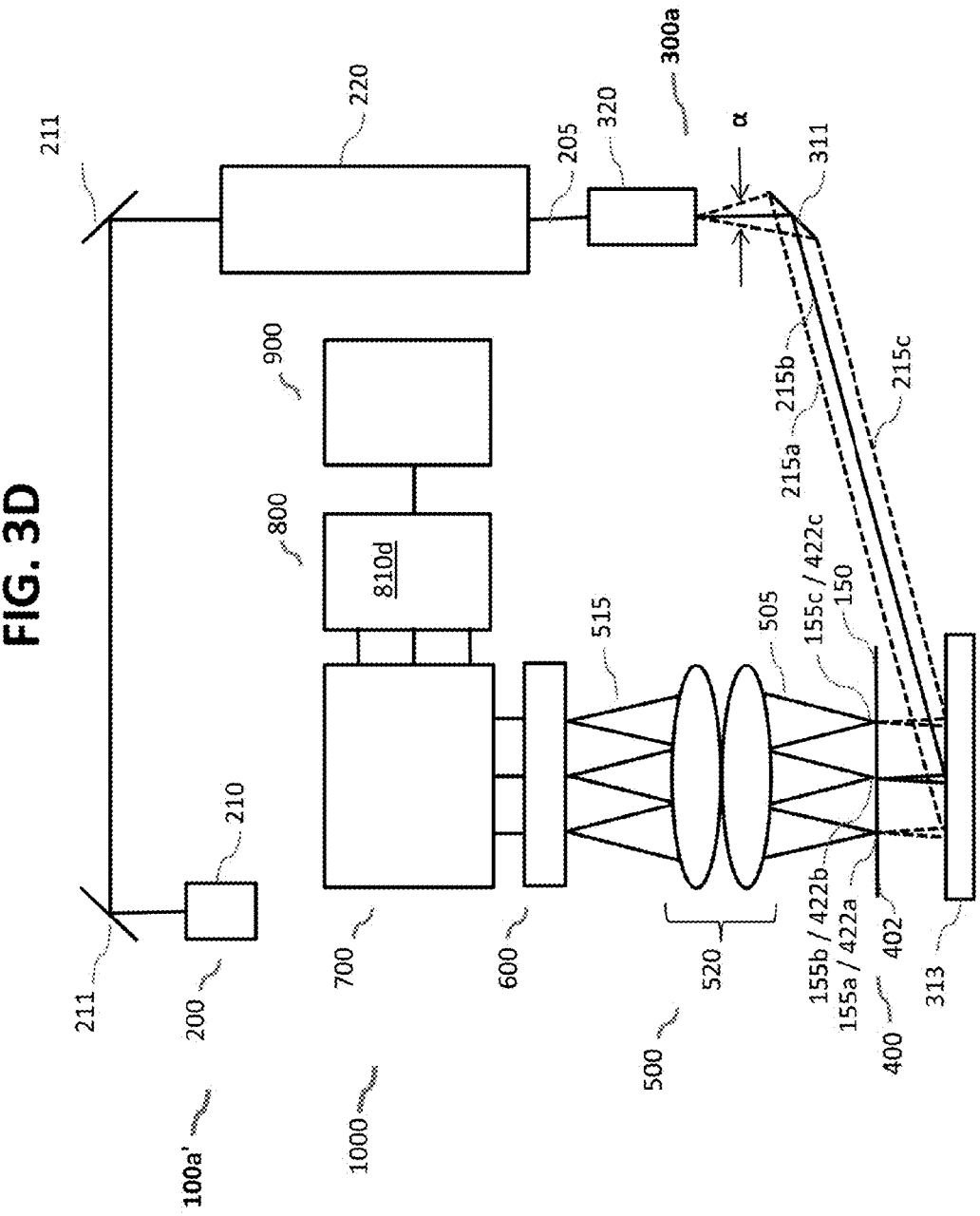

FIG. 3D schematically illustrates another embodiment of particle processing system 100a' wherein the plurality of detectors 810a, 810b, 810c, etc. have been replaced with a single detector 810d. Detector 810d is configured to receive signals from a plurality of interrogation sites 155a, 155b, 155c, etc. for a single spectral or polarization domain (i.e., color).

Figure 3E:
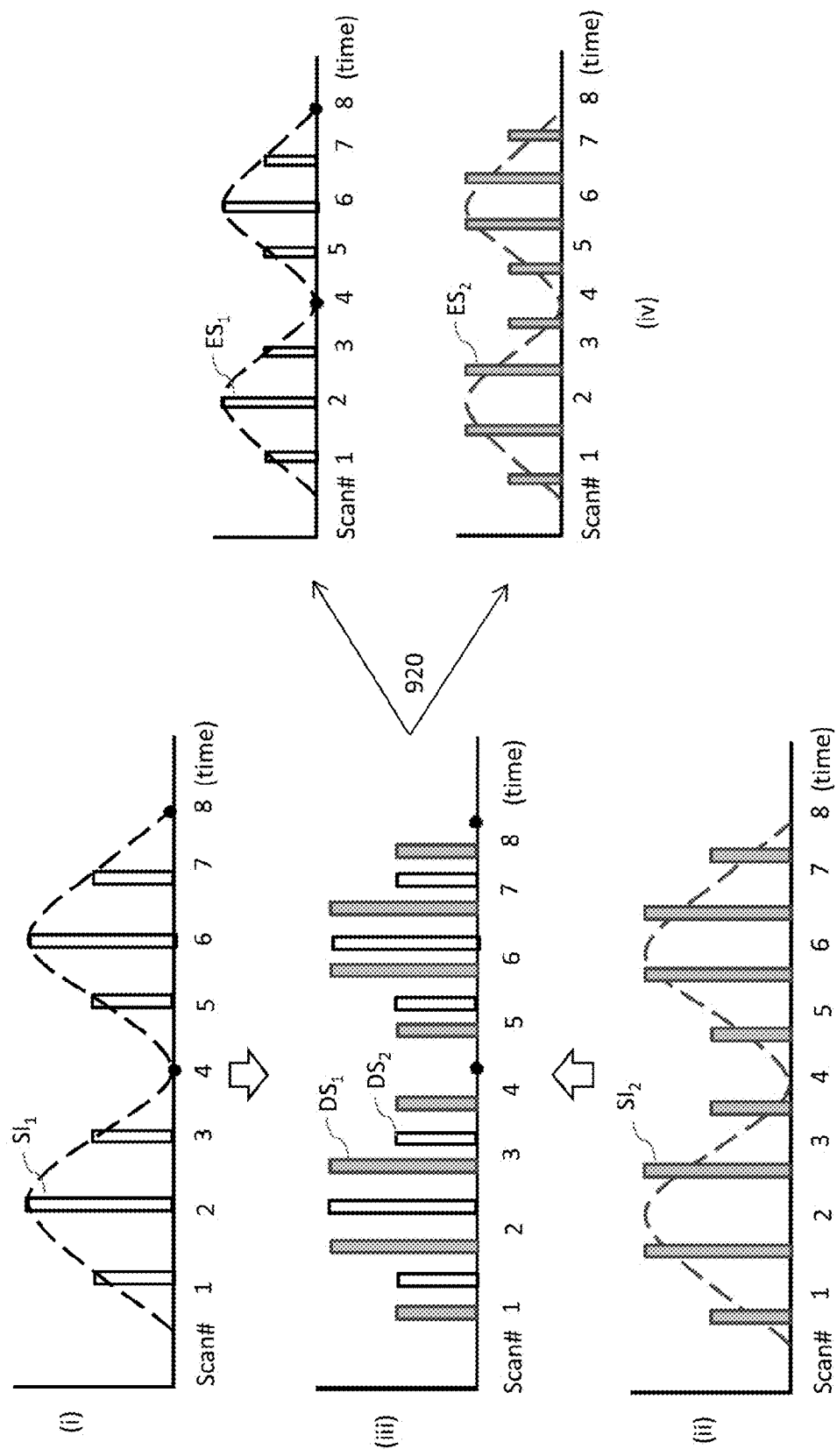

FIG. 3E illustrates how scan illumination may be used to reduce and/or account for optical crosstalk in the signal received by the signal detection system 800 when the single detector 810d as shown in FIG. 3D is configured to receive the signals from a plurality of interrogation sites 155a, 155b, 155c, etc. for a single spectral domain (i.e., color). For example, in the context of a particle processing region 400, FIG. 3E illustrates idealized timing diagrams for scanning and detection of particles flowing within first and second microfluidic channels 422a, 422b, wherein the optical scanner 320 scans between the first and second channels. As described above with respect to FIG. 3B(i), a particle P may travel along a flow axis within either the first or the second microfluidic channel 422a, 422l and regions of the flow are configured to be illuminated via apertures 412. FIG. 3E(i) illustrates a typical scan illumination pattern $SI_1$ (intensity versus time) as may be applied to a first microfluidic channel 422a; FIG. 3E(ii) illustrates a typical scan illumination $SI_2$ pattern as may be applied to a second microfluidic channel 422b. FIG. 3E(iii) illustrates a typical detected signal $DS_1$ pattern as may be detected by the single detector for a first particle traveling along the first microfluidic channel 422a and a second particle simultaneously traveling along the second microfluidic channel 422b. The detected signals $DS_1$ due to the scanning pulses interrogating the first channel and the detected signals $DS_2$ due to the scanning pulses interrogating the second channel are alternatively received (interleaved) by the detector 810d. Given a known scanning pulse delay Δt, and referring to FIG. 3E(iv), these interleaved signals may be electronically separated (for example, using a demultiplexer 920) into electronic signals $ES_1$ that represent the event in the first channel and electronic signals $ES_2$ that represent the event in the second channel.

Figure 4:
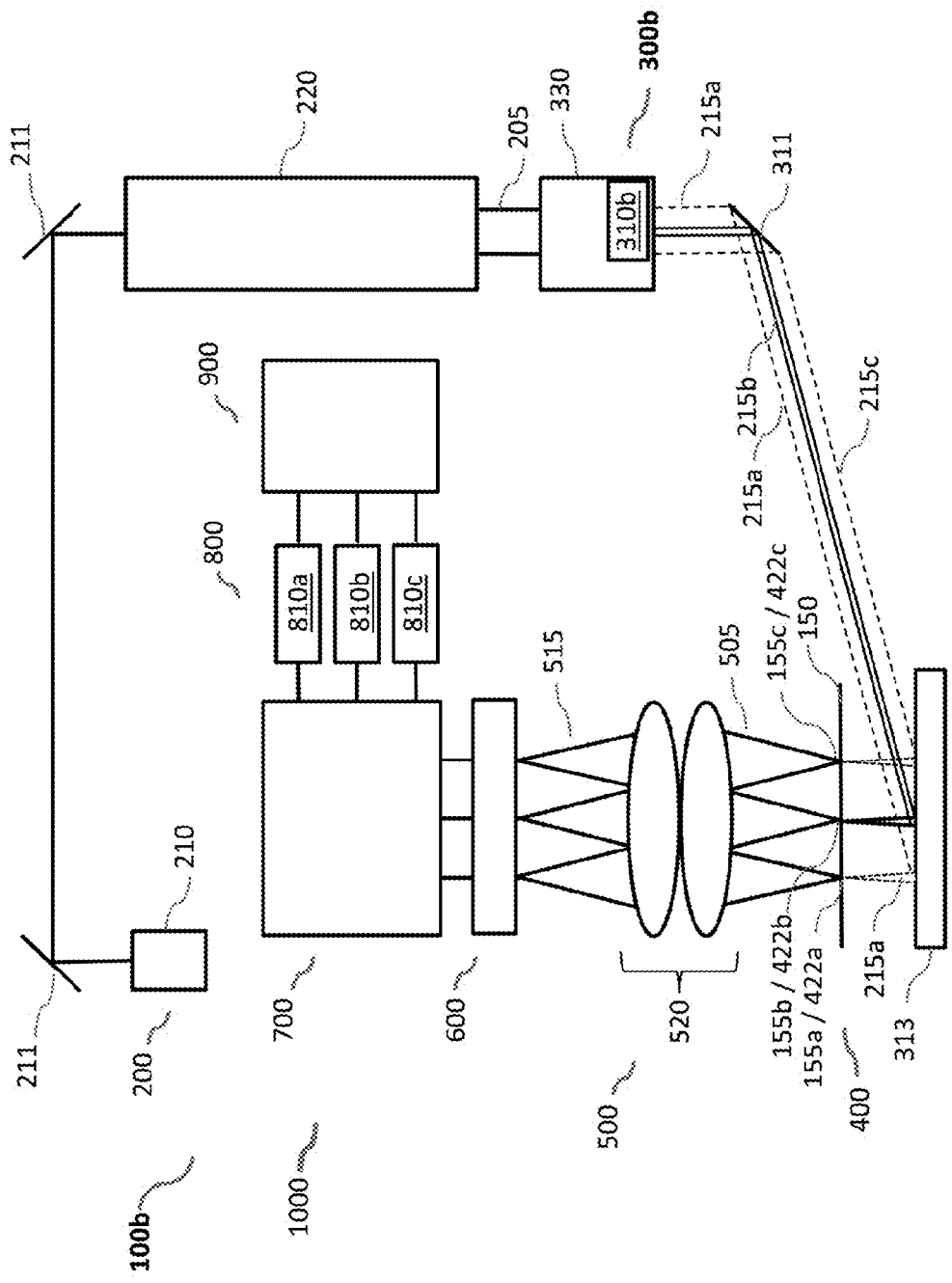
FIG. 4 depicts another exemplary particle processing systems, methods and data according to the present disclosure.

FIG. 4 schematically illustrates a particle processing system 100b according to another aspect. Specifically, FIG. 4 illustrates an embodiment of a particle processing system provided with a scan blocker across the illumination source. Similar to particle processing system 100a illustrated in FIG. 3A, particle processing system 100b may include a radiation source system 200, a radiation beam control system 300b, a particle processing region 400, an emission signal collection system 500, a signal relay system 600, a signal conditioning system 700, an signal detection system 800 and an electronics system 900. In this particular embodiment, the radiation beam control system 300b includes an illumination beam spatial modulator 330 (rather than the optical scanner 320 included in FIGS. 3A and 3D). Illumination beam spatial modulator 330 may include a spatial filter 310b. Spatial filter 310b allows one or more portions of the radiation beam 205 to propagate to the detection plane 150, while blocking the remainder of the radiation beam 205. Those portions of the radiation beam 205 not blocked by the spatial filter 310b are provided as interrogation beams 215 that interrogate select interrogation sites 155. Spatial filter 310b may be a movable mask that is translated and/or rotated so that interrogation sites (or subsets of interrogation sites) are sequentially illuminated by the portions of the radiation beam not blocked by the spatial filter. Alternatively, or additionally, the spatial filter 310b may include one or more shutters that open and close to sequentially open or close apertures. As a non-limiting example, the spatial filter 310b may include a plurality of scanning slits, choppers, rotating chopper wheels, acousto-optic modulators (AOM), electro-optical modulators (EOM), etc. Other scanning spatial modulators as would be known to persons of ordinary skill in the art may be suitable. The segmented mirror 313 of FIGS. 3A and 3D may be included in this embodiment.

At a first instance in time, illumination beam spatial modulator 330 allows interrogation beam 215a to interrogate channel 422a, while blocking beams 215b, 215c, etc. from illuminating the detection plane 150. At a second instance in time, movable spatial filter 310b has been translated and/or rotated so that interrogation beam 215b is allowed to interrogate channel 422b, while beams 215a, 215c, etc. are blocked from illuminating the detection plane 150. Thus, each of the interrogation sites 155 may be sequentially interrogated.

The idealized timing diagrams of FIG. 3B are applicable to the particle processing system 100b of FIG. 4 when a single detector is provided per microfluidic channel per spectral domain (i.e., color). Further, the idealized timing diagrams of FIG. 3E are applicable to the particle processing system 100*b* of FIG. 4 as modified to include a single detector configured to receive signals from a plurality of interrogation sites for a single spectral domain (i.e., color) (see for example, the single detector 810*d* shown in FIG. 3D). FIGS. 3B and 3E illustrate how scanning across interrogation sites with an illumination beam spatial modulator 330 may be used to reduce and/or account for optical crosstalk in the signal received by the signal detection system 800.

Figure 5:
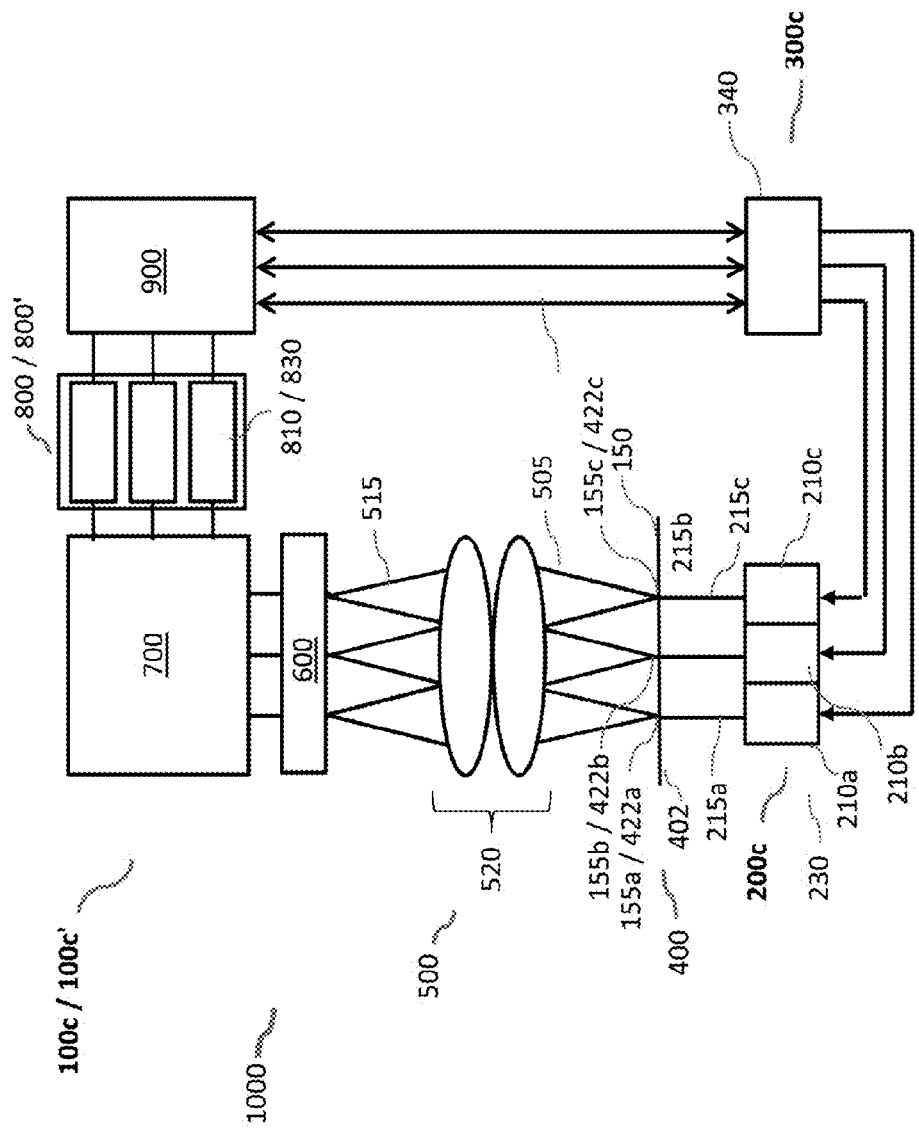
FIG. 5 depicts another exemplary particle processing systems, method and data according to the present disclosure.

FIG. 5 schematically illustrates a particle processing system 100*c* according to yet another aspect. Similar to particle processing system 100*a* illustrated in FIG. 3A, particle processing system 100*c* may include a radiation source system 200*c*, a radiation beam control system 300*c*, a particle processing region 400, an emission signal collection system 500, a signal relay system 600, a signal conditioning system 700, an signal detection system 800 and an electronics system 900. In this particular embodiment, the radiation source system 200*c* includes a pulsed illumination array 230. Pulsed illumination array 230 includes a plurality of radiation sources 210*a*, 210*b*, 210*c*, etc. that may be pulsed (i.e., turned on and turned off). The radiation sources 210*a*, 210*b*, 210*c*, etc. may be pulsed independently of one another or they may be controlled with respect to each other or with respect to a common basis. Referring to FIG. 5, each radiation source 210*a*, 210*b*, 210*c*, etc. may be associated with a single interrogation site 155*a*, 155*b*, 155*c*, etc. (as a non-limiting example, radiation source 210*a* may illuminate a detection region within a microfluidic channel 422*a*; radiation source 210*b* may illuminate a detection region within a microfluidic channel 422*b*; radiation source 210*c* may illuminate a detection region within a microfluidic channel 422*c*; etc.). Alternatively and/or additionally, radiation sources 210*a*, 210*b*, 210*c*, etc. may each be associated with a plurality of interrogation sites 155. Even further, each interrogation site 155 may be associated with a single radiation source 210 or with more than one radiation source 210.

Further, in this particular embodiment, the radiation beam control system 300*c* includes a pulse generator 340 (rather than the optical scanner 320 included in FIGS. 3A and 3D or the illumination beam spatial modulator 330 of FIG. 4). Electronics system 900 may control the pulse generator 340, which in turn controls the illumination of the interrogation sites by the pulsed radiation sources 210*a*, 210*b*, 210*c*, etc. of the pulsed illumination array 230. The pulse generator 340 may delay or stagger the pulses being generated. As a non-limiting example, a pulsed source delay timing array may be provided as [(t-t$_0$); (t-t$_1$); (t-t$_2$); etc.].

For example, the pulse delay generator 340 may control the pulse activation widths (i.e., the time over which an interrogation beam 215 is produced by the radiation source 210) of each of the radiation sources. According to one embodiment, each of the pulsed radiation sources may have identical pulse activation widths. According to another embodiment, the pulse widths need not be identical, but rather, they may differ across the plurality of radiation sources. Further, the pulse widths for any given radiation source may remain constant or they may vary.

Additionally and/or alternatively, the pulse generator 340 may control the delay time (i.e., the time between the pulse activation "on" signals being sequentially sent to the radiation sources 210*a*, 210*b*, 210*c*, etc.). A delay time between sequentially activated pulses may be equal to the pulse activation width, in which case the pulse of the first radiation source 210*a* will end at the same time that the pulse of the second radiation source 210*b* begins. Optionally, a delay time between sequentially activated pulses may be greater than the pulse activation widths, in which case there will be a break or a gap between when a first radiation source 210*a* has ended its pulse and when the second radiation source 210*b* has begun its pulse. On the other hand, a delay time between sequentially activated pulses may be less than the pulse activation widths, in which case there will be an overlap between when a first radiation source 210*a* has ended its pulse and when the second radiation source 210*b* has begun its pulse. The delay time for sequentially activating pulses may be constant, may differ and/or may vary.

According to an example embodiment, at a first instance in time t$_0$, radiation source 210*a* of pulse generator 340 is activated such that interrogation beam 215*a* illuminates channel 422*a*. While radiation source 210*a* is activated, radiation sources 210*b*, 210*c*, etc. remain off. At a second instance in time t$_1$, radiation source 210*a* is de-activated or turned off. At a third instance in time t$_2$, radiation source 210*b* of pulse generator 340 is activated. Radiation source 210*b* of pulse generator 340 may generate an interrogation beam 215*b* that illuminates channel 422*b*. At a fourth instance in time t$_3$, radiation source 210*b* is de-activated or turned off.

According to certain embodiments, radiation sources 210*a*, 210*b*, 210*c*, etc. may be sequentially spatially arranged within pulsed illumination array 230 and excitation 210*a*, 210*b*, 210*c*, etc. may be sequentially pulsed. According to other embodiments, radiation sources 210*a*, 210*b*, 210*c*, etc. may be sequentially spatially arranged within pulsed illumination array 230 and radiation sources 210*a*, 210*b*, 210*c*, etc. may be pulsed out-of-sequence (i.e., first 210*a* may be pulsed, then 210*f* may be pulsed, then 210*b* may be pulsed, then 210*e* may be pulsed, and so on). Thus, each of the interrogation sites 155 may be sequentially interrogated or, in alternative embodiments, each of the interrogation sites 155 may be more randomly illuminated or pulsed.

The idealized timing diagrams of FIG. 3B are equally applicable to the particle processing system 100*c* of FIG. 5 when a single detector is provided per microfluidic channel per spectral domain (i.e., color) and when pulsed illumination as described above (rather than scanned illumination) is applied to the interrogation sites 155. Further, the idealized timing diagrams of FIG. 3E are applicable to the particle processing system 100*c* of FIG. 5 as modified to include a single detector configured to receive signals from a plurality of interrogation sites 155 for a single spectral domain (i.e., color) (see for example, the single detector 810*d* shown in FIG. 3D) and when pulsed illumination as described above (rather than scanned illumination) is applied to the interrogation sites. Thus, FIGS. 3B and 3E also illustrate how, according to certain embodiments, pulsed interrogation of a plurality of interrogation sites 155 with a pulsed illumination array 230 and a pulse generator 340 may be used to reduce and/or account for crosstalk in the signals received by the signal detection system 800.

Figure 6A:
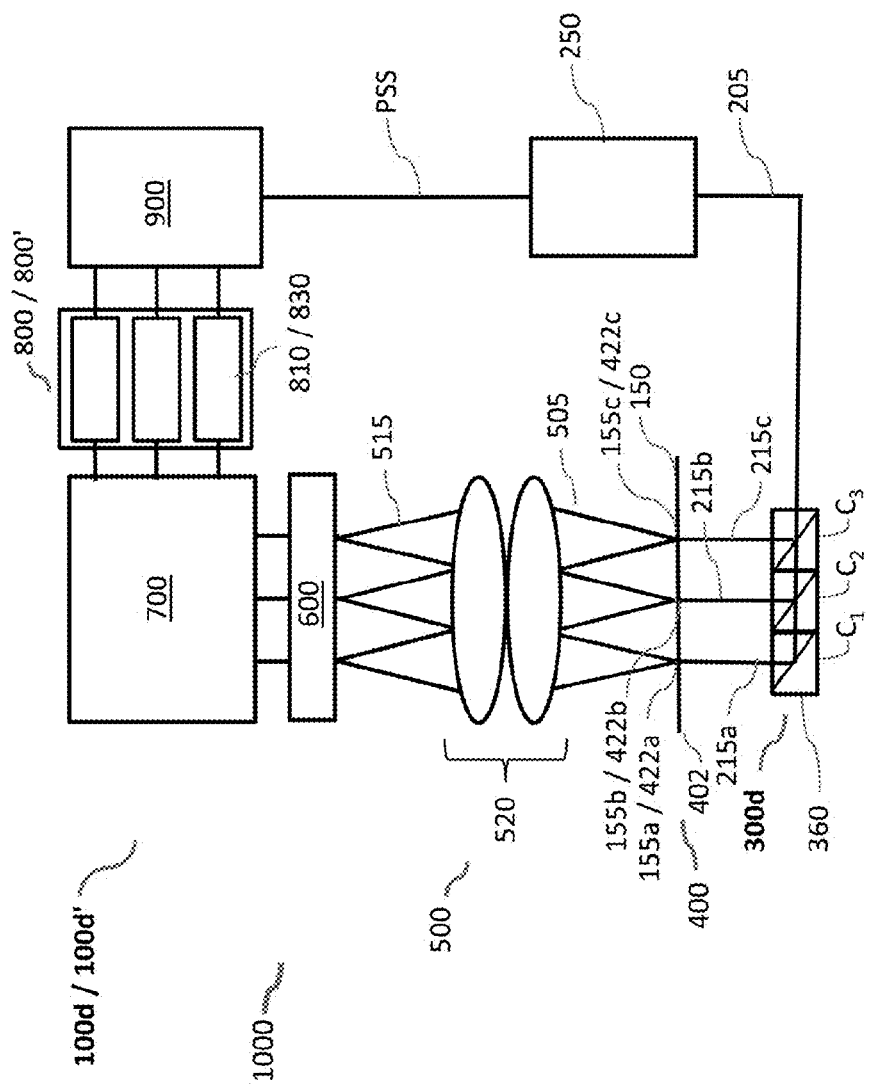
FIGS. 6A-6B depict other exemplary particle processing systems, methods and data according to the present disclosure.
Figure 6B:
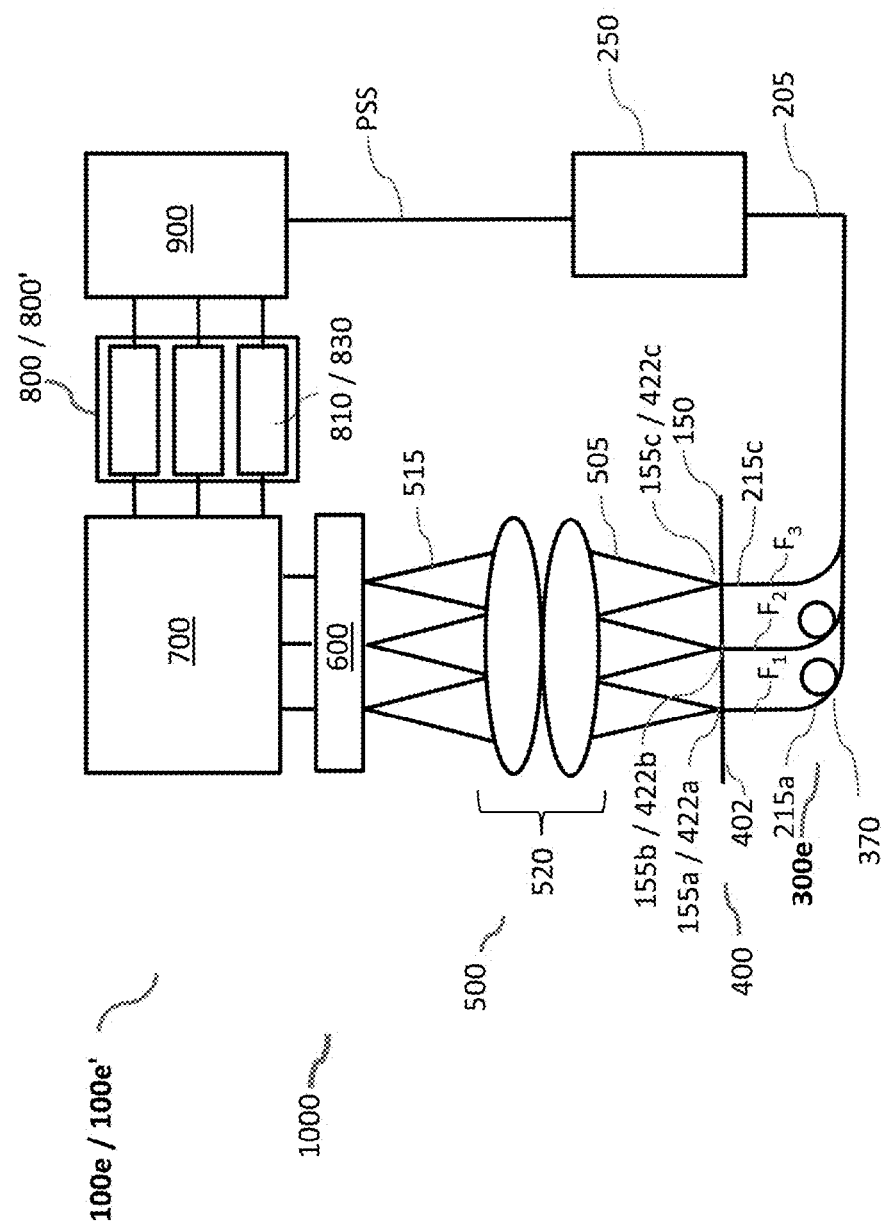

FIG. 6A and FIG. 6B show two embodiments of a particle processing system 100 that may utilize pulse discrimination with a speed of light delay. For example, in FIG. 6A a particle processing system 100*d* includes a radiation beam control system 300*d* having an array 360 of radiation beam transmission channels $C_1$, $C_2$, $C_3$, etc. Each of these transmission channels $C_1$, $C_2$, $C_3$, etc. may have differing indices of refraction ($n_1$, $n_2$, $n_3$, etc.). These differing refraction indexes result in the radiation beam 205 being transmitted at differing speeds of light, thus developing a delay in the timed delivery of the interrogation beams 215*a*, 215*b*, 215*c*, etc. between the channels. When a pulsed light source 250 is triggered (for example, via a pulse synchronization signal PSS provided by electronics system 900), a plurality of time-staggered pulsed radiation beams 215a, 215b, 215c may be produced. As one non-limiting example, the pulsed light source 250 may be provided as a pulsed or quasi-continuous-wave laser.

As another example, in FIG. 6B a particle processing system 100e includes a radiation beam control system 300e provided with an array 370 of fiber optic transmission channels $F_1$, $F_2$, $F_3$, etc. having different lengths ($l_1$, $l_2$, $l_3$, etc.). The differing lengths of the optical fibers result in differing times for transmitting the interrogation beams 215, thus, again developing a timed delay of the interrogation beams 215 to the interrogation sites. In general, an optical delay may be developed by directing the interrogation beams 215 along different paths having different lengths and/or different transmissivities. Thus, as with particle processing system 100d, when a pulsed light source 250 is triggered in particle processing system 100e, a plurality of time-staggered pulsed radiation beams 215a, 215b, 215c may be produced.

The idealized timing diagrams of FIG. 3B are also applicable to the particle processing system 100d of FIG. 6A (and also to the particle processing system 100e of FIG. 6B) when a single detector is provided per microfluidic channel per spectral domain (i.e., color) and when pulsed illumination as described above (rather than scanned illumination) is applied to the interrogation sites 155. Further, the idealized timing diagrams of FIG. 3E are applicable to the particle processing system 100d of FIG. 6A (and also to the particle processing system 100e of FIG. 6B) as modified to include a single detector configured to receive signals from a plurality of interrogation sites 155 for a single spectral domain (i.e., color) (see for example, the single detector 810d shown in FIG. 3D) and when pulsed illumination as described above (rather than scanned illumination) is applied to the interrogation sites 155. Thus, FIGS. 3B and 3E also illustrate how, according to certain embodiments, pulsed interrogation of a plurality of interrogation sites 155 using a speed of light delay to discriminate the pulses as embodied, for example, in the array 360 of refractive channels (FIG. 6A) or in the array 370 of optical fibers (FIG. 6B), may be used to reduce and/or account for optical crosstalk in the signals received by the signal detection system 800.

Referring now back to FIG. 5, a variation 100c' of particle processing system 100c is described. In the embodiment 100c discussed above, pulsed interrogation beams 215a, 215b, 215c, etc. are directed to the interrogation sites 155a, 155b, 155c, etc. of the detection plane 150. The radiation source system 200c may include a pulsed illumination array 230 which includes a plurality of radiation sources 210a, 210b, 210c, etc. that may be pulsed (i.e., turned on and turned off) either independently or in a coordinated manner. A pulse generator 340 may be used to control the illumination of the interrogation sites by controlling the pulsed radiation sources 210a, 210b, 210c, etc. of the pulsed illumination array 230. In a variation, the signal detection system 800' of particle processing system 100c' includes one or more fluorescence lifetime detectors 830. Detectors 830 measure the lifetime and/or the decay characteristics of the fluorophore signal (in addition to and/or alternatively to measuring the signal's intensity). These signals may be differentiated based on differences in the exponential decay rate of the emitted fluorescence. As such, signals having different fluorescence decay rates may be differentiated, even if the wavelengths of the signals are the same. When fluorescence lifetimes are being detected, ultrashort excitation pulses (such as may be provided, for example, by a pulsed or quasi-continuous-wave laser) may be preferable.

Similarly, referring back to FIGS. 6A and 6B, respective variations 100d', 100e' of the particle processing systems 100d and 100e may be provided with a signal detection system 800' that includes one or more fluorescence lifetime detectors 830.

Figure 7A:
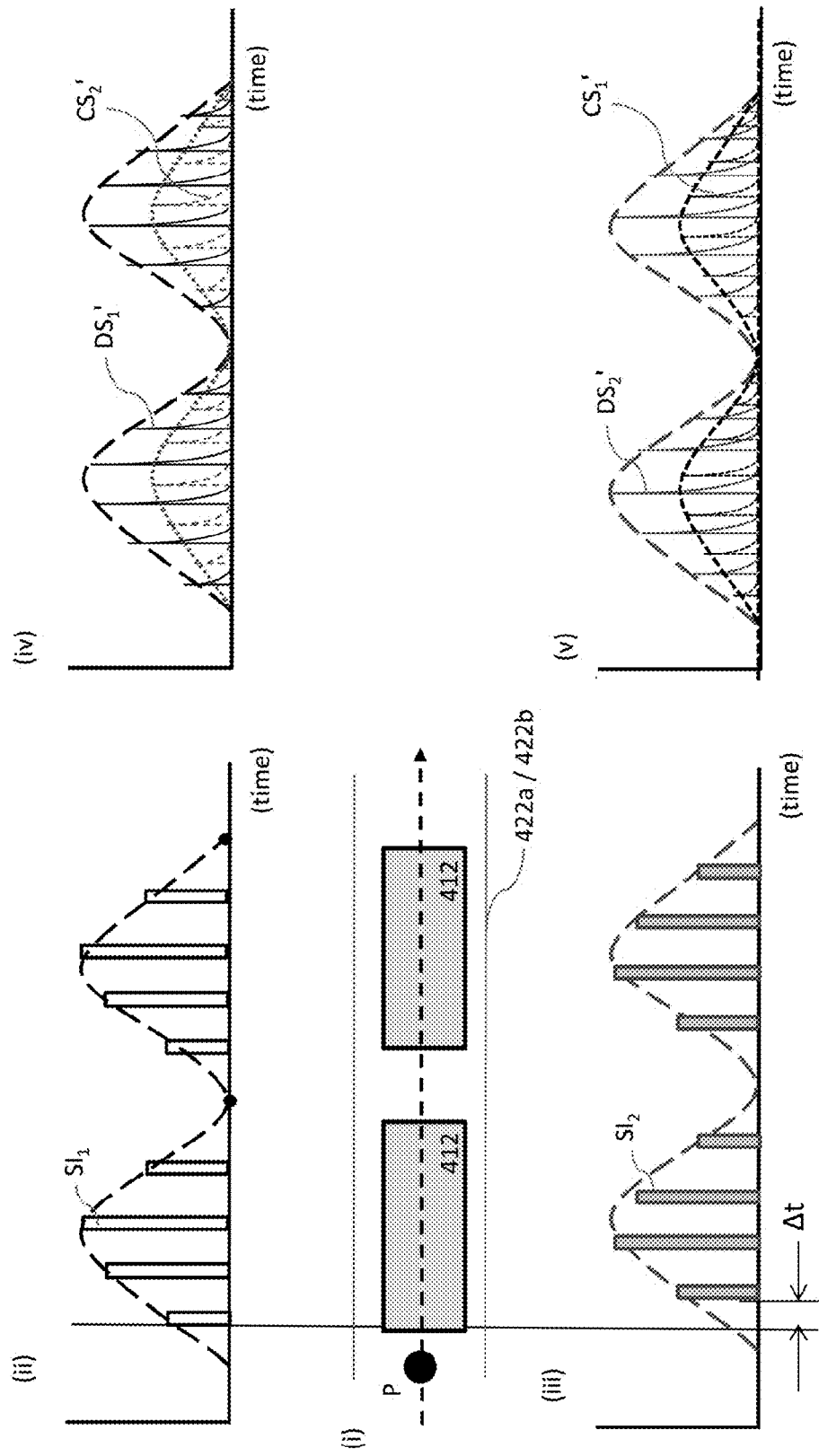

FIG. 7A (similar to FIG. 3B when discussed in the context of FIG. 5 and FIGS. 6A and 6B) illustrates how pulsed illumination may be used to reduce and/or account for optical crosstalk in the signal received by the signal detection system 800' when a single fluorescence lifetime detector 830 is provided per interrogation site per spectral domain (i.e., color). FIG. 7B (similar to FIG. 3E when discussed in the context of FIG. 5 and FIGS. 6A and 6B) illustrates how pulsed illumination may be used to reduce and/or account for crosstalk in the signal received by the signal detection system 800' when a single fluorescence lifetime detector 830 is configured to receive the signals from a plurality of interrogation sites for a single spectral domain (i.e., color). As shown in FIGS. 7A and 7B, the pulsed illumination pattern may be the same as shown in FIGS. 3B(ii) and (iii) and in FIGS. 3E(i) and 3E(ii). However, FIG. 7A(iv) illustrates a typical detected signal $DS_1'$ pattern as may be detected by a first fluorescence lifetime detector 830 associated with a particle or other sample within a first interrogation site 155a; FIG. 7A(v) illustrates a typical detected signal $DS_2'$ pattern as may be detected by a second fluorescence lifetime detector 830 associated with a particle or other sample within a second interrogation site 155b. Specifically, FIG. 7A(iv) illustrates that the fluorescence lifetime detector 830 senses the detected signal $DS_1'$ due to the particle within the first interrogation site and also may sense a crosstalk signal $CS_2'$ due to stray signals emanating from the second interrogation site. However, due to the pulse delay Δt experienced as the interrogation beam 215a pulses the first interrogation site and then the interrogation beam 215b pulses the second interrogation site, any crosstalk signals $CS_2'$ detected by the first fluorescence lifetime detector 830 that are associated with pulsing of the second interrogation site (see (iii)) will be out-of-phase with the signal emanating from the first interrogation site (see (ii)). Similarly, referring to FIG. 7A(v) any crosstalk signals $CS_1'$ detected by the second fluorescence lifetime detector 830 that are associated with the first interrogation site (see (ii)) will be out-of-phase with the detected signal $DS_2'$ emanating from second interrogation site (see (iii)). Thus, in-phase signals due to the detection of a particle within the interrogation site may be isolated from the out-of-phase crosstalk signals due to adjacent interrogation sites being pulsed.

FIG. 7B illustrates a typical detected signal $DS_1'$ pattern as may be detected with a single fluorescence lifetime detector 830 for a first particle within a first interrogation site 155a and a second particle simultaneously within a second interrogation site 155b. The detected signals $DS_1'$ due to the pulses interrogating the first interrogation site 155a and the detected signals $DS_2'$ due to the pulses interrogating the second interrogation site 155b are alternatively received (interleaved) by the fluorescence lifetime detector 830. Given a known scanning pulse delay Δt, and referring to FIG. 7B (iv), these interleaved signals may be electronically separated (for example, using a demultiplexer 920) into electronic signals $ES_1'$ that represent the event at the first interrogation site 155a and electronic signals $ES_2'$ that represent the event at the second interrogation site 155b. Electronic signals $ES_1'$ are 90 degrees out-of-phase with electronic signals $ES_2'$ in this embodiment.

Figure 8B:
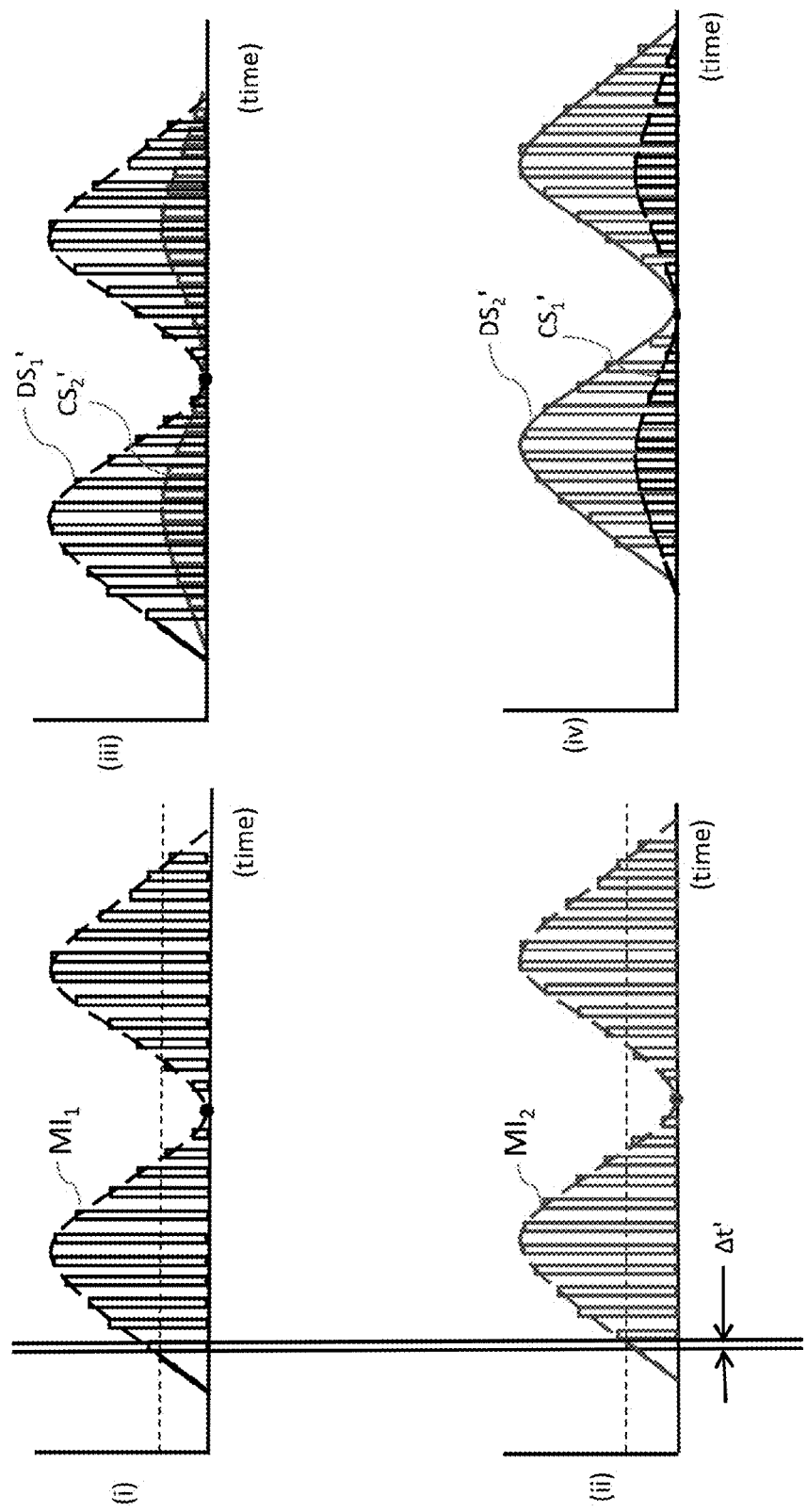

FIGS. 8A and 8B schematically illustrate particle processing systems 100f and 100f' wherein the signal detection system 800 is synchronously locked to a radiation source system

200. Further, the synchronous modulation may be controlled by a trigger associated with a signal from the detection plane 150.

FIG. 8A illustrates a radiation source system 200 having a plurality of radiation sources 210a, 210b, 210c, etc. for illuminating individual interrogation sites 155. These radiation sources 210a, 210b, 210c, etc. are triggered by a modulation controller 930. In this embodiment, the modulation controller 930 may independently trigger each of the radiation sources 210a, 210b, 210c, etc. according to one or more pulsed time delays $\Delta t_0$, $\Delta t_1$, $\Delta t_2$, etc. The modulation controller 930 also controls the signal detection system 800 so that signals detected by the signal detection system 800 are synced to the interrogation beams 215 illuminating the interrogation sites 155. In the embodiment of FIG. 8A, the signal detection system 800 includes an amplifier array 840 and the modulation controller 930 is synced thereto. Signals (e.g, extinction, scatter, etc.) from the detection plane 150 may also be detected by a secondary detector 810b. As one non-limiting example, light scatter 505' from the interrogation sites 155 may be detected by one or more secondary detectors 810b. These signals may be processed by electronics system 900' and provided to modulation controller 930.

FIG. 8B illustrates how locked-in detection may be used to reduce and/or account for crosstalk in the signal received by the signal detection system 800 when a plurality of modulated radiation sources 210a, 210b, etc. is provided for a plurality of interrogation sites 155 according to the embodiment of FIG. 8A. FIG. 8B illustrates idealized timing diagrams for scanning and detection of particles flowing within first and second microfluidic channels, wherein the modulation controller 930 modulates the radiation beam 215 at a single frequency $f_1$ for all interrogation sites (for example, two side-by-side microfluidic flow channels), but with a pulse time delay triggering the illumination for each of the plurality of radiation sources. FIG. 8B(i) illustrates a typical modulated illumination pattern $MI_1$ (intensity versus time) as may be applied to a first microfluidic channel; FIG. 8B(ii) illustrates a typical modulated illumination pattern $MI_2$ as may be applied to a second microfluidic channel. As a particle P flows within the channel it would be illuminated multiple times as the radiation sources 210a, 210b, 210c, etc. (and thus also the interrogation beams 215) are modulated. The trigger delay between an interrogation beam 215 illuminating the first channel and then an interrogation beam 215 illuminating the second channel is shown as $\Delta t'$.

FIG. 8B(iii) illustrates a typical detected signal $DS_1$ pattern as may be detected by a first detector associated with a particle traveling along the first channel (or residing within a first interrogation site); FIG. 8B(iv) illustrates a typical detected signal $DS_2$ pattern as may be detected by a second detector associated with a particle traveling along the second channel (or residing within a second interrogation site). Specifically, FIG. 8B(iii) illustrates that the detector senses the detected signal $DS_1$ due to the particle traveling within the first channel and also may sense a crosstalk signal $CS_2$ due stray signals emanating from the second channel. However, due to the trigger delay $\Delta t$ experienced as the interrogation beam 215 illuminates the first channel and then the second channel, any crosstalk signals $CS_2$ detected by the first detector that are associated with illuminating the second microfluidic channel (see (ii)) will be out-of-phase with the signal emanating from the first microfluidic channel (see (iii)). Similarly, referring to FIG. 8B(iv) any crosstalk signals $CS_1$ detected by the second detector that are associated with illuminating the first microfluidic channel (see (i)) will be out-of-phase with the detected signal $DS_2$ emanating from second microfluidic channel (see (iv)). Thus, in-phase signals due to the detection of a particle within the illuminated channel may be isolated from the out-of-phase crosstalk signals due to adjacent channels being illuminated.

Figure 8C:
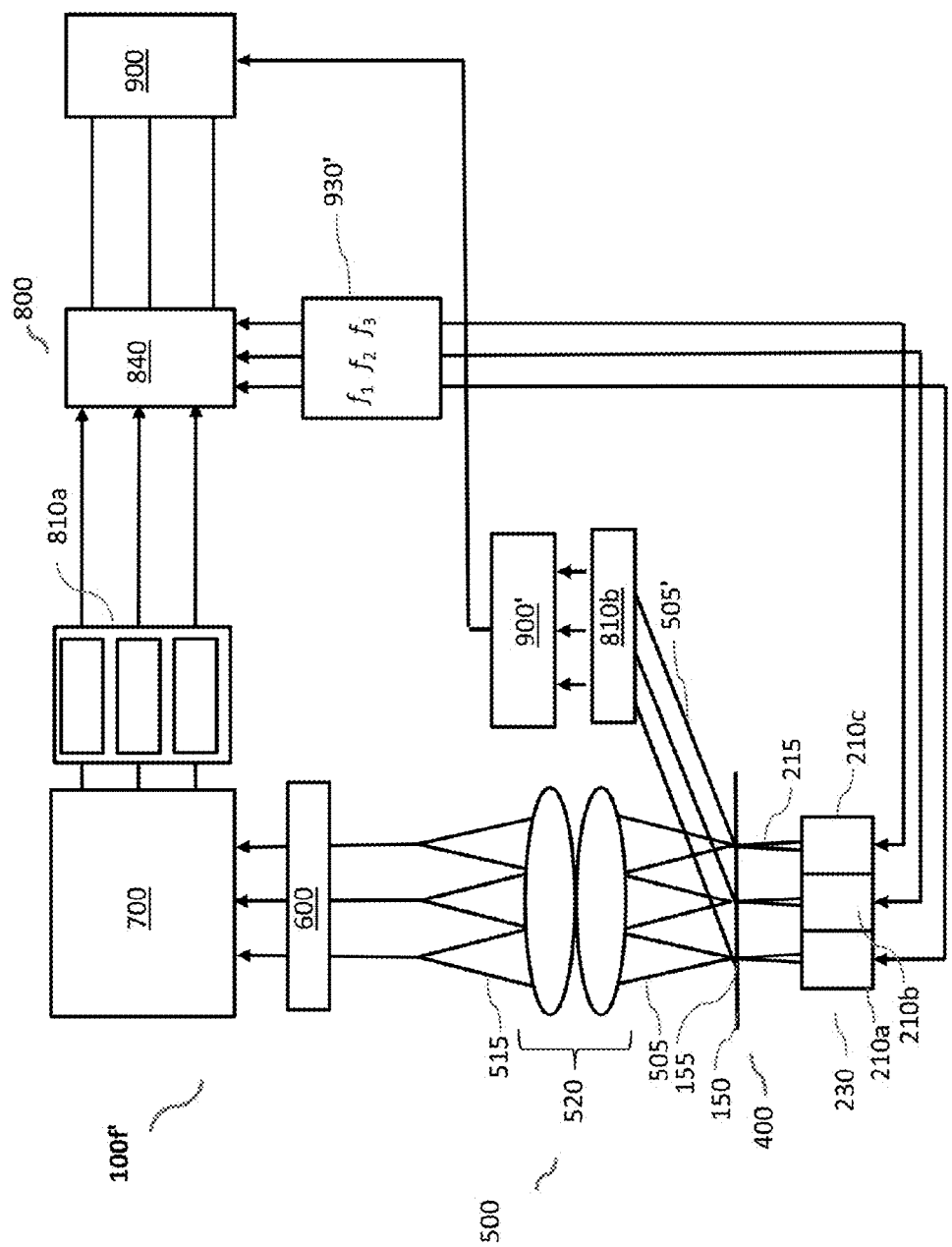

FIG. 8C illustrates a particle processing system 100f' that differs from 100f in that the plurality of radiation sources 210a, 210b, 210c, etc. are triggered by a modulation controller 930'. In this embodiment, the modulation controller 930' may independently trigger each of the radiation sources 210a, 210b, 210c, etc. at one or more frequencies $f_1$, $f_2$, $f_3$, etc. or with a varying frequency pattern $f(t)$.

Figure 8D:
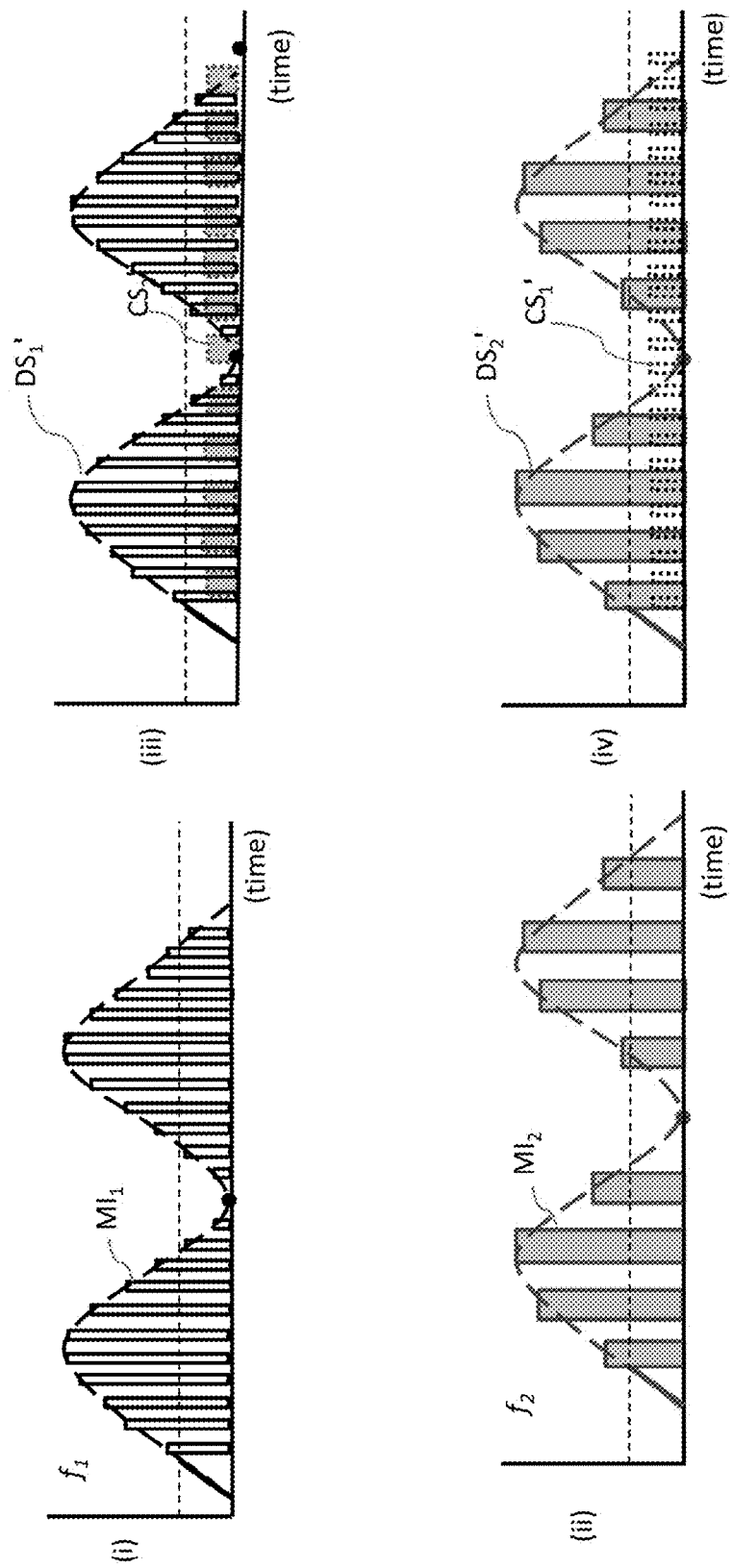

FIG. 8D illustrates how locked-in detection may be used to reduce and/or account for crosstalk in the signal received by the signal detection system 800 when a plurality of modulated radiation sources 210a, 210b, etc. is provided according to FIG. 8C. FIG. 8D(i) illustrates a typical modulated illumination pattern $MI_1$ (intensity versus time) at a first frequency $f_1$ as may be applied to a first channel; FIG. 8D(ii) illustrates a typical modulated illumination $MI_2$ pattern at a second frequency $f_2$ as may be applied to a second channel. FIG. 8D(iii) illustrates a typical detected signal $DS_1$ pattern as may be detected by the single detector for a first particle traveling along the first channel and a second particle simultaneously traveling along the second channel. The detected signals $DS_1$ due to the modulated pulses interrogating the first channel overlap the detected signals $DS_2$ due to the modulated pulses interrogating the second channel. Given the known frequencies of the modulated pulses for each channel, these overlapped signals may be electronically spectrally separated and/or mathematically deconvolved.

FIG. 9A schematically illustrates particle processing system 100g wherein the signal detection system 800 identifies and isolates specific interrogation sites via modulation filters. Thus, a spatial filter array 440 may be provided as spatial illumination patterns and/or as spatial detection patterns. These spatial illumination and/or detection patterns may be provided by masks, aperture arrays, etc. In certain embodiments, patterned gray scale optical masks may be used. The patterned masks may be associated one-to-one with the interrogation sites 155 (e.g., one of the microfluidic flow channels 422). Further, each interrogation site 155 may be provided with a unique spatial filter pattern in which the frequency, period, duty cycle, shape, and/or sized of the aperture in the array may be varied.

According to another aspect, spectral illumination and/or detection patterns may be provided. As a non-limiting example, a spectral filter array (e.g., a spectral optical mask) may be provided, wherein the transmission spectrum of the pattern varies across the array. Thus, each microfluidic flow channel 422 may have a distinct spectral pattern or signature. According to other embodiments (not shown), any combination of spatial modulation and spectral modulation may be combined. The spatial and/or spectral illumination patterns may be provided in the illumination (object) plane, the detection image plane, etc.

Figure 9B:
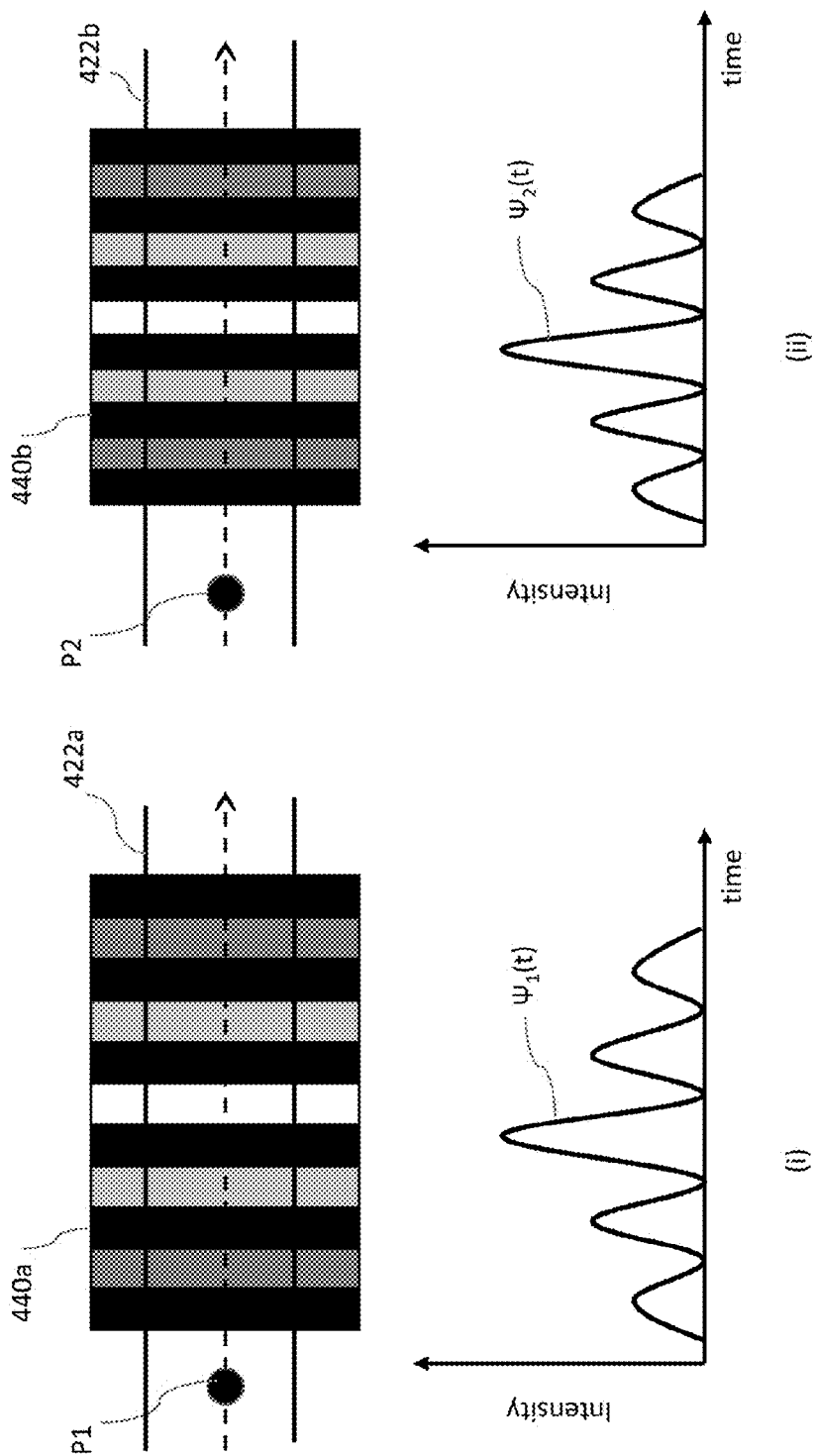

Thus, referring to FIG. 9B(i) a first gray scale mask 440a is shown position over a first flow channel 422a with a particle P1 flowing therein and in FIG. 9B(ii) a second gray scale mask 440b is shown position over a second flow channel 422b with a particle P2 flowing therein. The gray scale bars of the first mask 440a are wider and spacer farther apart than the gray scale bars of the second mask 440b, and thus, the signals produced when the particle passes across the masks have different pulse frequencies. In addition, the spatial frequency may vary across the pattern for a given channel. The different frequencies and varying intensity patterns allow these wavelets $\psi_1(t)$, $\psi_2(t)$ to be identified, isolated and deconvolved (e.g., wavelet analysis) should crosstalk from a neighboring channel be detected along with the detected signal from the illuminated channel. FIG. 9A illustrates a radiation source system 200 having a single radiation source 210 for illuminating a plurality of interrogation sites 155. By way of non-limiting example, the radiation source 210 may be a continuous wave laser. The radiation source system 200 may additionally include beam shaping optics 220 (as shown). The signal detection system 800 may include a single detector associated one-to-one with an interrogation site or microfluidic flow channel. Alternatively, the signal detection system 800 may include a single detector associated with a plurality of interrogation sites or microfluidic flow channels.

Optionally, secondary signals 505' from the detection plane 150 may be detected by a secondary detector 810b. As one non-limiting example, when fluorescence is the primary signal detected, light scatter from the interrogation sites 155 may be detected by one or more secondary detectors 810b. As another example, an extinction signal may be detected by a secondary detector 810b. These secondary signals may be processed by electronics system 900 and may provide a trigger to the controller to illuminate or detect only in the presence of a particle.

Figure 9C:
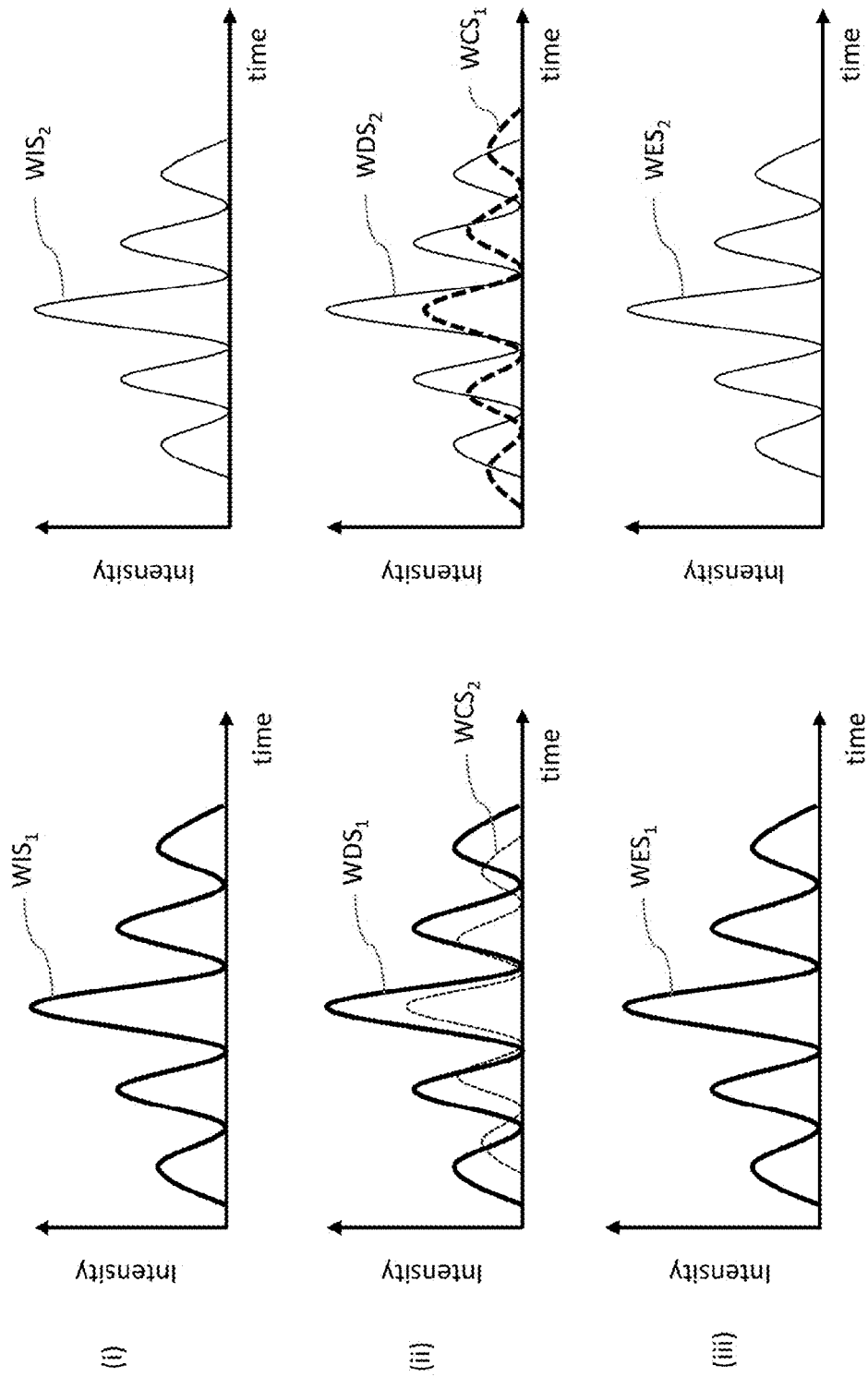
Figure 10:
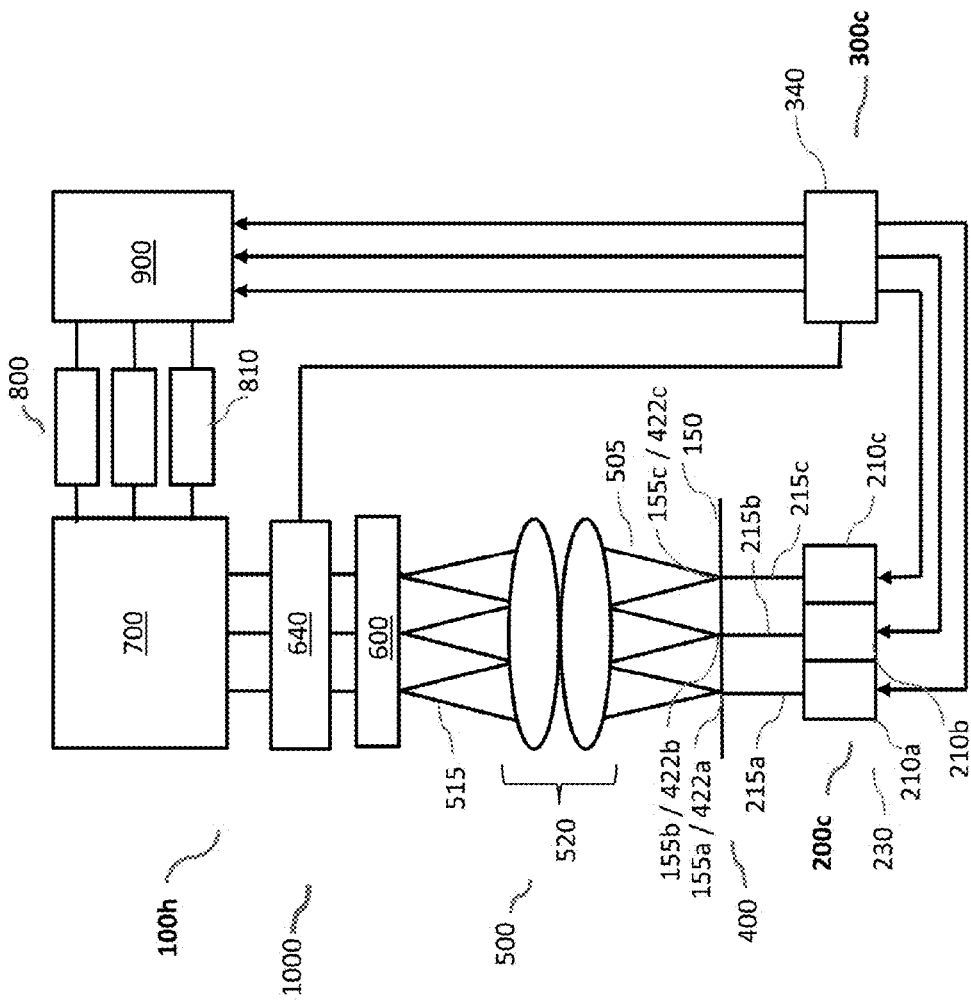

FIG. 9C(i) shows wavelet illumination signals $WIS_1$, $WIS_2$ for first and second microfluidic flow channels 422a, 422b, respectively, when each microfluidic flow channels is associated with a single detector. FIG. 9C(ii) shows wavelet detected signals $WDS_1$, $WDS_2$ for first and second microfluidic flow channels 422a, 422b, respectively, along with wavelet crosstalk signals $WCS_2$, $WCS_1$ for second and first microfluidic flow channels 422b, 422a, respectively, that have infiltrated the primary detected signal. FIG. 9C(iii) the wavelet electronic signals $WES_1$, $WES_2$ for first and second microfluidic flow channels 422a, 422b, respectively, the detected signals have been processed to eliminate the crosstalk signal. FIG. 9D shows the process when a single detector receives signals from a plurality of microfluidic flow channels, as has been describe in the context of scan illumination with respect to FIG. 3E.

Figure 10:
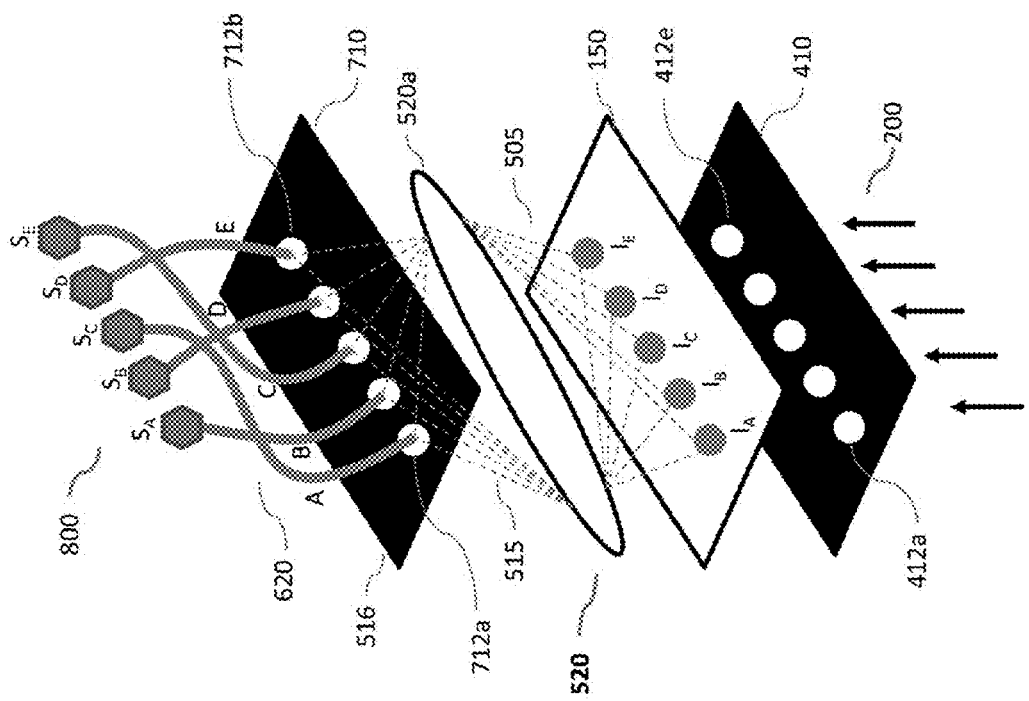
FIG. 10 depicts another exemplary particle processing system, methods and data according to the present disclosure.

The particle processing system 100h of FIG. 10 is very similar to the particle processing systems 100c, 100c' of FIG. 5. In FIG. 10, a spatial filter 640 which may selectively block (or selectively transmit) a signal from one or more interrogation sites 155 is supplied in the detection path. Spatial filter 640 is linked to the pulse generator 340. As discussed with respect to particle processing system 100c, pulse generator 340 controls the illumination of the individual interrogation sites 155 by the radiation sources 210a, 210b, 210c, etc. of the pulsed excitation array 230. In the embodiment of particle processing system 100h, pulse delay generator 340 also controls the opening and closing (i.e., the selective transmission and the selective blocking) of apertures associated with the signals from the individual interrogation sites 155. Thus, spatial filter 640 may be configured as a scanning detection signal aperture blocker (or alternatively, as a scanning detection signal aperture transmitter). When interrogation site 155a is illuminated by interrogation beam 215a, the pulse generator 340 instructs spatial filter 640 to open the aperture associated with the detection signal from interrogation site 155a so that this signal may be detected by detector 810. At the same time, the pulse generator 340 may instruct spatial filter 640 to block some or all of any other signals emanating from the detection plane 150. Similarly, when interrogation site 155b is illuminated by interrogation beam 215b, the pulse generator 340 instructs spatial filter 640 to open the aperture associated with the detection signal from interrogation site 155b so that this signal may be detected by detector 810. At the same time, the pulse generator 340 may instruct spatial filter 640 to block some or all of any other signals emanating from the detection plane 150.

Thus, the idealized timing diagrams of FIG. 3B are also applicable to the particle processing system 100h of FIG. 10 when a single detector is provided per microfluidic channel per spectral domain (i.e., color) and when detection signals from interrogation sites 155a, 155b, 155c, etc. are selectively and synchronously transmitted. Further, the idealized timing diagrams of FIG. 3E are applicable to the particle processing system 100h of FIG. 10 as modified to include a single detector configured to receive signals from a plurality of interrogation sites 155 for a single spectral domain (i.e., color) (see for example, the single detector 810d shown in FIG. 3D) and when detection signals from interrogation sites 155a, 155b, 155c, etc. are selectively and synchronously transmitted. Thus, FIGS. 3B and 3E also illustrate how, according to certain embodiments, pulsed interrogation of a plurality of interrogation sites 155 coupled with selective and synchronous transmission and/or blocking of individual interrogation sites 155a, 155b, etc. may be used to reduce and/or account for crosstalk in the signals received by the signal detection system 800.

Figure 11A:
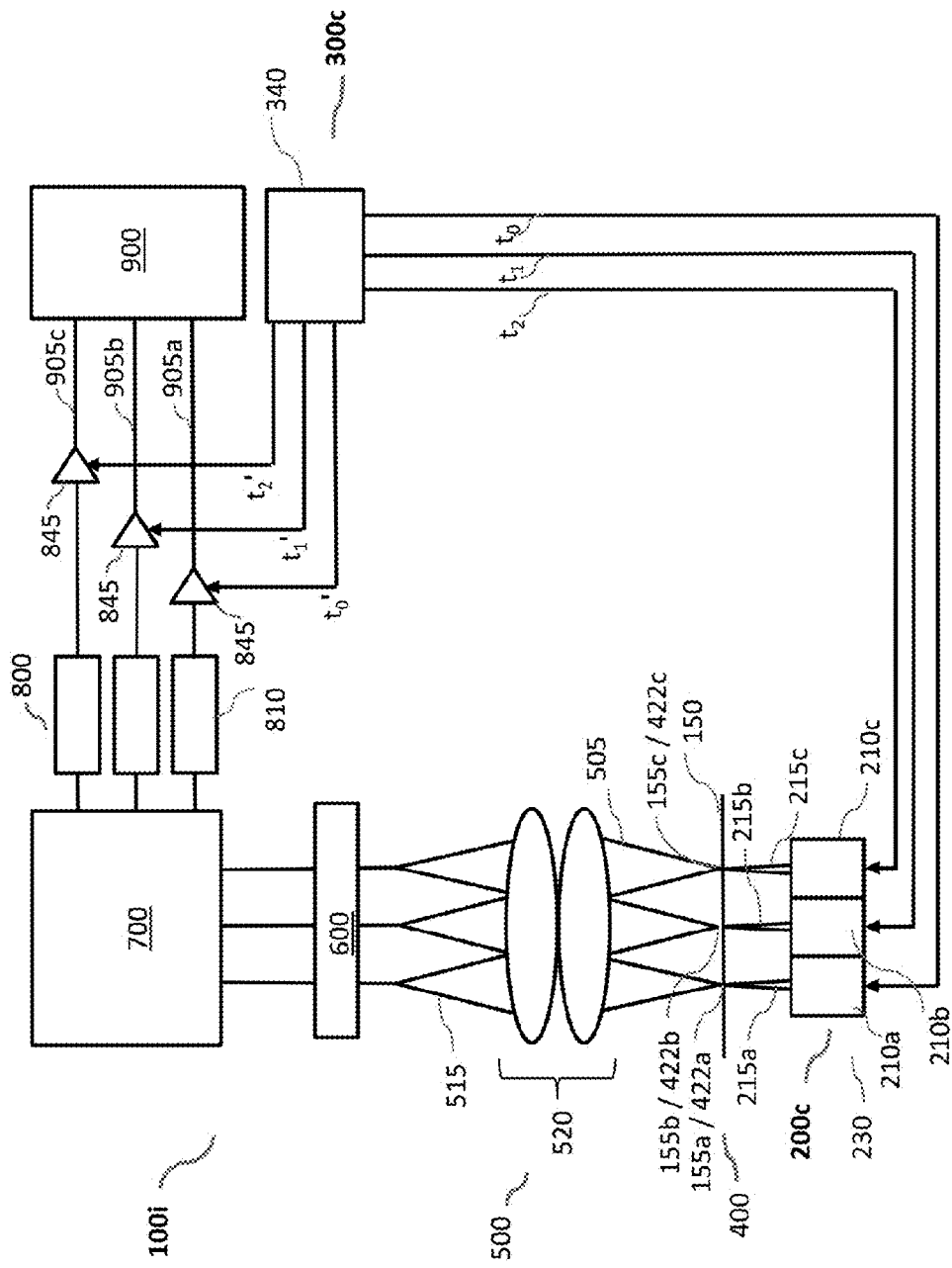
FIGS. 11A-11B depict other exemplary particle processing systems, methods and data according to the present disclosure.
Figure 11B:
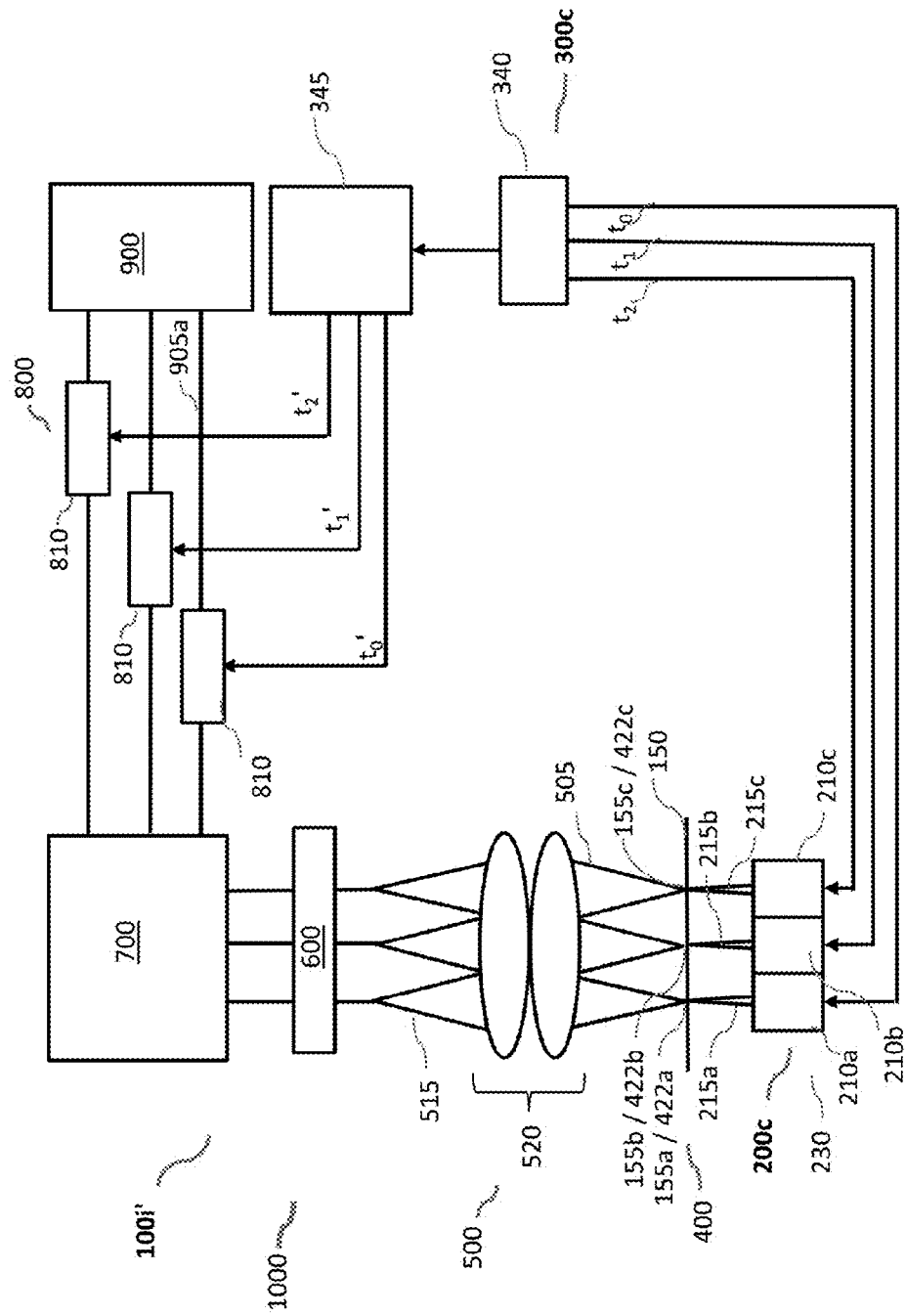

FIGS. 11A and 11B schematically illustrate particle processing systems 100i and 100i' wherein the signals 905a, 905b, 905c etc. sent from the signal detection system 800 to the electronics system 900 are synchronized with pulsed interrogation beams 215a, 215b, 215c, etc. In FIG. 11A, a pulse generator 340 controls the triggering pulses supplied to the radiation sources 210a, 210b, 201c, etc. and also controls pulses that switch that activates the detection electronics 900. Thus, for example, a pulse may be supplied to radiation source 210a via line $t_0$ and at the same time a pulse may be supplied to detection switch 845 via line $t_0'$ so that the signal 905a received by the electronics system 900 is synchronized with the signal 505 emanating from interrogation site 155a. In FIG. 11B, a pulse generator 340 controls the triggering pulses supplied to the radiation sources 210a, 210b, 201c, etc. and also triggers a detector gain/power pulse selector switch 345. The detector gain/power pulse selector switch 345 selectively controls the gain/power associated with the individual detectors 810. Thus, for example, a pulse may be supplied to radiation source 210a via line $t_0$ and at the same time a pulse may be supplied to gain/power pulse selector switch 345 so that signal 905a may be synchronously received by the electronics system 900.

The idealized timing diagrams of FIG. 3B are applicable to the particle processing systems 100i and 100i' of FIGS. 11A and 11B when a single detector is provided per microfluidic channel per spectral domain (i.e., color). FIG. 3B illustrates how synchronously switching detection electronics with the pulsed interrogation beams 215 supplied to the interrogation sites may be used to reduce and/or account for crosstalk.

Figure 12A:
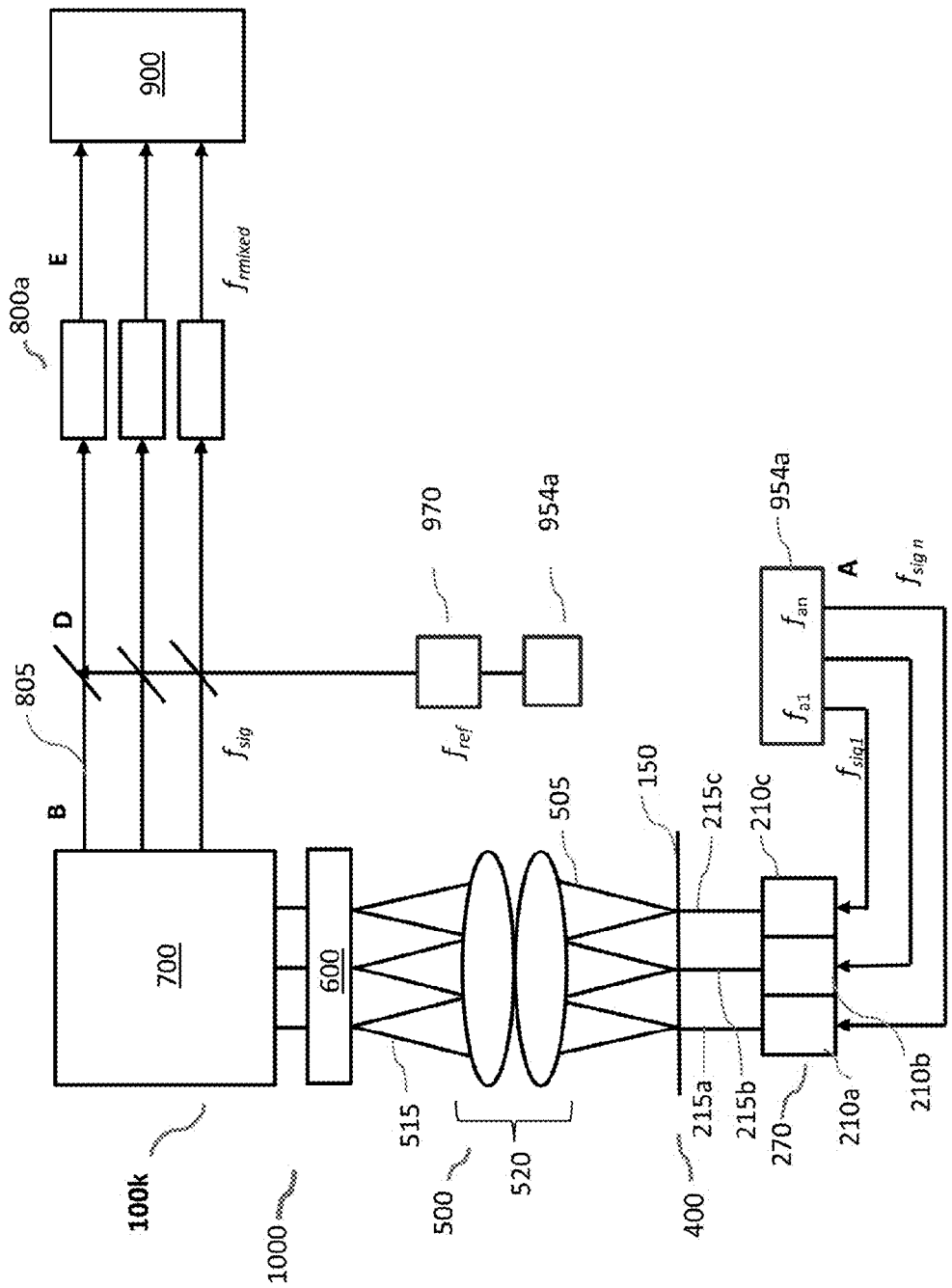
FIGS. 12A-12B depict other exemplary particle processing systems, methods and data according to the present disclosure.
Figure 12B:
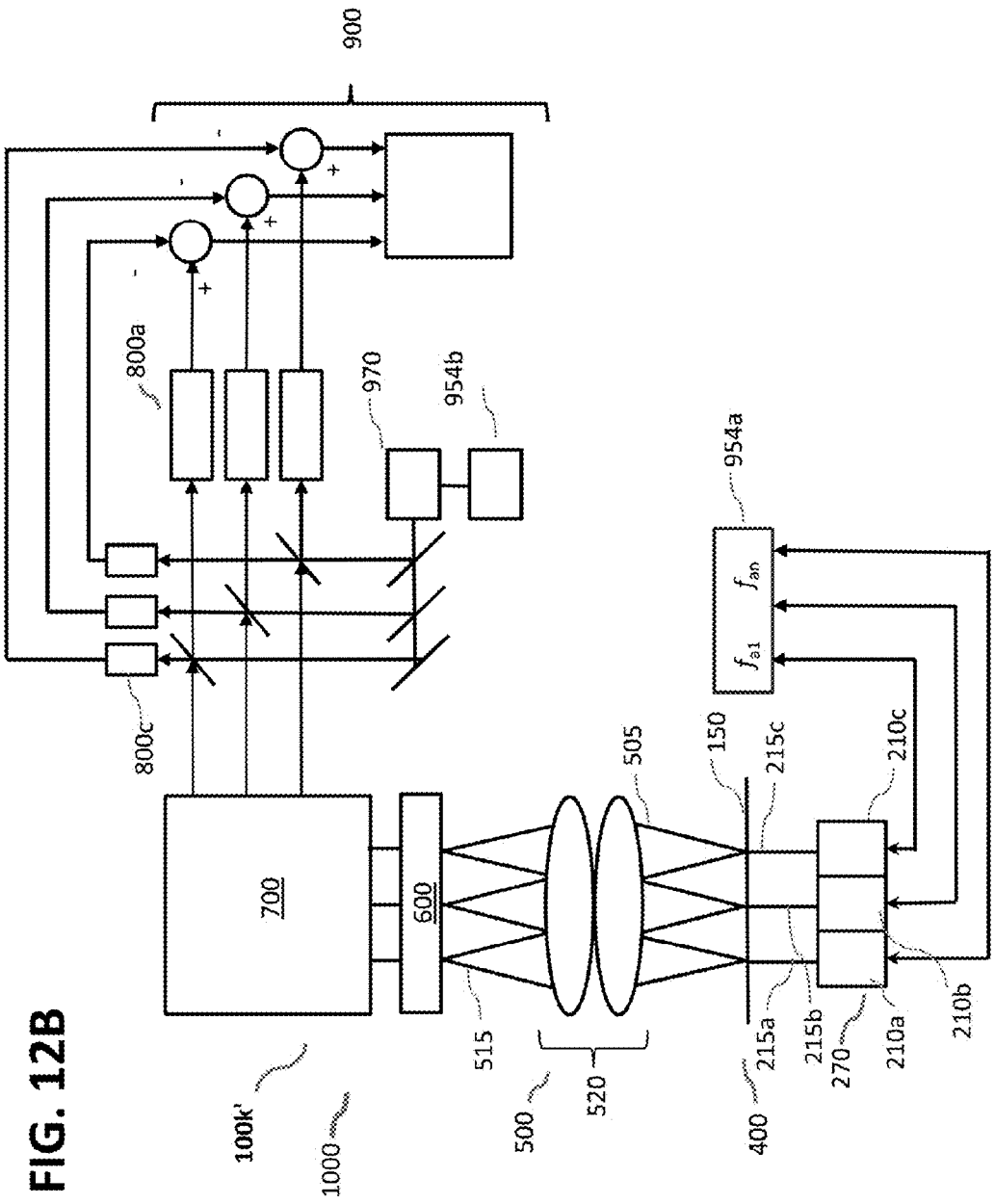

FIGS. 12A-12B schematically illustrate multiple embodiments of particle processing systems 100k, 100k' that use heterodyne optical detection systems. As shown in FIG. 12A, for spatially coherent detected radiation, the radiation source system 200 of particle processing systems 100k, may be, for example, an illumination array 270 driven at a plurality of frequencies ($f_{sig1}$, $f_{sig2}$, $f_{sig3}$, ... $f_{sig\,n}$) supplied by a first electronic frequency generator 954a. The frequency driven illumination array 270 provides pulsed interrogation beams 215a, 215b, 215c, etc. to a plurality of interrogation sites 155. A second electronic frequency generator 954b provides the reference signals to drive an optical local oscillator 970 at a reference frequency ($f_{ref}$) different than those reference signals used to generate the interrogation beams 215. The reference frequency ($f_{ref}$) may preferably be greater than the frequencies used to generate the interrogation beams 215. Emitted signals 505/805 and the reference signal from the optical local oscillator 970 are mixed and detected by the detector array 800 at frequencies ($f_{mixed1}$, $f_{mixed2}$, $f_{mixed3}$, ... $f_{mixed\ n}$). Thus, each interrogation site has an illumination/detection signal frequency $f_{sig}$ associated with it; all interrogation sites share the same reference frequency $f_{ref}$; and each interrogation site also has a mixed frequency $f_{mixed}$ associated with it. The mixed frequency signal consists of several harmonic combinations of the reference, illumination/detection, and crosstalk signals. The electronics system 900 demodulates the illumination/detection signal and the crosstalk signal from the reference frequency. Electronic filters then remove the unwanted crosstalk frequency components from the illumination/detection signal of each channel.

FIG. 12B illustrates a particle processing system 100k' with a balanced optical heterodyne detection system. Although similar to the particle processing system 100k, in the balanced heterodyne system, the illumination/detection signals are mixed with the local oscillator on a secondary detector array. The signals from the secondary detector array 800c are subtracted from the primary detector array 800a. This configuration enables noise generated by the local oscillator to be subtracted from the mixed illumination/detection signal.

Figure 13:
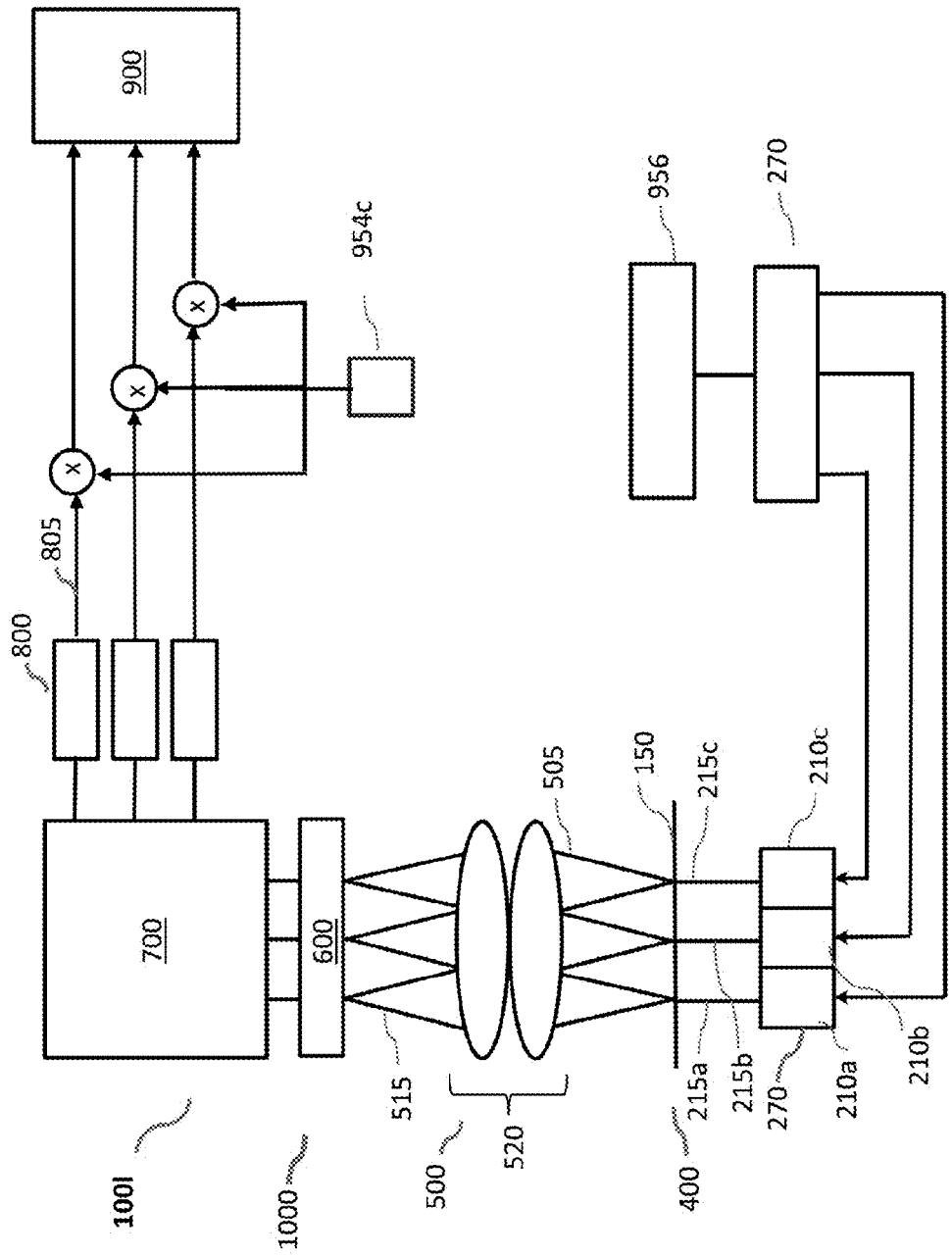
FIG. 13 depicts another exemplary particle processing systems, methods and data according to the present disclosure.

FIG. 13 schematically illustrates an embodiment of a particle processing system 100l that uses a heterodyne optical detection system of spatially incoherent light. Thus, for this embodiment, the radiation source system 200 may be, for example, a illumination array 270 driven at a plurality of frequencies ($f_{sig1}$, $f_{sig2}$, $f_{sig3}$, ... $f_{sig\ n}$) supplied by an electronic signal generator 956. The illumination array 270 provides modulated interrogation beams 215a, 215b, 215c, etc. to a plurality of interrogation sites 155. An electronic oscillator generator 954c provides the reference signals at frequency ($f_{ref}$) which is greater than the frequency of the interrogation beams 215. Signals 805 from the detector array 800 and signals from the electronic oscillator generator 954c are combined in electronics system 900. As with the particle processing systems 100k, 100k', each interrogation site has an illumination/detected signal frequency $f_{sig}$ associated with it; all interrogation sites share the same reference frequency $f_{ref}$; and each interrogation site also have a mixed frequency $f_{mixed}$ associated with it. The mixed frequency signal consists of several harmonic combinations of the reference, illumination/detection, and crosstalk signals. The electronics system 900 demodulates the illumination/detection signal and the crosstalk signal from the reference frequency. Electronic filters then remove the unwanted crosstalk frequency components from the illumination/detection signal of each channel.

According to a variation (not shown) of the particle processing system 100l, a system using a homodyne optical detection system may be provided. Homodyne detection uses a reference frequency to detect frequency-modulated radiation. The reference signal may be supplied by a local frequency generator. The signal and the local oscillator are superimposed at a mixer. In homodyne detection, the local frequency generator has the same frequency as the signal being detected (and, typically, they are both derived from the same source). Homodyne detection systems are generally insensitive to fluctuations in the frequency of the source.

Although the systems, assemblies and methods of the present disclosure have been described with reference to exemplary embodiments thereof, the present disclosure is not limited to such exemplary embodiments and/or implementations. Rather, the systems, assemblies and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

We claim:

1. A particle processing system comprising:
    a particle processing region; and
    a signal processing system in communication with the particle processing region, the signal processing system including:
        an optical system configured to transmit optical signals emitted from a plurality of particle interrogation sites, wherein the plurality of particle interrogation sites are mapped via a plurality of optical paths to a plurality of sensor locations,
        wherein the mapping defines an arrangement of the plurality of optical paths with at least some of the signals from adjacent particle interrogation sites being directed to sensor locations that are not adjacent,
    wherein the signal processing system is configured to reduce optical crosstalk between the plurality of optical paths to improve performance of the particle processing system.

2. The particle processing system of claim 1, wherein the plurality of optical paths includes optical fibers or a fiber bundle.

3. The particle processing system of claim 1, wherein the plurality of optical paths includes mirrors or steering elements.

4. The particle processing system of claim 1, wherein the optical system includes a large span optical system for collection of the emitted optical signals from the plurality of particle interrogation sites.

5. A method of using the particle processing system of claim 1, the method comprising the following steps:
    using a large span optical system for collection of the emitted optical signals from the plurality of particle interrogation sites;
    using one or more spatial filters;
    using isolated optical pick-up systems; and
    using spatially scrambled light mapping.

6. The particle processing system of claim 1, further comprising:
    a multi-element photo-multiplier tube array,
    wherein the multi-element photo-multiplier tube provides the plurality of sensor locations.

7. The particle processing system of claim 6, further comprising:
    a dichroic block, a detector, and a scrambled fiber bundle disposed between the dichroic block and the detector;
    image plane confocal apertures;
    a single lens system; and
    a microfluidic chip array with illumination apertures.

8. The particle processing system of claim 1, wherein the plurality of optical paths includes a scrambled fiber bundle strategically mapped to a sensor scheme that minimizes optical crosstalk.

9. A method for minimizing optical crosstalk using the particle processing system of claim 1, the method comprising:
provide the particle processing system, wherein the particle processing system is configured to emit optical signals having a plurality of spectral wavelengths;
mapping the optical signals to a plurality of sensor locations;
wherein the mapping defines an arrangement of the plurality of optical paths with at least some optical signals having common spectral wavelengths being mapped to sensor locations that are not adjacent.

10. The particle processing system of claim 1, further comprising:
a radiation source system configured to optically interrogate a plurality of interrogation sites;
the signal processing system including a signal detection system including a detector configured to receive optical signals emitted from the plurality of interrogation sites;
a filter array provided as at least one of a spatial filter array and a spectral filter array, the filter array providing a distinctive pattern for adjacent interrogation sites.

11. The particle processing system of claim 10, wherein the filter array is a spatial filter array.

12. The particle processing system of claim 10, wherein the filter array is a spectral filter array.

13. The particle processing system of claim 10, further comprising an electronic system configured to identify the optical signals from the plurality of interrogation sites based on a recognition of the distinctive pattern for each interrogation site.

14. A particle processing system comprising:
a particle processing region; and
a signal processing system in communication with the particle processing region, the signal processing system including:
an optical system configured to transmit optical signals emitted from a plurality of particle interrogation sites, wherein the plurality of particle interrogation sites are mapped via a plurality of optical paths to a plurality of sensor locations,
wherein the mapping defines an arrangement of the plurality of optical paths with at least some of the optical signals having common spectral wavelengths being mapped to sensor locations that are not adjacent,
wherein the signal processing system is configured to reduce optical crosstalk between the plurality of optical paths to improve performance of the particle processing system.

15. A method of using the particle processing system of claim 14, the method comprising the following steps:
using a large span optical system for collection of the emitted optical signals from the plurality of particle interrogation sites;
filtering the emitted optical signals via one or more spatial filters;
transmitting the emitted optical signals via isolated optical pick-up systems; and
sensing the emitted optical signals with a spectrally scrambled light mapped sensor array.

16. The particle processing system of claim 1, wherein the signal processing system includes:
wherein the mapping further defines an arrangement of the plurality of optical paths with at least some optical signals having common spectral wavelengths being mapped to sensor locations that are not adjacent.

17. A particle processing system comprising:
a particle processing region; and
a signal processing system in communication with the particle processing region, the signal processing system including:
a linear array of interrogation sites associated with the plurality of optical paths,
wherein a plurality of optical paths are one-to-one mapped to sensor elements in a two-dimensional array of sensor elements, and
wherein the two-dimensional array of sensor elements is provided by a single photo-multiplier tube,
wherein the signal processing system is configured to reduce optical crosstalk between the plurality of optical paths to improve performance of the particle processing system.

18. The particle processing system of claim 17, wherein the two-dimensional array of sensor elements includes unused sensor elements spatially separating at least some of the mapped sensor elements.

19. The particle processing system of claim 17, wherein at least some of the plurality of optical paths associated with sequentially-arrayed interrogation sites are non-sequentially mapped to the sensor elements.

20. The particle processing system of claim 17, wherein at least some of the plurality of optical paths are associated with signals having common spectral frequencies and wherein at least some of these common spectral optical paths are mapped to non-adjacent sensor elements.

* * * * *